(12) United States Patent
Ghanem et al.

(10) Patent No.: US 8,068,901 B2
(45) Date of Patent: Nov. 29, 2011

(54) METHOD AND APPARATUS FOR ADJUSTING A SENSING PARAMETER

(75) Inventors: Raja N. Ghanem, Edina, MN (US); Robert W. Stadler, Shoreview, MN (US); Xusheng Zhang, Shoreview, MN (US); Karen J. Kleckner, New Brighton, MN (US); Paul G. Krause, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1242 days.

(21) Appl. No.: 11/742,625

(22) Filed: May 1, 2007

(65) Prior Publication Data
US 2008/0275516 A1 Nov. 6, 2008

(51) Int. Cl.
*A61B 5/0402* (2006.01)

(52) U.S. Cl. .................................................. 600/509

(58) Field of Classification Search ............... 607/25–27; 600/509, 515–519, 521
See application file for complete search history.

(56) References Cited

U.S. PATENT DOCUMENTS

| | | | |
|---|---|---|---|
| 4,180,078 A | 12/1979 | Anderson | |
| 4,374,382 A | 2/1983 | Markowitz | |
| 4,548,209 A | 10/1985 | Wielders et al. | |
| 4,556,063 A | 12/1985 | Thompson et al. | |
| 4,567,892 A | 2/1986 | Plicchi et al. | |
| 5,127,404 A | 7/1992 | Wyborny et al. | |
| 5,163,427 A | 11/1992 | Keimel | |
| 5,176,137 A | 1/1993 | Erickson et al. | |
| 5,188,105 A | 2/1993 | Keimel | |
| 5,331,966 A | 7/1994 | Bennett et al. | |
| 5,464,434 A | 11/1995 | Alt | |
| 5,470,345 A | 11/1995 | Hassler et al. | |
| 5,593,431 A | 1/1997 | Sheldon | |
| 5,683,432 A | 11/1997 | Goedeke et al. | |
| 6,236,882 B1 | 5/2001 | Lee et al. | |
| 6,505,067 B1 | 1/2003 | Lee et al. | |
| 6,512,940 B1 | 1/2003 | Brabec et al. | |
| 6,522,915 B1 | 2/2003 | Ceballos et al. | |
| 6,622,046 B2 | 9/2003 | Fraley et al. | |
| 2004/0015197 A1* | 1/2004 | Gunderson | 607/27 |
| 2004/0049120 A1 | 3/2004 | Cao et al. | |
| 2004/0106957 A1 | 6/2004 | Palreddy et al. | |
| 2004/0236380 A1* | 11/2004 | Morris | 607/25 |

FOREIGN PATENT DOCUMENTS

| | | |
|---|---|---|
| WO | WO2004006763 A | 1/2004 |
| WO | WO2004093974 A | 11/2004 |
| WO | 2007117822 A1 | 10/2007 |

OTHER PUBLICATIONS

International Search Report, PCT/US2008/062193, Oct. 27, 2008, 7 Pages.
International Search Report, PCT/US2008, Sep. 30, 2008, 6 Pages.

* cited by examiner

*Primary Examiner* — Carl H Layno
*Assistant Examiner* — Jessica Sarcione
(74) *Attorney, Agent, or Firm* — Michael C. Soldner

(57) ABSTRACT

A method and apparatus of updating a sensing parameter in a medical device that includes sensing cardiac signals, determining intervals in response to the sensed cardiac signals, determining interval patterns associated with the determined intervals, and updating the sensing parameter in response to the determined interval patterns.

14 Claims, 35 Drawing Sheets

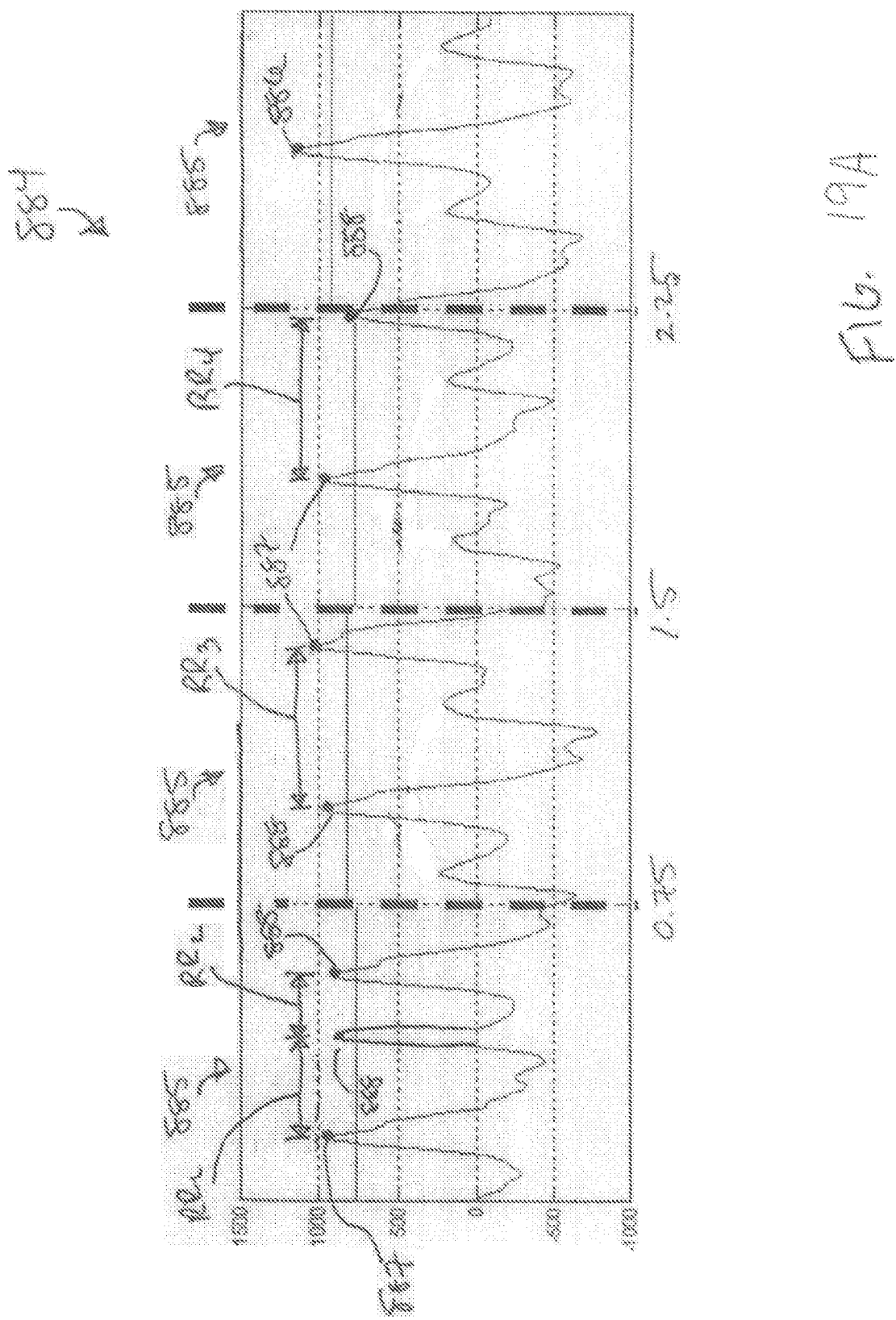

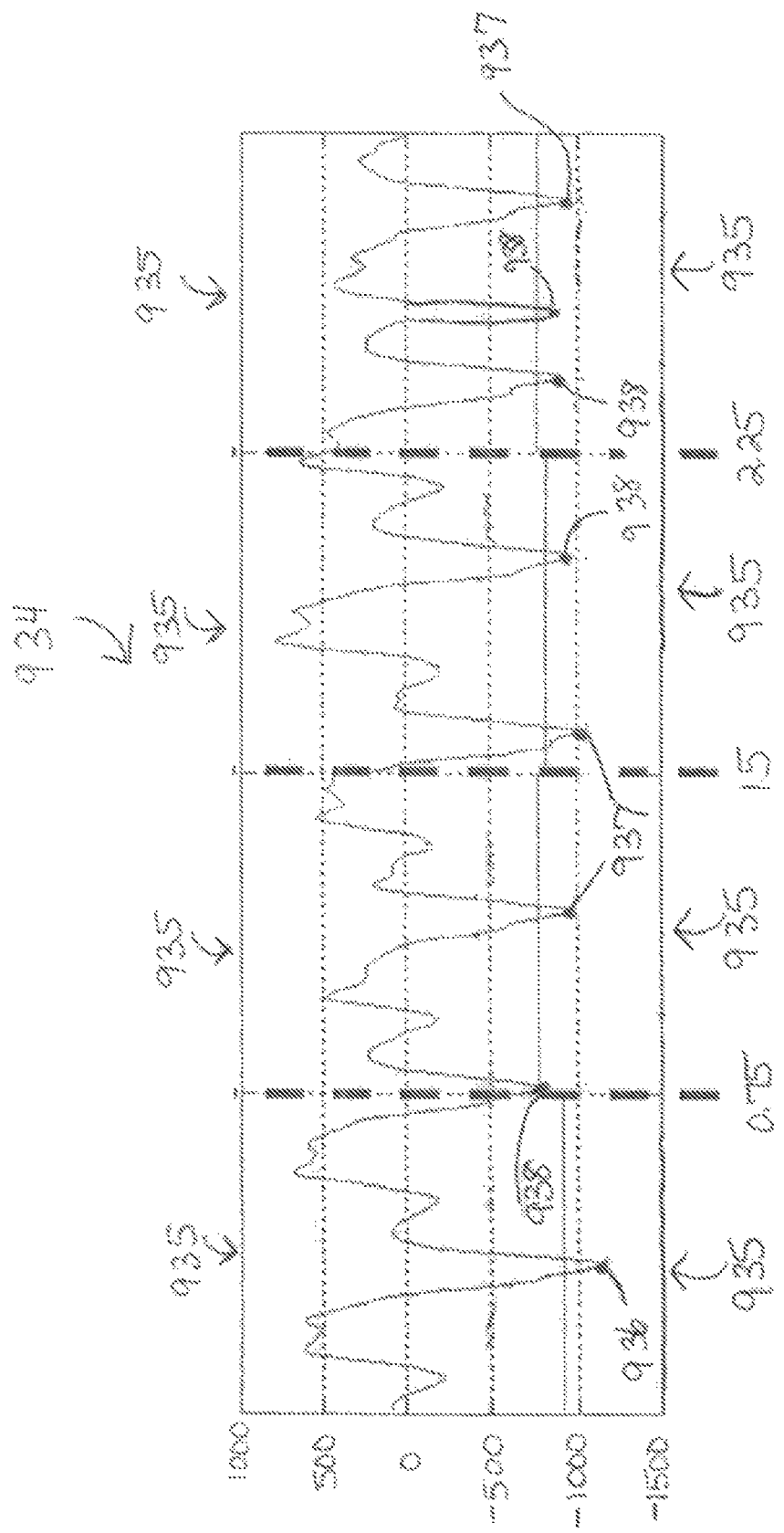

METHOD AND APPARATUS FOR ADJUSTING A SENSING PARAMETER

CROSS-REFERENCE TO RELATED APPLICATION

Cross-reference is hereby made to the commonly-assigned related U.S. Applications, U.S. patent application Ser. No. 11/742,616, which issued as U.S. Pat. No. 7,774,049 on Aug. 10, 2010, and is entitled "METHOD AND APPARATUS FOR DETECTING ARRHYTHMIAS IN A MEDICAL DEVICE", to Ghanem et al.; U.S. application Ser. No. 11/742,618, entitled "METHOD AND APPARATUS FOR DETECTING ARRHYTHMIAS IN A MEDICAL DEVICE", to Ghanem et al.; and U.S. application Ser. No. 11/742,628, entitled "METHOD AND APPARATUS FOR DETECTING ARRHYTHMIAS IN A MEDICAL DEVICE", to Ghanem et al., filed concurrently herewith and incorporated herein by reference in their entireties.

FIELD OF THE INVENTION

The present invention generally relates to an implantable medical device system, and more particularly to a method and apparatus for detecting arrhythmias in a subcutaneous medical device.

BACKGROUND OF THE INVENTION

Many types of implantable medical devices (IMDs) have been implanted that deliver relatively high-energy cardioversion and/or defibrillation shocks to a patient's heart when a malignant tachyarrhythmia, e.g., ventricular tachycardia or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the electrogram (EGM).

The current state of the art of ICDs or implantable pacemaker/cardioverter/defibrillators (PCDs) includes a full featured set of extensive programmable parameters which includes multiple arrhythmia detection criteria, multiple therapy prescriptions (for example, stimulation for pacing in the atrial, ventricular and/or both chambers, bi-atrial and/or bi-ventricular pacing, arrhythmia overdrive or entrainment stimulation, and high level stimulation for cardioversion and/or defibrillation), extensive diagnostic capabilities and high speed telemetry systems.

Current technology for the implantation of an IMD uses a transvenous approach for cardiac electrodes and lead wires. The defibrillator canister/housing is generally implanted as an active can for defibrillation and electrodes positioned in the heart are used for pacing, sensing and detection of arrhythmias.

Attempts are being made to identify patients who are asymptomatic by conventional measures but are nevertheless at risk of a future sudden death episode. Current studies of patient populations, e.g., the MADIT II and SCDHeFT studies, are establishing that there are large numbers of patients in any given population that are susceptible to sudden cardiac death, that they can be identified with some degree of certainty and that they are candidates for a prophylactic implantation of a defibrillator (often called primary prevention).

One option proposed for this patient population is to implant a prophylactic subcutaneous implantable device (SubQ device). As SubQ device technology evolves, it may develop a clear and distinct advantage over non-SubQ devices.

For example, the SubQ device does not require leads to be placed in the bloodstream. Accordingly, complications arising from leads placed in the cardiovasculature environment are eliminated. Further, endocardial lead placement is not possible with patients who have a mechanical heart valve implant and is not generally recommended for pediatric cardiac patients. For these and other reasons, a SubQ device may be preferred over an ICD.

There are technical challenges associated with the operation of a SubQ device. For example, SubQ device sensing is challenged by the presence of muscle artifact, respiration and other physiological signal sources. This is particularly because the SubQ device is limited to far-field sensing since there are no intracardial or epicardial electrodes in a subcutaneous system. Further, sensing of atrial activation from subcutaneous electrodes is limited since the atria represent a small muscle mass and the atrial signals are not sufficiently detectable transthoracically.

Yet another challenge could occur in situations where it is desirable to combine a SubQ device with an existing pacemaker (IPG) in a patient. While this may be desirable in a case where an IPG patient may need a defibrillator, a combination implant of a SubQ device and an IPG may result in inappropriate therapy by the SubQ device, which may pace or shock based on spikes from the IPG. Specifically, each time the IPG emits a pacing stimulus, the SubQ device may interpret it as a genuine cardiac beat. The result can be over-counting beats from the atrium, ventricles or both; or, because of the larger pacing spikes, sensing of arrhythmic signals (which are typically much smaller in amplitude) may be compromised.

Therefore, for these and other reasons, a need exists for an improved method and apparatus to reliably sense and detect arrhythmias in a subcutaneous device, while rejecting noise and other physiologic signals.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein:

FIGS. 19A and 19B are graphical representations of determining a corrected heart rate in response to oversensing according to an embodiment of the present invention;

DETAILED DESCRIPTION OF THE INVENTION

Figure 1:
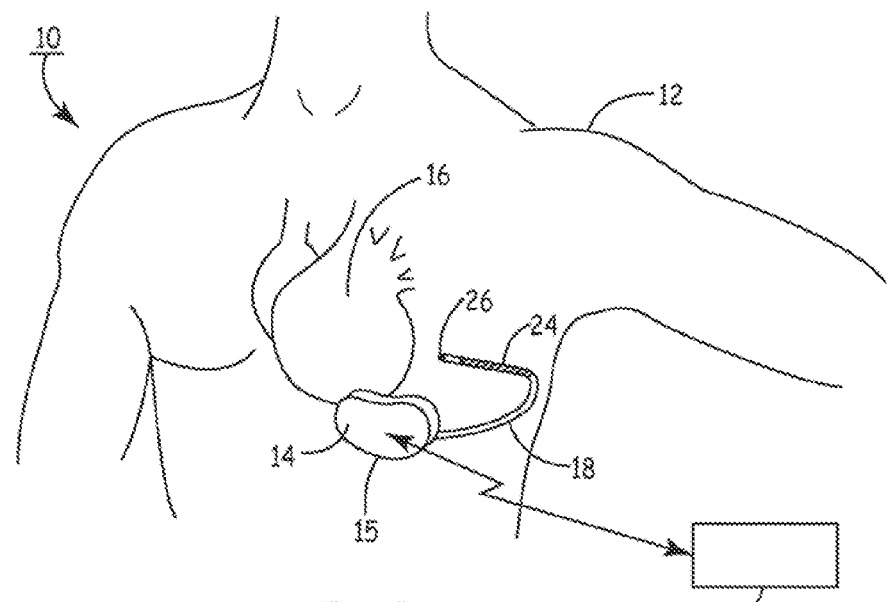
FIGS. 1 and 2 are schematic diagrams of an exemplary subcutaneous device in which the present invention may be usefully practiced.

FIG. 1 is a schematic diagram of an exemplary subcutaneous device in which the present invention may be usefully practiced. As illustrated in FIG. 1, a subcutaneous device 14 according to an embodiment of the present invention is subcutaneously implanted outside the ribcage of a patient 12, anterior to the cardiac notch. Further, a subcutaneous sensing and cardioversion/defibrillation therapy delivery lead 18 in electrical communication with subcutaneous device 14 is tunneled subcutaneously into a location adjacent to a portion of a latissimus dorsi muscle of patient 12. Specifically, lead 18 is tunneled subcutaneously from the median implant pocket of the subcutaneous device 14 laterally and posterially to the patient's back to a location opposite the heart such that the heart 16 is disposed between the subcutaneous device 14 and the distal electrode coil 24 and distal sensing electrode 26 of lead 18.

It is understood that while the subcutaneous device 14 is shown positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Further referring to FIG. 1, a programmer 20 is shown in telemetric communication with subcutaneous device 14 by an RF communication link 22. Communication link 22 may be any appropriate RF link such as Bluetooth, WiFi, MICS, or as described in U.S. Pat. No. 5,683,432 "Adaptive Performance-Optimizing Communication System for Communicating with an Implantable Medical Device" to Goedeke, et al and incorporated herein by reference in its entirety.

Subcutaneous device 14 includes a housing 15 that may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al, both incorporated herein by reference in their entireties. The electronics circuitry of SubQ ICD 14 may be incorporated on a polyimide flex circuit, printed circuit board (PCB) or ceramic substrate with integrated circuits packaged in leadless chip carriers and/or chip scale packaging (CSP).

Subcutaneous lead 18 includes a distal defibrillation coil electrode 24, a distal sensing electrode 26, an insulated flexible lead body and a proximal connector pin 27 (shown in FIG. 2) for connection to the housing 15 of the subcutaneous device 14 via a connector 25. In addition, one or more electrodes 28 (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array.

It is understood that while device 14 is shown with electrodes 28 positioned on housing 15, according to an embodiment of the present invention electrodes 28 may be alternatively positioned along one or more separate leads connected to device 14 via connector 25.

Figure 2:
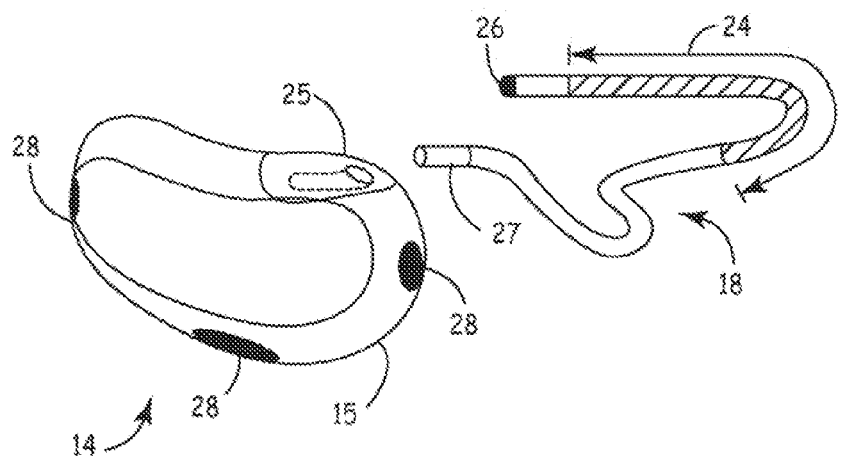

Continuing with FIG. 2, electrodes 28 are welded into place on the flattened periphery of the housing 15. In the embodiment depicted in this figure, the complete periphery of the SubQ ICD may be manufactured to have a slightly flattened perspective with rounded edges to accommodate the placement of the electrodes 28. The electrodes 28 are welded to housing 15 (to preserve hermaticity) and are connected via wires (not shown) to electronic circuitry (described herein below) inside housing 15. Electrodes 28 may be constructed of flat plates, or alternatively, may be spiral electrodes as described in U.S. Pat. No. 6,512,940 "Subcutaneous Spiral Electrode for Sensing Electrical Signals of the Heart" to Brabec, et al and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al, all incorporated herein by reference in their entireties. The electrodes 28 of FIG.2 can be positioned to form orthogonal or equilateral signal vectors, for example.

The electronic circuitry employed in subcutaneous device 14 can take any of the known forms that detect a tachyarrhythmia from the sensed ECG and provide cardioversion/defibrillation shocks as well as post-shock pacing as needed while the heart recovers. A simplified block diagram of such circuitry adapted to function employing the first and second cardioversion-defibrillation electrodes as well as the ECG sensing and pacing electrodes described herein below is set forth in FIG. 3. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the device 14 and external programmer 20.

Figure 3:
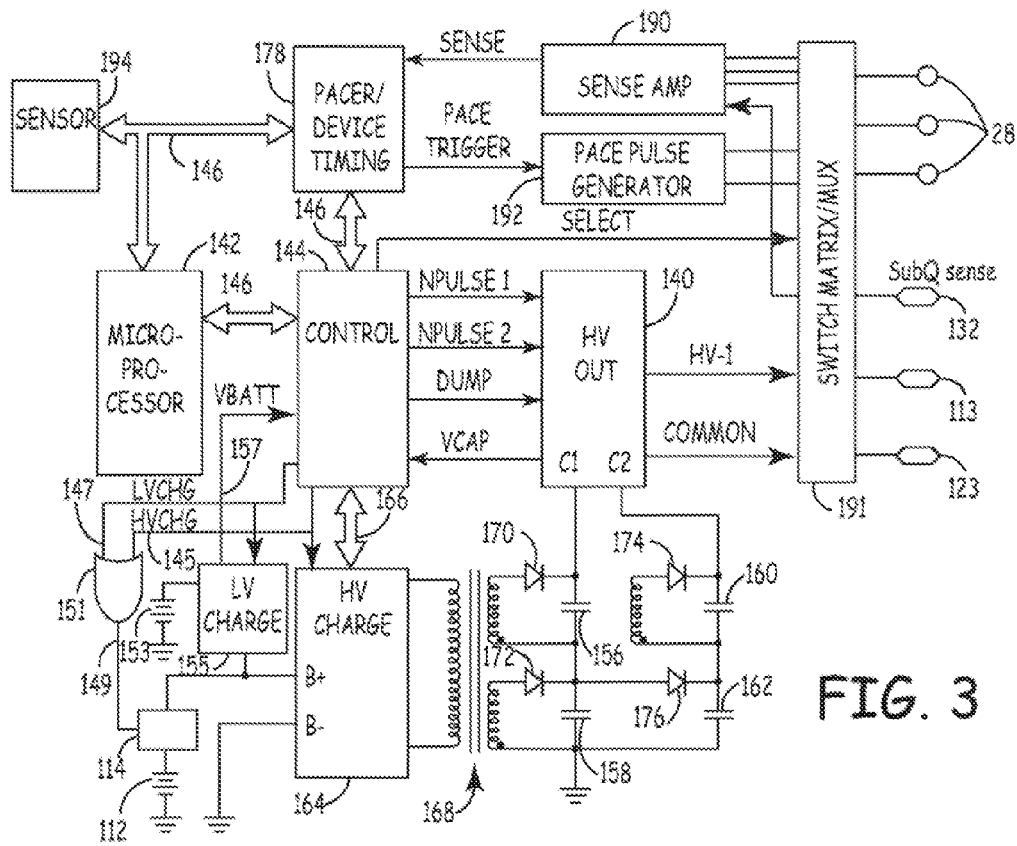
FIG. 3 is an exemplary schematic diagram of electronic circuitry within a hermetically sealed housing of a subcutaneous device of the present invention.

FIG. 3 is an exemplary schematic diagram of electronic circuitry within a hermetically sealed housing of a subcutaneous device according to an embodiment of the present invention. As illustrated in FIG. 3, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 3, according to an embodiment of the present invention, the device 14 could utilize a single battery for both high and low voltage uses.

Further referring to FIG. 3, subcutaneous device 14 functions are controlled by means of software, firmware and hardware that cooperatively monitor the ECG, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posteriorly and subcutaneously and coupled to the HVI output 113 of the high voltage output circuit 140. Outputs 132 of FIG. 3 is coupled to sense electrode 26.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1000 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 3, sense amp 190 in conjunction with pacer/device timing circuit 178 processes the far field ECG sense signal that is developed across a particular ECG sense vector defined by a selected pair of the subcutaneous electrodes 24, 26 and 28, or, optionally, a virtual signal (i.e., a mathematical combination of two vectors) if selected. The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bidirectional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bidirectional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1000V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 113 and 123 coupled to the HV-1 and COMMON output as shown in FIG. 3.

Thus, subcutaneous device 14 monitors the patient's cardiac status and initiates the delivery of a cardioversion-defibrillation shock through the cardioversion-defibrillation electrodes 24 and 28 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only fifteen to twenty seconds, and occurs very infrequently. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 3), so that it is capable of being programmed by means of external programmer 20 via a 2-way telemetry link 22 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bidirectional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn.

Various telemetry systems for providing the necessary communications channels between an external programming unit and an implanted device have been developed and are well known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Figure 4:
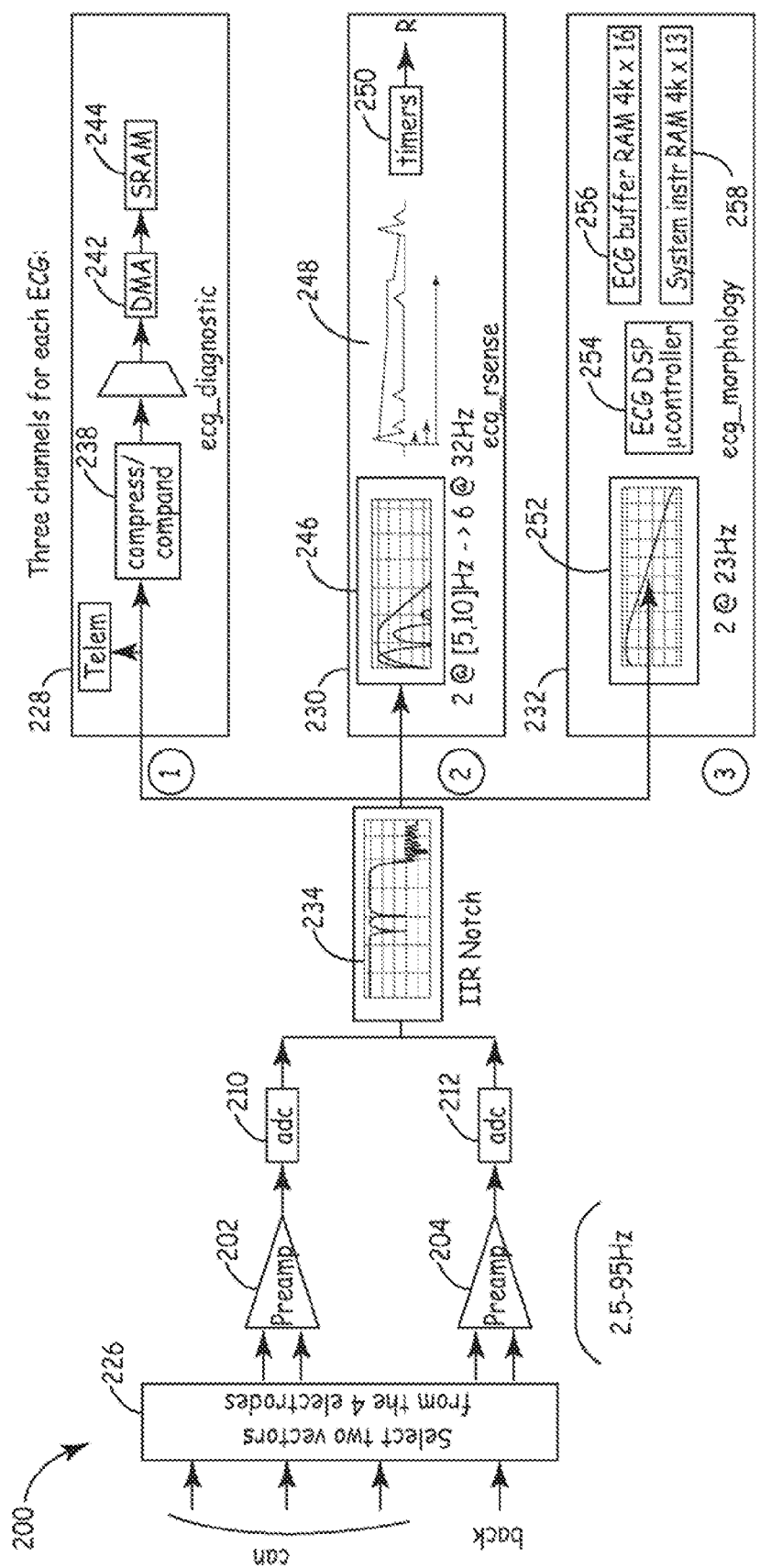
FIG. 4 is a schematic diagram of signal processing aspects of a subcutaneous device according to an exemplary embodiment of the present invention.

FIG. 4 is a schematic diagram of signal processing aspects of a subcutaneous device according to an exemplary embodiment of the present invention. The transthoracic ECG signal (ECG1) detected between the distal electrode 26 of subcutaneous lead 18 and one of electrodes 28 positioned on the subcutaneous device 14 are amplified and bandpass filtered (2.5-105 Hz) by pre-amplifiers 202 and 206 located in Sense Amp 190 of FIG. 3. The amplified EGM signals are directed to A/D converters 210 and 212, which operate to sample the time varying analog EGM signal and digitize the sampled points. The digital output of A/D converters 210 and 212 are applied to temporary buffers/control logic, which shifts the digital data through its stages in a FIFO manner under the control of Pacer/Device Timing block 178 of FIG. 3. Virtual Vector block 226 selects one housing-based ECG signal (ECG2) from any pair of electrodes 28 as described, for example, in U.S. Pat. No. 5,331,966 "Subcutaneous Multi-Electrode Sensing System, Method and Pacer" to Bennett, et al or, alternatively, generates a virtual vector signal under control of Microprocessor 142 and Control block 144 as described in U.S. Pat. No. 6,505,067 "System and Method for Deriving Virtual ECG or EGM Signal" to Lee, et al; both patents incorporated herein by reference in their entireties. ECG1 and ECG2 vector selection may be selected by the patient's physician and programmed via telemetry link 22 from programmer 20.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 device in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity).

If infrequent automatic, periodic measurements are made, it may also be desirable to measure noise (e.g., muscle, motion, EMI, etc.) in the signal and postpone the vector selection measurement when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture.

In the preferred embodiment, vector quality metric calculations would occur a number of times over approximately 1 minute, once per day, for each vector. These values would be averaged for each vector over the course of one week. Averaging may consist of a moving average or recursive average depending on time weighting and memory considerations. In this example, the preferred vector(s) would be selected once per week.

Continuing with FIG. 4, a diagnostic channel 228 receives a programmable selected ECG signal from the housing based subcutaneous electrodes and the transthoracic ECG from the distal electrode 26 on lead 18. Block 238 compresses the digital data, the data is applied to temporary buffers/control logic 218 which shifts the digital data through its stages in a FIFO manner under the control of Pacer/Device Timing block 178 of FIG. 3, and the data is then stored in SRAM block 244 via direct memory access block 242.

The two selected ECG signals (ECG1 and ECG2) are additionally used to provide R-wave interval sensing via ECG sensing block 230. IIR notch filter block 246 provides 50/60 Hz notch filtering. A rectifier and auto-threshold block 248 provides R-wave event detection as described in U.S. Pat. No. 5,117,824 "Apparatus for Monitoring Electrical Physiologic Signals" to Keimel, et al; publication WO2004023995 "Method and Apparatus for Cardiac R-wave Sensing in a Subcutaneous ECG Waveform" to Cao, et al and U.S. Publication No. 2004/0260350 "Automatic EGM Amplitude Measurements During Tachyarrhythmia Episodes" to Brandstetter, et al, all incorporated herein by reference in their entireties. The rectifier of block 248 performs full wave rectification on the amplified, narrowband signal from bandpass filter 246. A programmable fixed threshold (percentage of peak value), a moving average or, more preferably, an auto-adjusting threshold is generated as described in the '824 patent or '350 publication. In these references, following a detected depolarization, the amplifier is automatically adjusted so that the effective sensing threshold is set to be equal to a predetermined portion of the amplitude of the sensed depolarization, and the effective sensing threshold decays thereafter to a lower or base-sensing threshold. A comparator in block 248 determines signal crossings from the rectified waveform and auto-adjusting threshold signal. A timer block 250 provides R-wave to R-wave interval timing for subsequent arrhythmia detection (to be described herein below). The heart rate estimation is derived from the last 12 R-R intervals (e.g., by a mean, trimmed mean, or median, for example), with the oldest data value being removed as a new data value is added.

Figure 5:
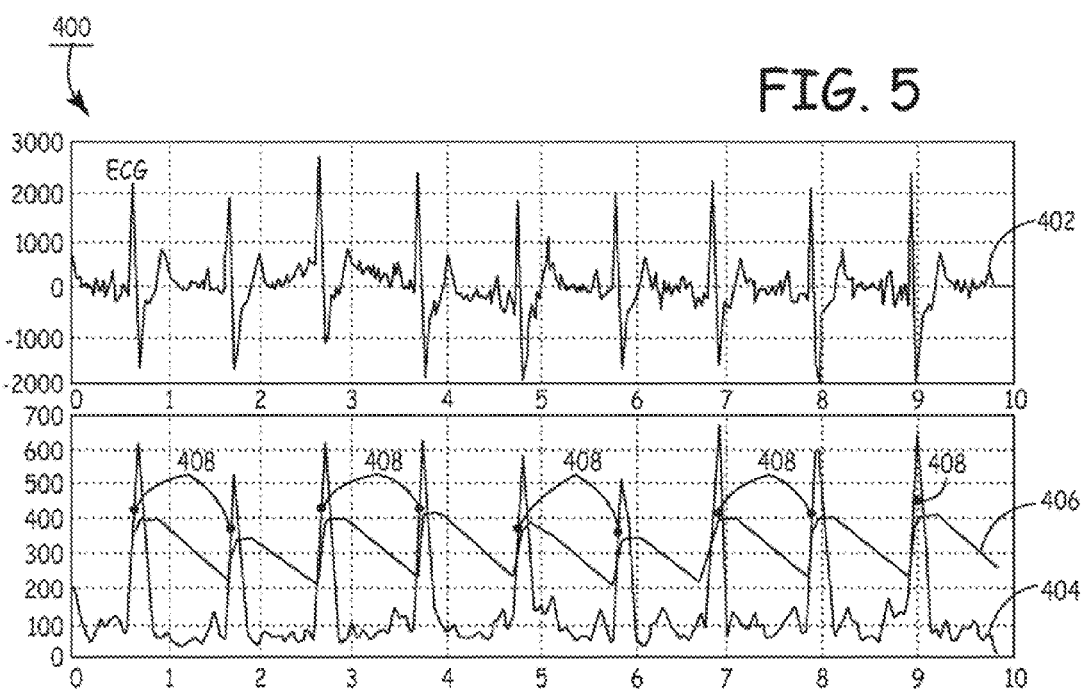
FIG. 5 is a state diagram of detection of arrhythmias in a subcutaneous device according to an embodiment of the present invention.

FIG. 5 is a schematic diagram of a rectifier and auto-threshold unit in a subcutaneous device according to an embodiment of the present invention. Waveform 402 depicts a typical subcutaneous ECG waveform and waveform 404 depicts the same waveform after filtering and rectification. A time dependant threshold 406 allows a more sensitive sensing threshold temporally with respect to the previous sensed R-wave. Sensed events 408 indicate when the rectified ECG signal 404 exceeds the auto-adjusting threshold and a sensed event has occurred.

Returning to FIG. 4, the subcutaneous ECG signal (ECG1) is applied to ECG morphology block 232, filtered by a 2-pole 23 Hz low pass filter 252 and evaluated by DSP microcontroller 254 under control of program instructions stored in System Instruction RAM 258. ECG morphology is used for subsequent rhythm detection/determination (to be described herein below).

Figure 6:
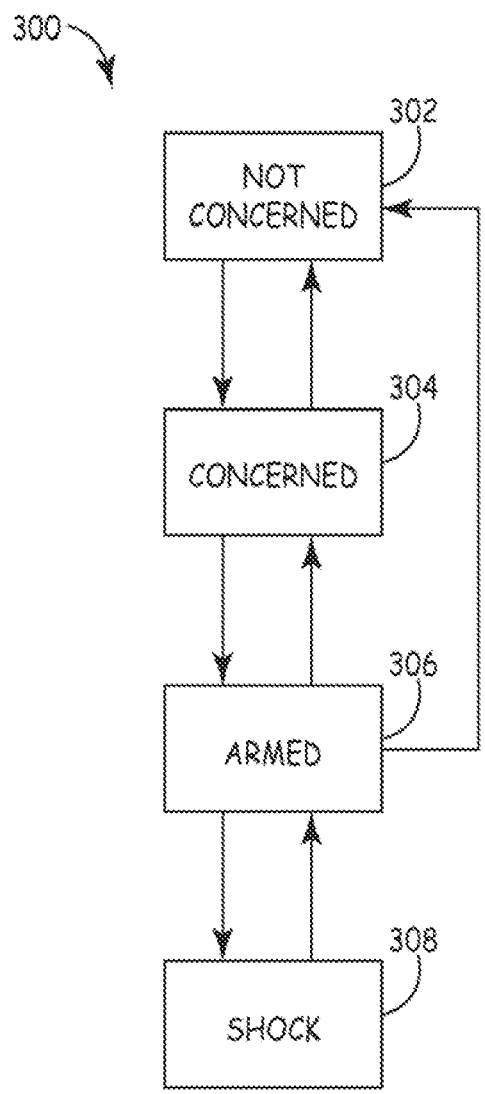
FIG. 6 is a flow chart of a method for detecting arrhythmias in a subcutaneous device according to an embodiment of the present invention.

FIG. 6 is a state diagram of detection of arrhythmias in a medical device according to an embodiment of the present invention. As illustrated in FIG. 6, during normal operation, the device 14 is in a not concerned state 302, described in more detail herein below, during which R-wave intervals are being evaluated to identify periods of rapid rates and/or the presence of asystole. Upon detection of short R-wave intervals simultaneously in both ECG leads, indicative of an event that, if confirmed, may require the delivery of therapy, the device 14 transitions from the not concerned state 302 to a concerned state 304, described in more detail herein below. In the concerned state 304 the device 14 evaluates a predetermined window of ECG signals to determine the likelihood that the signal is corrupted with noise and to discriminate rhythms requiring shock therapy from those that do not require shock therapy, using a combination of R-wave intervals and ECG signal morphology information.

If a rhythm requiring shock therapy continues to be detected while in the concerned state 304, the device 14 transitions from the concerned state 304 to an armed state 306, described in more detail herein below. If a rhythm requiring shock therapy is no longer detected while the device is in the concerned state 304 and the R-wave intervals are determined to no longer be short, the device 14 returns to the not concerned state 302. However, if a rhythm requiring shock therapy is no longer detected while the device is in the concerned state 304, but the R-wave intervals continue to be detected as being short, processing continues in the concerned state 304.

In the armed state 306, the device 14 charges the high voltage shocking capacitors and continues to monitor R-wave intervals and ECG signal morphology for spontaneous termination. If spontaneous termination of the rhythm requiring shock therapy occurs, the device 14 returns to the not concerned state 302. If the rhythm requiring shock therapy is still determined to be occurring once the charging of the capacitors is completed, the device 14 transitions from the armed state 306 to a shock state 308, described in more detail herein below.

In the shock state 308, the device 14 delivers a shock and returns to the armed state 306 to evaluate the success of the therapy delivered.

Figure 7A:
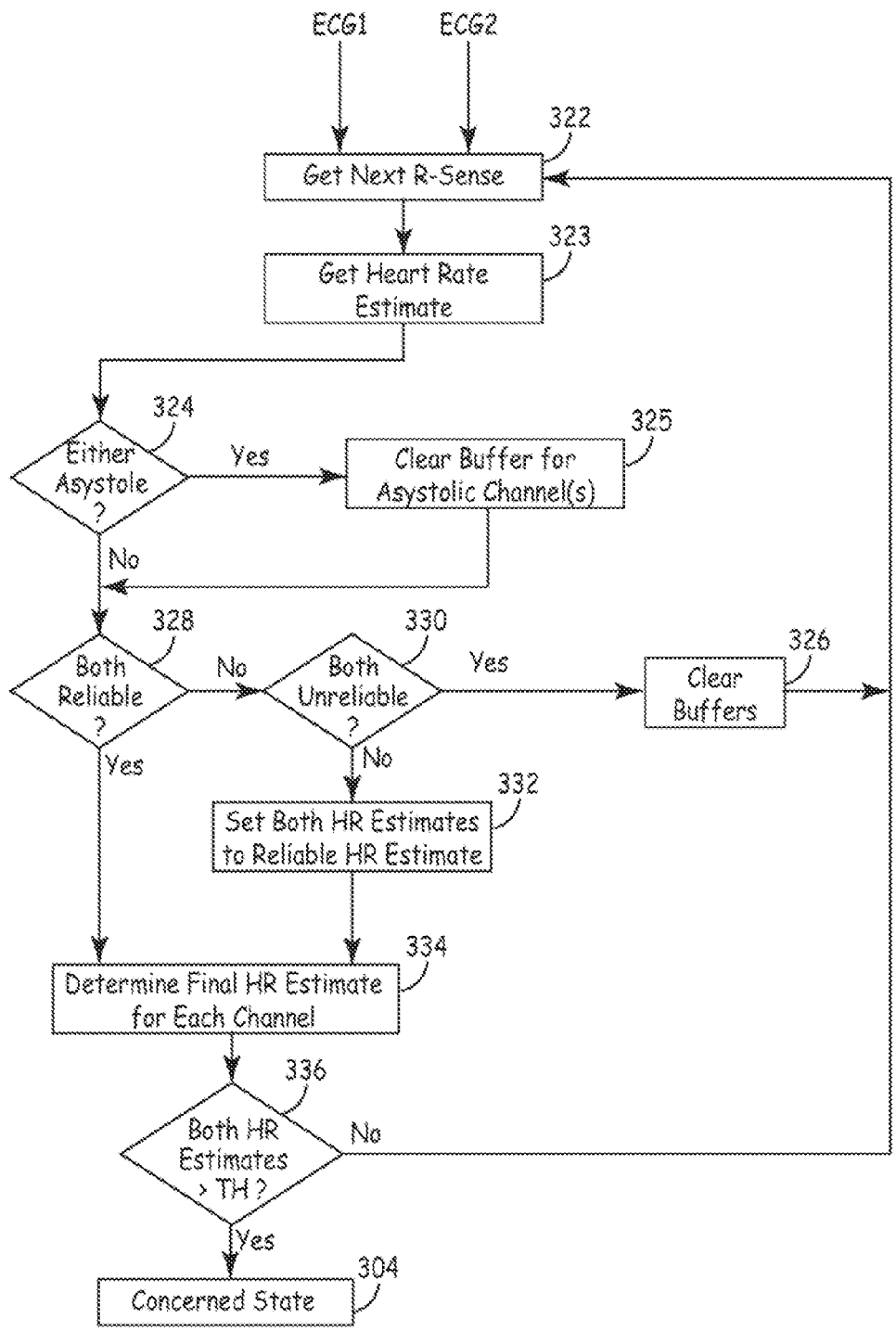
FIGS. 7A-7J are flow charts of a method for detecting arrhythmias in a subcutaneous device according to an embodiment of the present invention.

FIGS. 7A-7I are flow charts of a method for detecting arrhythmias in a subcutaneous device according to an embodiment of the present invention. As illustrated in FIG. 7A, device 14 continuously evaluates the two channels ECG1 and ECG2 associated with two predetermined electrode vectors to when sensed events occur. For example, the electrode vectors for the two channels ECG1 and ECG2 may include a horizontal vector selected between two of the electrodes 28 (ECG2) located along the housing of the device 14 as one electrode vector, while the other electrode vector is a front to back vector selected between the distal electrode 26 (ECG1) and one of the subcutaneous electrodes 28, for example. The input signal from each channel ECG1 and ECG2 is pre-processed and rectified, and an adaptive auto-adjusting threshold is then applied. According to an embodiment of the present invention, a sensed event is determined to have occurred, for example, whenever the rising edge of the filtered ECG crosses the threshold.

Figure 8:
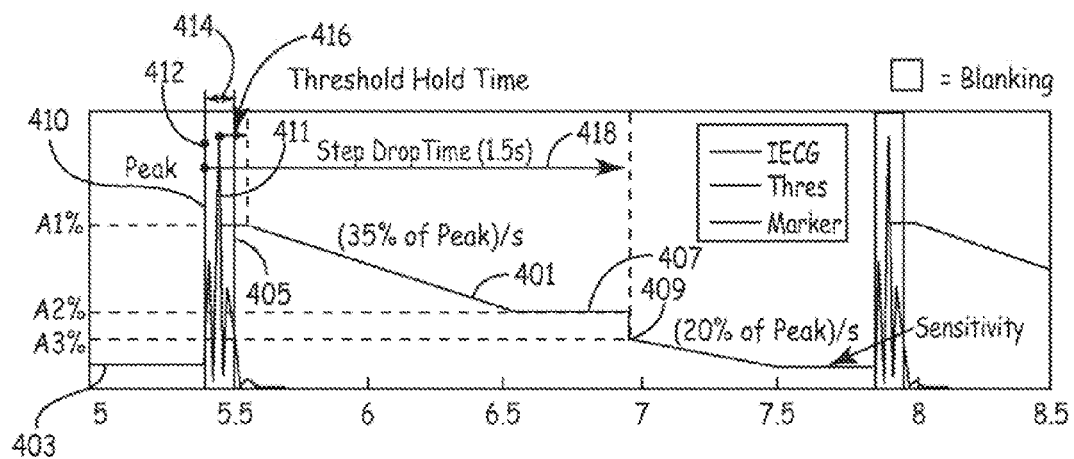
FIG. 8 is a graphical representation of sensing of cardiac activity according to an embodiment of the present invention.

FIG. 8 is a graphical representation of sensing of cardiac activity according to an embodiment of the present invention. In particular, the present invention utilizes an adaptive auto-adjusting threshold 401 during the R-wave sensing of Block 322 that includes a first threshold level 403, a second threshold level 405, a third threshold level 407 and a fourth threshold level 409. An example of an auto-adjusting threshold is described, for example, in commonly assigned U.S. Patent Application Publication No. 2004/0049120, to Cao et al., filed Sep. 11, 2002, incorporated herein by reference in its entirety. Once there is a sensed event, which occurs whenever the rising edge of the rectified filtered ECG 411 crosses the threshold level, in this case threshold 403, indicated by marker 410, the threshold 401 is adjusted to the second threshold level 405, which is a first predetermined percentage of a peak amplitude 412 of the rectified filtered ECG 411, such as 65 percent, for example.

A blanking period 414 (nominally 150 ms, for example) prevents double counting of R-waves. During blanking period 414, the threshold 401 continues to track the predetermined percentage of rectified filtered ECG 411 until peak 412 is detected. Threshold 401 is held at the second threshold level 405 during a threshold hold time period 416 (nominally 100 ms, for example) starting from the peak 412 location to prevent T-wave oversensing by delaying the linear decay. Threshold 401 then decays at a first predetermined rate, such as 35% of peak 412 per second, for example, until threshold 401 reaches the third threshold level 407, which is a second predetermined percentage of peak amplitude 412 (nominally 30%, for example). Threshold 401 is held at the third threshold level 407 until a step drop time 418 from the sensed event 410 (1.5 sec, for example) has expired. Once the step drop time 418 has expired, the threshold 401 is instantaneously set at the fourth threshold level 409 and begins to decay at a second predetermined rate, such as 20% of peak 412 per second, for example. The threshold 401 continues to decay linearly at the second predetermined rate until the threshold 401 reaches the first threshold level 403. At no time can the threshold 401 become less than the first threshold level 403.

The step drop time 418 allows abrupt adjustment of the threshold 401 in order to accommodate sensing of sudden reductions in R-wave amplitudes. The second predetermined rate associated with the linear decay is set at a rate that prevents oversensing of P-waves while maintaining adequate decay for sensing sudden drops in R-waves. If, at any time throughout this threshold adjustment process, a sensed event re-occurs outside blanking period 414, then the threshold 401 is adjusted to the second threshold level 405, and the threshold adjustment process is repeated.

According to an embodiment of the present invention, the nominal settings for the R-wave detector parameters may be set, for example, with the first threshold level being 25 microvolts, the second threshold level, third threshold level and fourth threshold level being set as 65, 30 and 20 percent of the peak amplitude 412, respectively, blanking period 414 being set as 150 milliseconds, threshold hold time 416 being set as 100 milliseconds, and a maximum threshold level being 650 microvolts. These nominal settings may differ between the anterior housing-based bipolar ECG and the front to back ECG in order to account for the expected difference in amplitude and noise characteristics for those vectors.

The R-wave sensing described above is applied to each ECG channel ECG1 and ECG2 independently. According to the present invention, sensing of ventricular events on either channel will trigger execution of state machine in states 1 and 4. During states 2 and 3, R-wave sensing continues but state machine is triggered every predetermined number of seconds, as described below.

Returning to FIG. 7A, a buffer of the most recent 12 R-R intervals obtained during R-wave processing using the sensing scheme of FIG. 8, described above, for example, is independently maintained for each of the two sensing channels ECG1 and ECG2. When the next sensed R-wave is obtained, Block 322, which initially would be the $12^{th}$ R-wave interval, a heart rate estimate is determined, Block 323, using a metric of heart rate, such as the mean, trimmed mean, or median of the RR intervals, for example. According to an embodiment of the present invention, the $9^{th}$ fastest beat of the 12 beats on a beat by beat basis is utilized as the heart rate metric. Using the $9^{th}$ fastest beat provides an estimate of heart rate that is less susceptible to oversensing while maintaining reasonable sensitivity to short R-R intervals as in the case of VT/VF. If the buffer of 12 R-R intervals contains any unknown R-R intervals (i.e., because the buffer is not yet filled) the initial estimate of heart rate is unknown.

Once the heart rate estimate is obtained using the heart rate metric, a determination is made as to whether asystole is detected for either channel, ECG1 or ECG2, Block 324. According to an embodiment of the present invention, asystole is detected for the channel, for example, either by determining whether one of the 12 R-R intervals is greater than a predetermined time period, such as three seconds, for example, or if the time since the most recently sensed R wave exceeds a predetermined time period, such as three seconds, for example. The latter can occur if an R-wave is sensed, for example, in one channel ECG1, but the other channel ECG2 has not had an R-wave sense in three or more seconds. If asystole is detected for either of the two channels ECG1 or ECG2, the current 12 R-R intervals for channels that are determined to be in asystole are cleared from the buffers, Block 325, and the process continues by determining whether the current heart rate estimate is reliable for both channels ECG1 and ECG2, Block 328, described below.

If asystole is not detected for either channel ECG1 and ECG2, NO in Block 324, a determination is made independently for both channels ECG1 and ECG2 as to whether the current heart rate estimate for both channels ECG1 and ECG2 is reliable, Block 328. According to an embodiment of the present invention, the current heart rate estimate for each of the two channels ECG1 and ECG2 is determined not to be reliable, No in Block 328, if either there are unknown or cleared entries in the buffer for that channel, or if a predetermined number of the sensed R-waves associated with the current 12 R-R intervals for that channel was sensed at the minimum sensing threshold level, i.e., the first threshold level 403 of FIG. 8, for example, and if the current heart rate estimate for the channel is less than the programmed heart rate threshold. According to one embodiment, the predetermined number of sensed R-waves that must be sensed at the minimum threshold is set at two, for example. In addition, the programmed heart rate threshold may be within a range of 150 to 240 beats per minute, and is nominally set at 180 beats per minute, for example. It is understood that while the processing is described using a buffer of 12 R-R intervals, any number of intervals and predetermined number of sensed R-waves that must be sensed at the minimum threshold may be utilized.

If the above analysis does not determine that both of the channels are reliable, No in Block 328, a determination is made as to whether just one of the channels was unreliable or if both channels were unreliable, Block 330. If both channels are determined to be unreliable, the current 12 R-R intervals for both channels ECG1 and ECG2 are cleared from the buffers, Block 326, and the next R-sense is obtained for each channel, Block 322 using the sensing scheme of FIG. 8, described above, so that a new heart rate estimate is determined, Block 323, based on the new R-R intervals.

If only one channel is determined to unreliable, the value for the heart rate estimate for both channels is set to the current heart rate estimate for the channel determined to be reliable, Block 332. Once either both channels are determined to be reliable, YES in Block 328, or only one of the two channels is determined to be unreliable and therefore the heart rate estimate for both channels is set to the current heart rate estimate for the channel determined to be reliable, Block 332, the final heart rate estimate is determined for each channel ECG1 and ECG2 based on those results, Block 334, i.e., the heart rate estimate for each channel is set equal to their respective heart rate estimates determined in Block 323, or both are set equal to the heart rate estimate associated with the channel determined to be reliable, Block 332. A determination is then made as to whether the final heart rate estimates for both channels is greater than a predetermined VT/VF threshold, Block 336. According to an embodiment of the present invention, the predetermined VT/VF threshold of Block 336 is set at 180 bpm, for example, although any desired threshold could be utilized.

If the final heart rate estimates for one or both channels is not greater than the predetermined VT/VF threshold, the buffer containing the 12 R-R intervals for the channel not greater than the predetermined VT/VF threshold is updated by removing the first R-sense, shifting the remaining eleven R-sense samples back so that the second R-sense becomes the first R-sense, and so forth, and inserting the next detected R-sense, Block 322, as the twelfth R-sense for each corresponding channel ECG1 and ECG2. A new current heart rate estimate is then determined, Block 323. Once the final heart rate estimates for both channels is greater than the predetermined VT/VF threshold, Yes in Block 336, the process transitions from the not concerned state 302 to the concerned state 304.

According to the present invention, upon transition from the not concerned state 302 to the concerned state 304, Block 305, a most recent window of ECG data from both channels ECG1 and ECG2 are utilized, such as three seconds, for example, so that processing is triggered in the concerned state 304 by a three-second timeout, rather than by the sensing of an R-wave, which is utilized when in the not concerned state 302, described above. It is understood that while the processing is described as being triggered over a three second period, other times periods for the processing time utilized when in the concerned state 304 may be chosen, but should preferably be within a range of 0.5 to 10 seconds. As a result, although sensing of individual R-waves continues to occur in both channels ECG1 and ECG2 when in the concerned state 304, and the buffer of 12 R-R intervals continues to be updated, the opportunities for changing from the concerned state 304 to another state and the estimates of heart rate only occur once the three-second timer expires. Upon initial entry to the concerned state 304, it is advantageous to process the most recent three-seconds of ECG data, i.e., ECG data for the three seconds leading up to the transition to the concerned state 304. This requires a continuous circular buffering of the most recent three seconds of ECG data even while in the not concerned state 302.

Figure 7B:
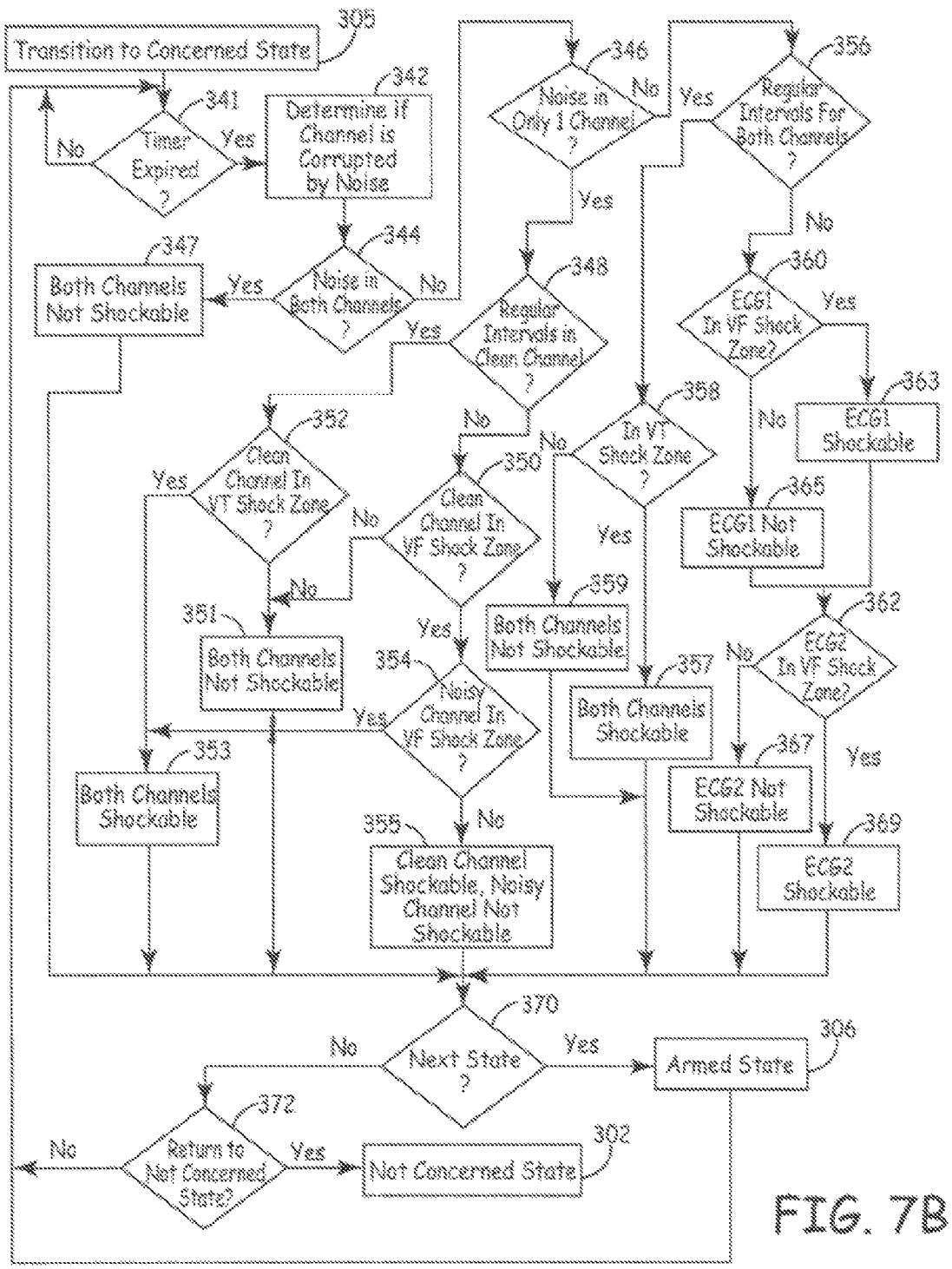

As described in detail below, while in the concerned state 304, the present invention determines how sinusoidal and how noisy the signals are in order to determine the likelihood that a ventricular fibrillation (VF) or fast ventricular tachycardia (VT) event is taking place, since the more sinusoidal and low noise the signal is, the more likely a VT/VF event is taking place. As illustrated in FIG. 7B, once the device transitions from the not concerned state 302 to the concerned state 304, Block 305, a buffer for each of the two channels ECG 1 and ECG2 for storing classifications of 3-second segments of data as "shockable" or "non-shockable" is cleared. Processing of signals of the two channels ECG1 and ECG2 while in the concerned state 304 is then triggered by the three second time period, rather than by the sensing of an R-wave utilized during the not concerned state 302, described above.

Once the three second time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval, a determination is made for each channel ECG1 and ECG 2 as to whether the channel is likely corrupted by noise, Block 342, and a determination is then made as to whether both channels ECG1 and ECG2 are corrupted by noise, Block 344.

Figure 7C:
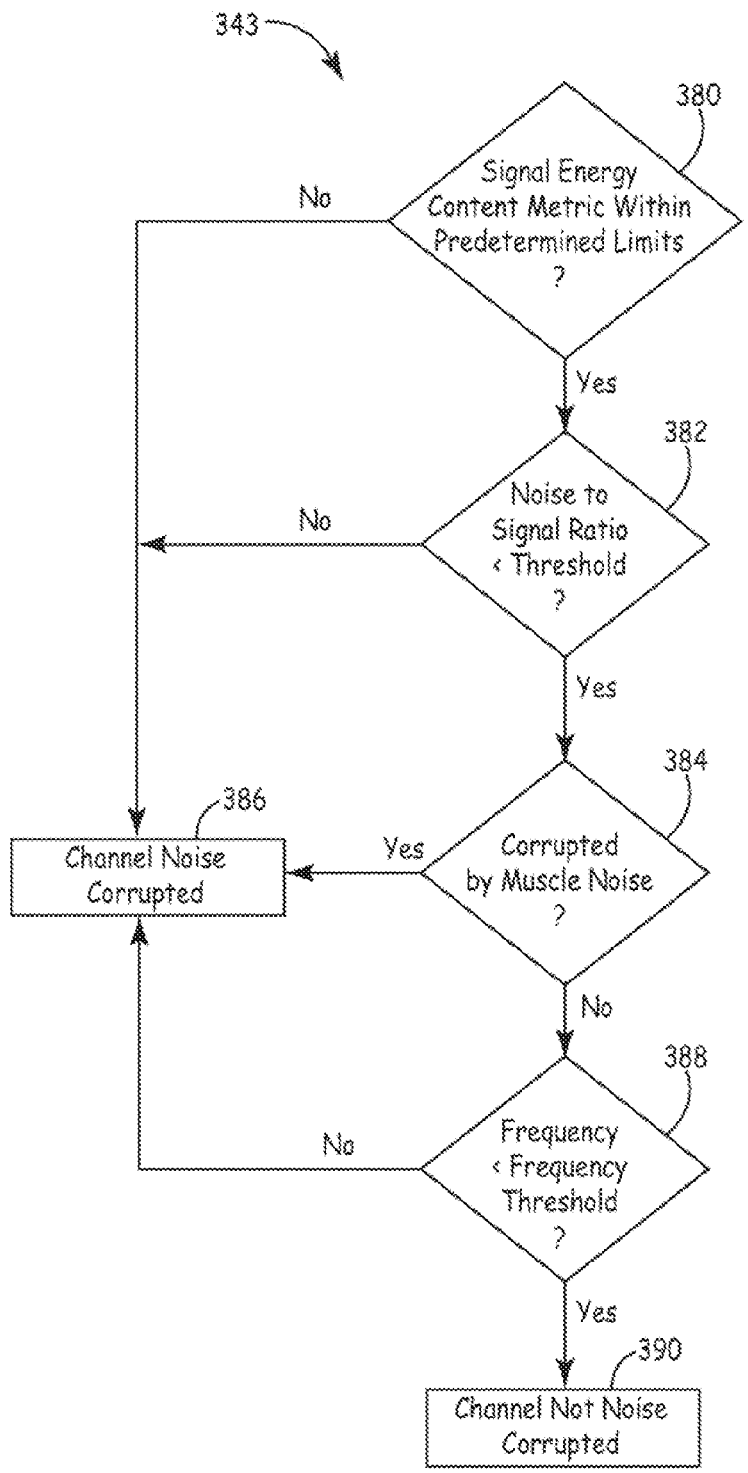

As illustrated in FIG. 7C, the determination as to whether the signal associated with each of the channels ECG1 and ECG2 is likely corrupted by noise, Block 342 of FIG. 7B, includes multiple sequential noise tests that are performed on each channel ECG and ECG2. During a first noise test, for example, a determination is made as to whether a metric of signal energy content of the signal for the channel is within predetermined limits, Block 380. For example, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

Once the mean rectified amplitude is calculated, a determination is made as to whether the mean rectified amplitude is between an upper average amplitude limit and a lower average amplitude limit, the lower average amplitude limit being associated with asystole episodes without artifact and the upper average amplitude limit being associated with a value greater than what would be associated with ventricular tachycardia and ventricular fibrillation events. According to an embodiment of the present invention, the upper average amplitude limit is set as 1.5 mV, and the lower average amplitude limit is set as 0.013 mV. While the metric of signal energy content is described above as the mean rectified amplitude, it is understood that other signal of energy contents could be utilized.

If the determined mean rectified amplitude is not between the upper average amplitude limit and the lower average amplitude limit, the three second segment for that channel is identified as being likely corrupted with noise, Block 386, and no further noise tests are initiated for that channel's segment.

If the determined mean rectified amplitude is located between the upper average amplitude limit and the lower average amplitude limit, a noise to signal ratio is calculated and a determination is made as to whether the noise to signal ratio is less than a predetermined noise to signal threshold, Block 382. For example, the amplitude of each sample associated with the three second window is determined, resulting in N raw sample amplitudes. The raw signal is lowpass filtered, resulting in L lowpass sample amplitudes. The raw mean rectified amplitude is determined as the average of the absolute values of the raw sample amplitudes. The lowpass mean rectified amplitude is determined as the average of the absolute values of the lowpass sample amplitudes. Next, a highpass mean rectified amplitude is then calculated as the difference between the raw mean rectified amplitude and the lowpass mean rectified amplitude. The noise to signal ratio is then determined as the ratio of the highpass mean rectified amplitude to the lowpass mean rectified amplitude. If the noise to signal ratio is greater than a predetermined threshold, such as 0.0703, for example, the three second segment for that channel is identified as being likely corrupted with noise, Block 386, and no further noise tests are initiated for the segment.

If the noise to signal ratio is less than or equal to the predetermined threshold, a determination is made as to whether the signal is corrupted by muscle noise, Block 384. According to an embodiment of the present invention, the determination as to whether the signal is corrupted by muscle noise is made by determining whether the signal includes a predetermined number of signal inflections indicative of the likelihood of the signal being corrupted by muscle noise, using a muscle noise pulse count that is calculated to quantify the number of signal inflections in the three second interval for each channel ECG1 and ECG2. The presence of a significant number of inflections is likely indicative of muscle noise.

Figure 9A:
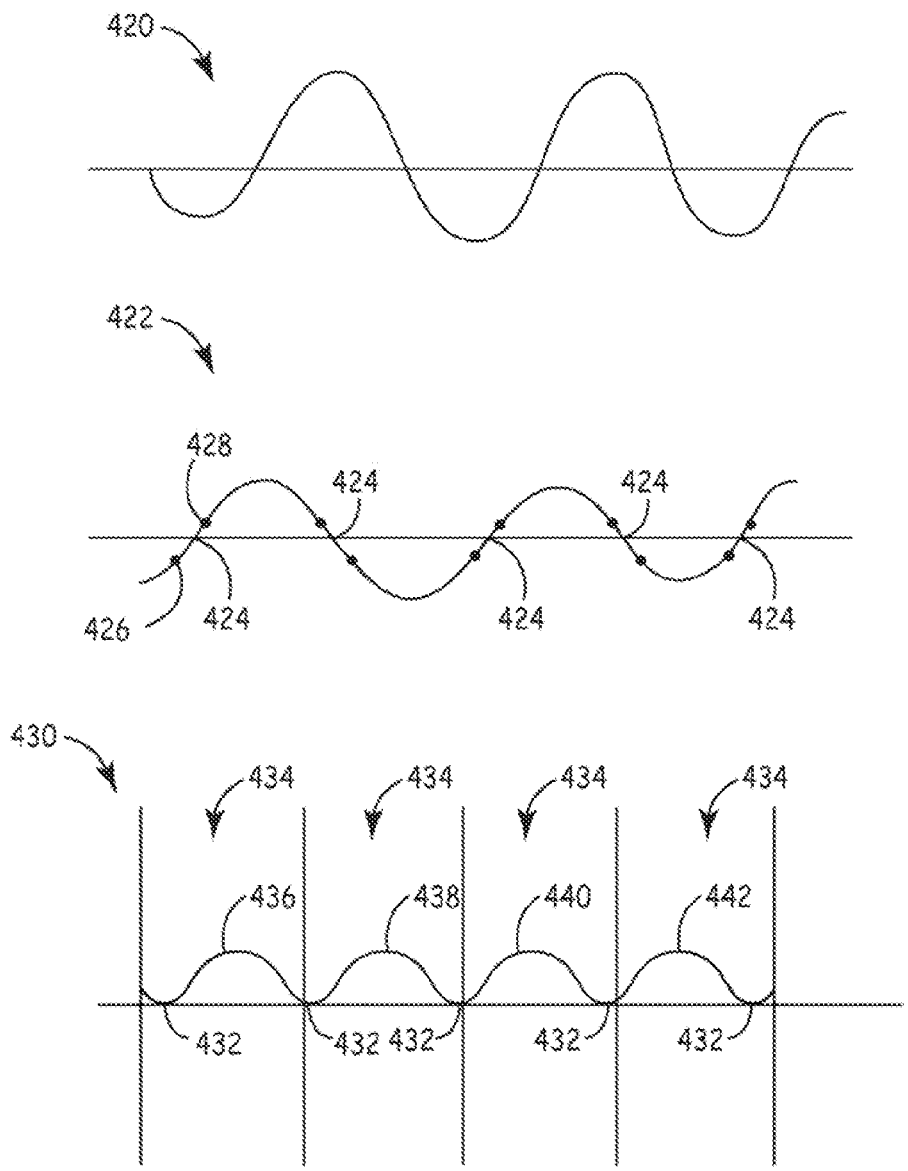
FIG. 9A is a graphical representation of a determination of whether a signal is corrupted by muscle noise according to an embodiment of the present invention.
Figure 9B:
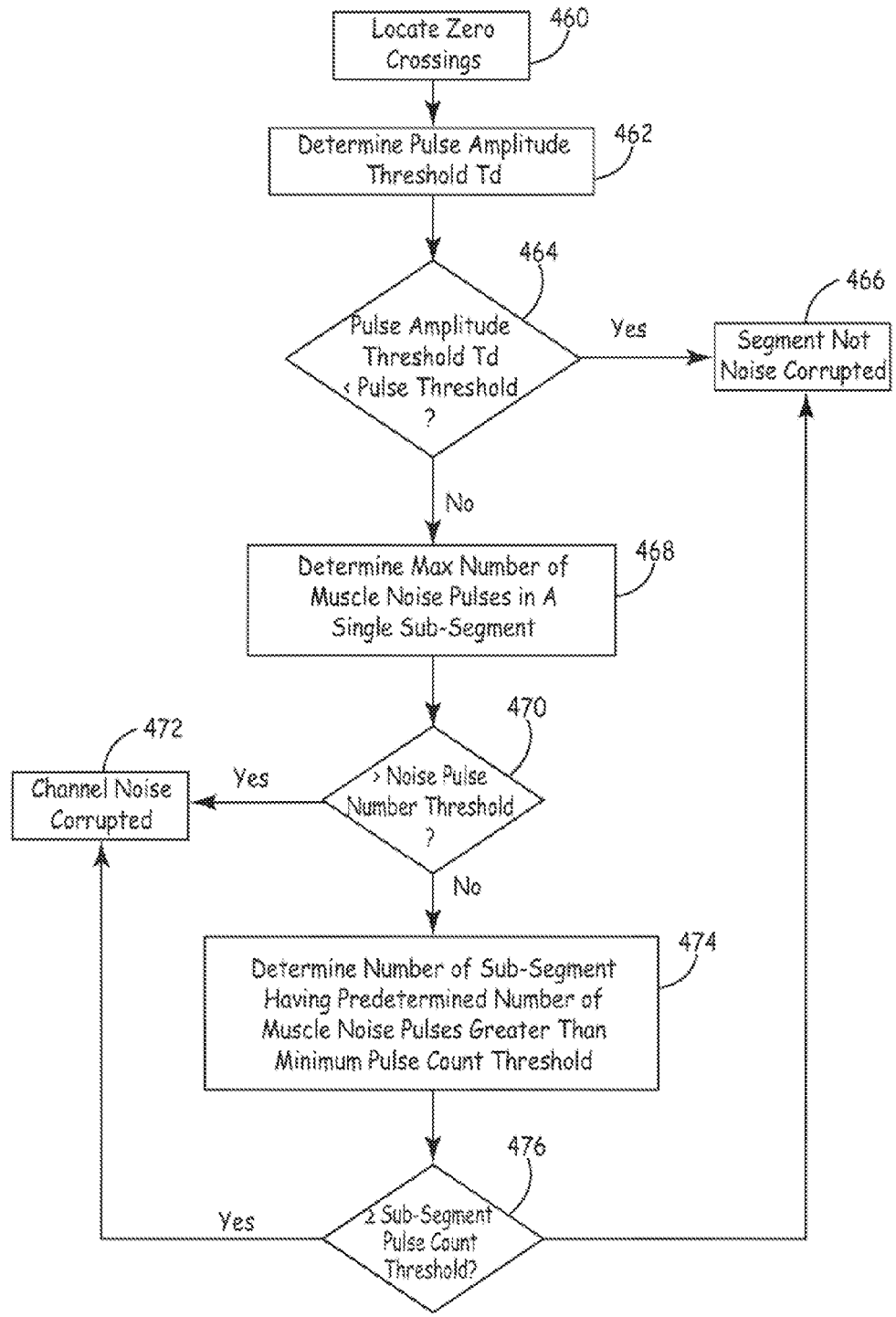
FIG. 9B is a flowchart of a method of determining whether a signal is corrupted by muscle noise according to an embodiment of the present invention.

FIG. 9A is a graphical representation of a determination of whether a signal is corrupted by muscle noise according to an embodiment of the present invention. FIG. 9B is a flowchart of a method of determining whether a signal is corrupted by muscle noise according to an embodiment of the present invention. For example, as illustrated in FIGS. 9A and 9B, in order to determine a muscle noise count for the three second interval, the raw signal 420 is applied to a first order derivative filter to obtain a derivative signal 422, and all of the zero-crossings 424 in the derivative signal 422 are located, Block 460. A data pair corresponding to the data points immediately prior to and subsequent to the zero crossings 424, points 426 and 428 respectively, for each crossing is obtained. The value of the data point in each data pair with smaller absolute value is zeroed in order to allow a clear demarcation of each pulse when a rectified signal 430 is derived from the derivative signal 422 with zeroed zero-crossing points 432.

A pulse amplitude threshold Td, for determining whether the identified inflection is of a significant amplitude to be identified as being associated with muscle noise, is determined, Block 462, by dividing the rectified signal from the three second segment into equal sub-segments 434, estimating a local maximum amplitude 436-442 for each of the sub-segments 434, and determining whether the local amplitudes 436-442 are less than a portion of the maximum amplitude, which is maximum amplitude 440 in the example of FIG. 9, for the whole three second segment. If the local maximum amplitude is less than the portion of the maximum amplitude for the whole three second segment, the local maximum amplitude is replaced by the maximum for the whole three second segment for the sub-segment corresponding to that local maximum amplitude.

It is understood that while only two or less zero-crossing points are shown as being located within the sub-segments in the illustration of FIG. 9 for the sake of simplicity, in fact each of the sub-segments 434, which have a length of approximately 750 milliseconds, will contain many inflections, such as every 25 milliseconds, for example.

According to an embodiment of the present invention, the three second segment is divided into four sub-segments and the local maximum amplitudes are replaced by the maximum amplitude for the whole segment if the local maximum amplitude is less than one fifth of the maximum amplitude for the whole segment. Once the determination of whether to replace the local maximum amplitudes for each of the sub-segments with the maximum amplitude for the whole segment is completed, the pulse amplitude threshold Td for the segment is set equal to a predetermined fraction of the mean of the local maximum amplitudes for each of the sub-segments. According to an embodiment of the present invention, the pulse amplitude threshold Td for the three second segment is set equal to one sixth of the mean of the local maximum amplitudes 436-440.

Once the pulse amplitude threshold Td has been determined, the inflections associated with the signal for the three second segment is classified as being of significant level to be likely indicative of noise by determining whether the pulse amplitude threshold Td is less than a pulse threshold, Block 464. According to an embodiment of the present invention, the pulse threshold is set as 1 microvolt. If the pulse amplitude threshold Td is less than the pulse threshold, the signal strength is too small for a determination of muscle noise, and therefore the signal is determined to be not likely corrupted by noise and therefore the channel is determined to be not noise corrupted, Block 466.

If the pulse amplitude threshold Td is greater than or equal to the pulse threshold, the three second segment is divided into twelve sub-segments of 250 ms window length, the number of muscle noise pulses in each sub-segment is counted, and both the sub-segment having the maximum number of muscle noise pulses and the number of sub-segments having 6 or more muscle noise pulses that are greater than a predetermined minimum threshold is determined. Muscle noise is determined to be present in the signal if either the maximum number of muscle noise pulses in a single sub-segment is greater than a noise pulse number threshold or the number of sub-segments of the twelve sub-segments having 6 or more muscle noise pulses greater than the minimum threshold is greater than or equal to a sub-segment pulse count threshold. According to an embodiment of the present invention, the noise pulse number threshold is set equal to eight and the sub-segment pulse count threshold is set equal to three.

For example, if the pulse amplitude threshold Td is greater than or equal to the pulse threshold, No in Block 464, the maximum number of muscle noise counts in a single sub-segment is determined, Block 468. If the maximum number of muscle noise counts is greater than the noise pulse number threshold, Yes in Block 470, the channel is determined to be noise corrupted, Block 472. If the maximum number of muscle noise counts for the channel is less than or equal to the noise pulse number threshold, No in Block 470, the number of sub-segments of the twelve sub-segments having 6 or more muscle noise pulses greater than the minimum threshold is determined, Block 474, and if the number is greater than or equal to a sub-segment pulse count threshold, Yes in Block 476, the channel is determined to be noise corrupted, Block 472. If the number is less than the sub-segment pulse count threshold, No in Block 476, the channel is determined not to be noise corrupted, Block 466.

Figure 9C:
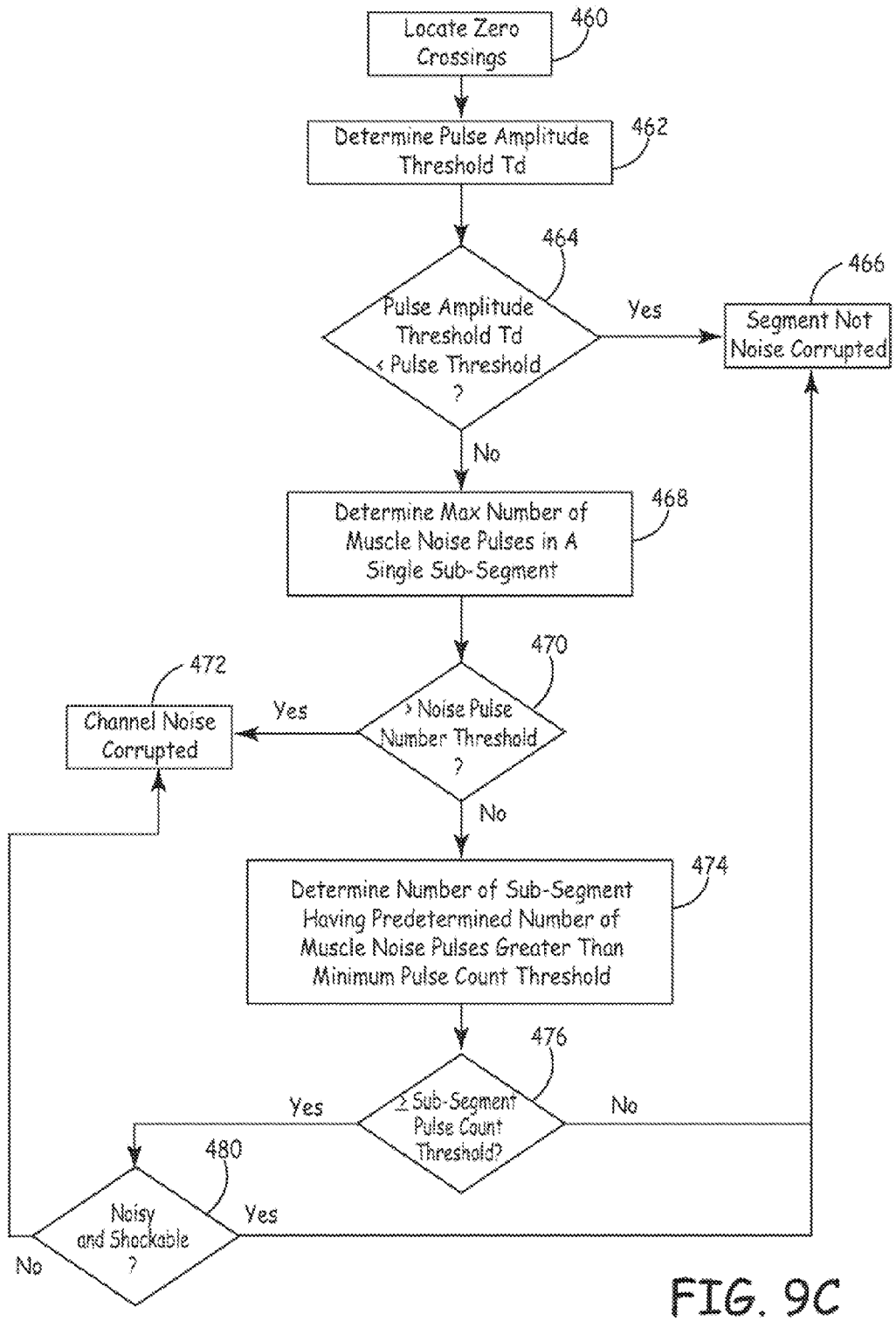
FIG. 9C is a flowchart of a method of determining whether a signal is corrupted by muscle noise according to an embodiment of the present invention.

FIG. 9C is a flowchart of a method of determining whether a signal is corrupted by muscle noise according to an embodiment of the present invention. Since muscle noise can be present during an episode of ventricular tachycardia, the width of the overall signal pulse waveform is determined in order to distinguish between signals that are determined likely to be purely noise related and signals that are both shockable events and determined to include noise. Therefore, as illustrated in FIG. 9C, according to an embodiment of the present invention, once muscle noise is determined to be present as a result of the muscle noise pulse count being satisfied, No in Block 470 and Yes in Block 476, a determination is made as to whether the signal is both noise corrupted and shockable, Block 480.

According to an embodiment of the present invention, the determination in Block 480 as to whether the signal is both noisy and shockable is made, for example, by dividing the rectified signal, having 768 data points, into four sub-segments and determining a maximum amplitude for each of the four sub-segments by determining whether a maximum amplitude for the sub-segment is less than a portion of the maximum amplitude for the entire rectified signal in the three second segment. For example, a determination is made for each sub-segment as to whether the maximum amplitude for the sub-segment is less than one fourth of the maximum amplitude for the entire rectified signal. If less than a portion of the maximum amplitude for the entire rectified signal in the three second segment, the maximum amplitude for the sub-segment is set equal to the maximum amplitude for the entire rectified signal.

A mean rectified amplitude for each of the sub-segments is determined by dividing the sum of the rectified amplitudes for the sub-segment by the number of samples in the sub-segment, i.e., 768÷4. Then the normalized mean rectified amplitude for each sub-segment is determined by dividing the mean rectified amplitude for each of the sub-segments by the peak amplitude for the sub-segment. The normalized mean rectified amplitude for the three second segment is then determined as the sum of the normalized mean rectified amplitudes for each sub-segment divided by the number of sub-segments, i.e., four.

Therefore, once muscle noise is suspected as a result of the determination of the muscle noise pulse count, the determination of Block 480 based on whether the normalized mean rectified amplitude for the three second segment is greater than a predetermined threshold for identifying signals that, despite being indicative of a likelihood of being associated with noise, nevertheless are associated with a shockable event. For example, according to an embodiment of the present invention, a determination is made as to whether the normalized mean rectified amplitude for the three second segment is greater than 18 microvolts. If the normalized mean rectified amplitude for the three second segment is less than or equal to the predetermined threshold, the channel is likely corrupted by muscle noise and not shockable, No in Block 480, and is therefore identified as being corrupted by noise, Block 472. If the normalized mean rectified amplitude for the three second segment is greater than the predetermined threshold, the channel is determined to be likely corrupted by muscle noise and shockable, Yes in Block 480, and is therefore identified as not to be likely corrupted by muscle noise, Block 478.

Returning to FIG. 7C, when the signal is determined to be not likely corrupted by muscle noise, a determination is made as to whether the mean frequency of the signal associated with the channel is less than a predetermined mean frequency threshold, Block 388, such as 11 Hz for example. The mean frequency of the signal during the 3 second segment for each channel ECG 1 and ECG2 is generated, for example, by calculating the ratio of the mean absolute amplitude of the first derivative of the 3 second segment to the mean absolute amplitude of the 3 second segment, multiplied by a constant scaling factor. If the mean frequency is determined to be greater than or equal to the predetermined mean frequency threshold, No in Block 388, the three second segment for that channel is identified as being likely corrupted with noise, Block 386. If the mean frequency is determined to be less than the predetermined mean frequency threshold, Yes in Block 388, the three second segment for that channel is identified as being not noise corrupted, Block 390.

According to an embodiment of the present invention, since the mean spectral frequency tends to be low for true ventricular fibrillation events, moderate for organized rhythms such as sinus rhythm and supraventricular tachycardia, for example, and high during asystole and noise, the determination in Block 388 includes determining whether the mean frequency is less than a predetermined upper mean frequency threshold, such as 11 Hz (i.e., mean period T of approximately 91 milliseconds) for example, and whether the mean frequency is less than a predetermined lower mean frequency, such as 3 Hz for example. If the mean frequency is below a second, lower threshold, such as 3 Hz, for example, the signal is also rejected as noise and no further noise tests are initiated. This comparison of the mean frequency to a second lower threshold is intended to identify instances of oversensing, resulting in appropriate transition to the concerned state. If the mean frequency of the signal is less than 3 Hz, it is generally not possible for the heart rate to be greater than 180 beats per minute. In practice, it may be advantageous to set the lower frequency threshold equal to the programmed VT/VF detection rate, which is typically approximately 3 Hz.

Therefore, in the determination of Block 388, if the mean frequency is determined to be either greater than or equal to the predetermined upper mean frequency threshold or less than the lower threshold, the three second segment for that channel is identified as being likely corrupted with noise, Block 386. If the mean frequency is determined to be both less than the predetermined upper mean frequency threshold and greater than the lower threshold, the three second segment for that channel is identified as not being noise corrupted, Block 390.

Returning to FIG. 7B, once the determination as to whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG 2 containing the last three classifications of the channel is updated accordingly. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone, Block 352.

Figure 7D:
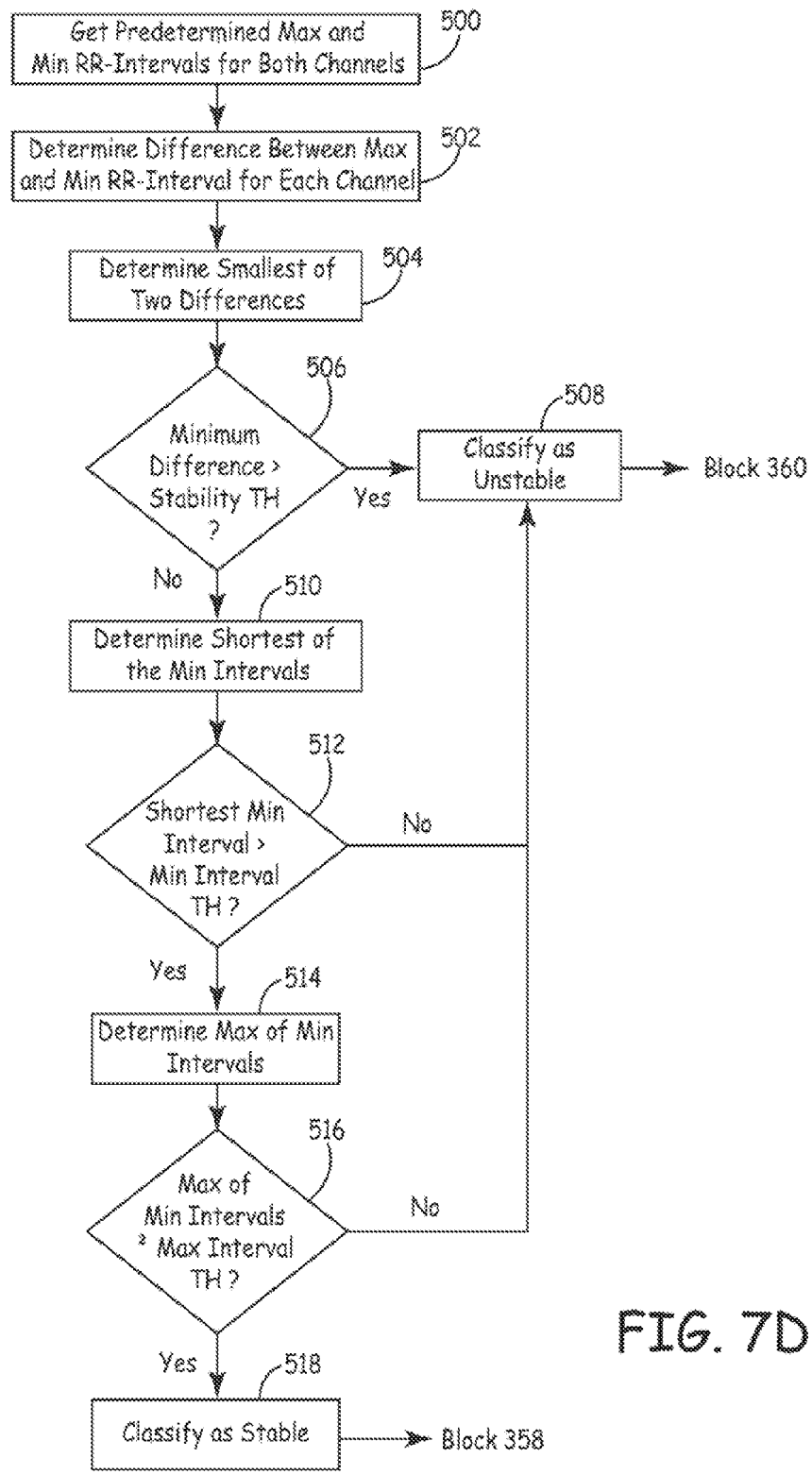

As illustrated in FIG. 7D, according to an embodiment of the present invention, in order to determine whether the signal for both channels includes R-R intervals that are regular and the channels can be therefore classified as being relatively stable, Block 356, predetermined maximum and minimum intervals for each channel ECG1 and ECG2 are identified, Block 500, from the updated buffer of 12 RR-intervals, Block 342. According to one embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated for each channel ECG1 and ECG2, Block 502, to generate a first interval difference associated with the first channel ECG1 and a second interval difference associated with the second channel ECG2. The smallest of the first interval difference and the second interval difference is then identified, Block 504, and a determination is made as to whether the minimum of the first interval difference and the second interval difference is greater than a predetermined stability threshold, Block 506, such as 110 milliseconds, for example.

If the minimum of the first interval difference and the second interval difference is greater than the stability threshold, the event is classified as an unstable event, Block 508, and a determination is made for each channel as to whether the signal associated with the channel is within a predetermined VF shock zone, Blocks 360 and 362 of FIG. 7B, described below. If the minimum of the first interval difference and the second interval difference is less than or equal to the stability threshold, No in Block 506, the device determines which one of the minimum RR-interval associated with the first channel ECG1 and the minimum RR-interval associated with the second channel ECG2 is shortest, Block 510, and determines whether the shortest minimum interval is greater than a minimum interval threshold, Block 512, such as 200 milliseconds, for example.

If the shortest of the two minimum intervals is less than or equal to the minimum interval threshold, the event is classified as an unstable event, Block 508, and a determination is made for each channel as to whether the signal associated with the channel is within a predetermined VF shock zone, Blocks 360 and 362 of FIG. 7B, described below. If the shortest of the two minimum intervals is greater than the minimum interval threshold, the device determines which one of the minimum RR-interval associated with the first channel ECG1 and the minimum RR-interval associated with the second channel ECG2 is the greatest, Block 514, and determines whether the maximum of the two minimum intervals is less than or equal to a maximum interval threshold, Block 516, such as 333 milliseconds for example. If the maximum of the two minimum intervals is greater than the maximum interval threshold, the event is classified as an unstable event, Block 508, and a determination is made for each channel as to whether the signal associated with the channel is within a predetermined VF shock zone, Blocks 360 and 362 of FIG. 7B, described below. If the maximum of the two minimum intervals is less than or equal to the maximum interval threshold, the event is classified as a stable event, Block 518, and a determination is made, based on both channels ECG1 and ECG2, as to whether the signal is within a predetermined VT shock zone, Block 358, described below.

Figure 7E:
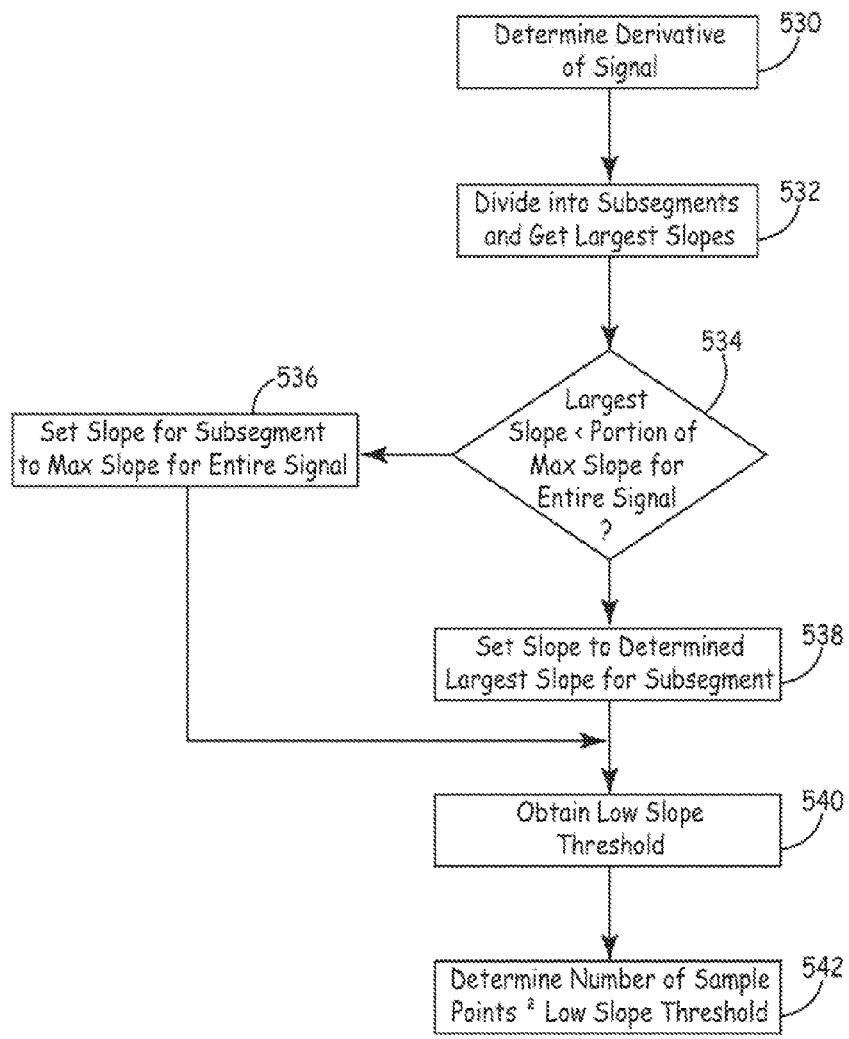

Returning to FIG. 7B, according to an embodiment of the present invention, during the determination of whether the signal associated with each of the channels ECG1 and ECG2 is within the VF shock zone, Blocks 360 and 362, the VF shock zone is defined based upon a low slope content metric and a spectral width metric for each of the two channels ECG1 and ECG2. The low slope content metric is calculated as the ratio of the number of data points with low slope to the total number of samples in the 3-second segment. For example, according to an embodiment of the present invention, the difference between successive ECG samples is determined as an approximation of the first derivative (i.e, the slope) of the ECG signal. In particular, as illustrated in FIG. 7E, the raw signal for each channel is applied to a first order derivative filter to obtain a derivative signal for the three-second segment, Block 530. The derivative signal is then rectified, divided into four equal sub-segments, and the largest absolute slope is estimated for each of the four sub-segments, Block 532.

A determination is made as to whether the largest absolute slopes are less than a portion of the overall largest absolute slope for the whole three-second segment, Block 534, such as one-fifth of the overall absolute slope, for example. If the largest absolute slope is less than the portion of the overall slope, then the slope value for that sub-segment is set equal to the overall largest absolute slope, Block 536. If the largest absolute slope is not less than the portion of the overall slope, then the slope value for that sub-segment is set equal to the determined largest absolute slope for the sub-segment, Block 538.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold, Block 540. The low slope content is then obtained by determining the number of sample points in the three-second segment having an absolute slope less than or equal to the low slope threshold, Block 542.

According to an embodiment of the present invention, if, during the determination of the low slope threshold in Block 540, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

The spectral width metric, which corresponds to an estimate of the spectral width of the signal for the three-second segment associated with each channel ECG1 and ECG2, is defined, for example, as the difference between the mean frequency and the fundamental frequency of the signal. According to an embodiment of the present invention, the spectral width metric is calculated by determining the difference between the most recent estimate of the RR-cycle length and the mean spectral period of the signal for that channel. As is known in the art, the mean spectral period is the inverse of the mean spectral frequency.

It is understood that R-R cycle length utilized in the concerned state and armed state can be different than that used in the not concerned state. For example, according to an embodiment of the present invention, the $9^{th}$ longest R-R interval is utilized in the not concerned state and the mean of the $7^{th}$ to the $10^{th}$ R-R interval is utilized in the concerned state and the armed state.

Figure 10:
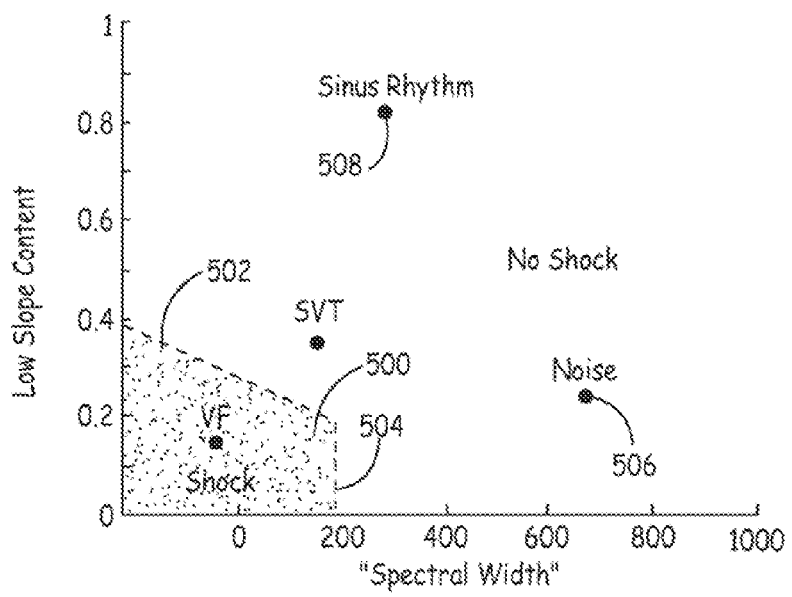
FIG. 10 is a graphical representation of a VF shock zone according to an embodiment of the present invention.

FIG. 10 is a graphical representation of a VF shock zone according to an embodiment of the present invention. As illustrated in FIG. 10, a VF shock zone 500 is defined for each channel ECG1 and ECG2 based on the relationship between the calculated low slope content and the spectral width associated with the channel. For example, the shock zone is defined by a first boundary 502 associated with the low slope content set for by the equation:

$$\text{Low slope content} = -0.0013 \times \text{spectral width} + 0.415 \quad \text{Equation 1}$$

and a second boundary 504 associated with the spectral width set forth by the equation:

$$\text{spectral width} = 200 \quad \text{Equation 2}$$

As can be seen in FIG. 10, since noise 506 tends to have a relatively higher spectral width, and normal sinus rhythm 508 tends to have a relatively higher low slope content relative to VF, both noise 506 and normal sinus rhythm 508 would be located outside the VF shock zone 500.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

According to an embodiment of the present invention, rather than being defined by Equation 1, the shock zone may be defined so that the first boundary 502 associated with the low slope content is set forth by the following equation:

$$\text{Low slope content} = -0.005 \times \text{spectral width} + 1.1 \quad \text{Equation 1A}$$

so that the VF shock zone 500 is defined, as described above, using Equation 1A and Equation 2.

Figure 11A:
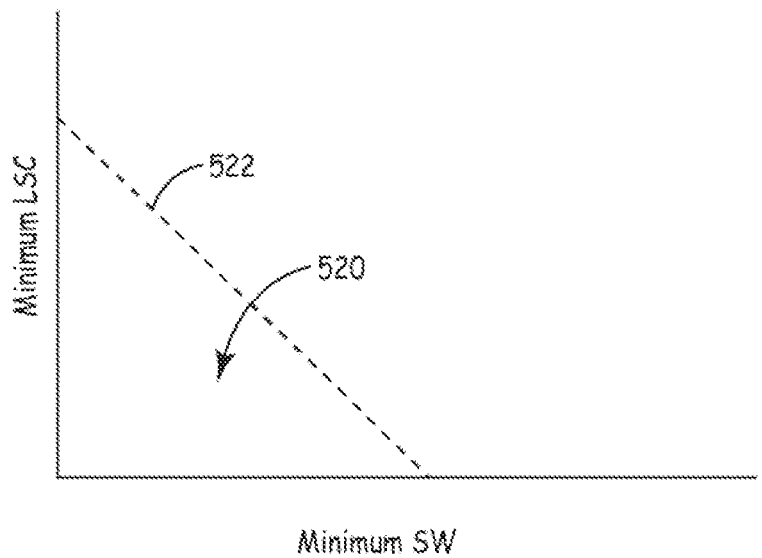
FIGS. 11A and 11B are graphical representations of the determination of whether an event is within a shock zone according to an embodiment of the present invention.
Figure 11B:
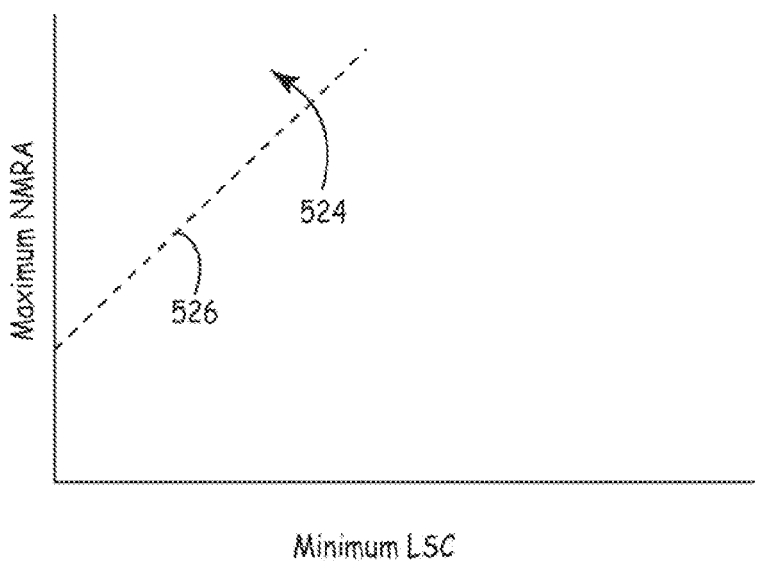

FIGS. 11A and 11B are graphical representations of the determination of whether an event is within a shock zone according to an embodiment of the present invention. During the determination of whether the event is within the VT shock zone, Block 358 of FIG. 7B, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG 1 and ECG2 contains the minimum spectral width. A first VT shock zone 520 is defined based on the relationship between the low slope content associated with the channel determined to have the minimum low slope content and the spectral width associated with the channel determined to have the minimum spectral width. For example, according to an embodiment of the present invention, the first VT shock zone 520 is defined by a boundary 522 associated with the minimum low slope content and the minimum spectral width set forth by the equation:

$$LSC = -0.004 \times SW + 0.93 \quad \text{Equation 3}$$

A second VT shock zone 524 is defined based on the relationship between the low slope content associated with the channel determined to have the minimum low slope content and the normalized mean rectified amplitude associated with the channel determined to have the maximum normalized mean rectified amplitude. The normalized mean rectified amplitudes for the two channels ECG1 and ECG2 utilized during the VT shock zone test is the same as described above in reference to the noise determination of Block 343. For example, according to an embodiment of the present invention, the second VT shock zone 524 is defined by a second boundary 526 associated with the relationship between the minimum low slope count and the maximum normalized mean rectified amplitude set forth by the equation:

$$NMRA = 68 \times LSC + 8.16 \quad \text{Equation 4}$$

If both the minimum low slope count is less than the first boundary 522, i.e., −0.004×minimum spectral width+0.93, and the maximum normalized mean rectified amplitude is greater than the second boundary 526, i.e., 68×minimum low slope count+8.16, the event is determined to be in the VT shock zone, YES in Block 358, and both channels ECG1 and ECG2 are determined to be shockable, Block 357, and the associated buffers are updated accordingly. If either the minimum low slope count is not less than the first boundary 522 or the maximum normalized mean rectified amplitude is not greater than the second boundary 526, the event is determined to be outside the VT shock zone, NO in Block 358, and both channels ECG1 and ECG2 are determined to be not shockable, Block 359.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

Figure 7F:
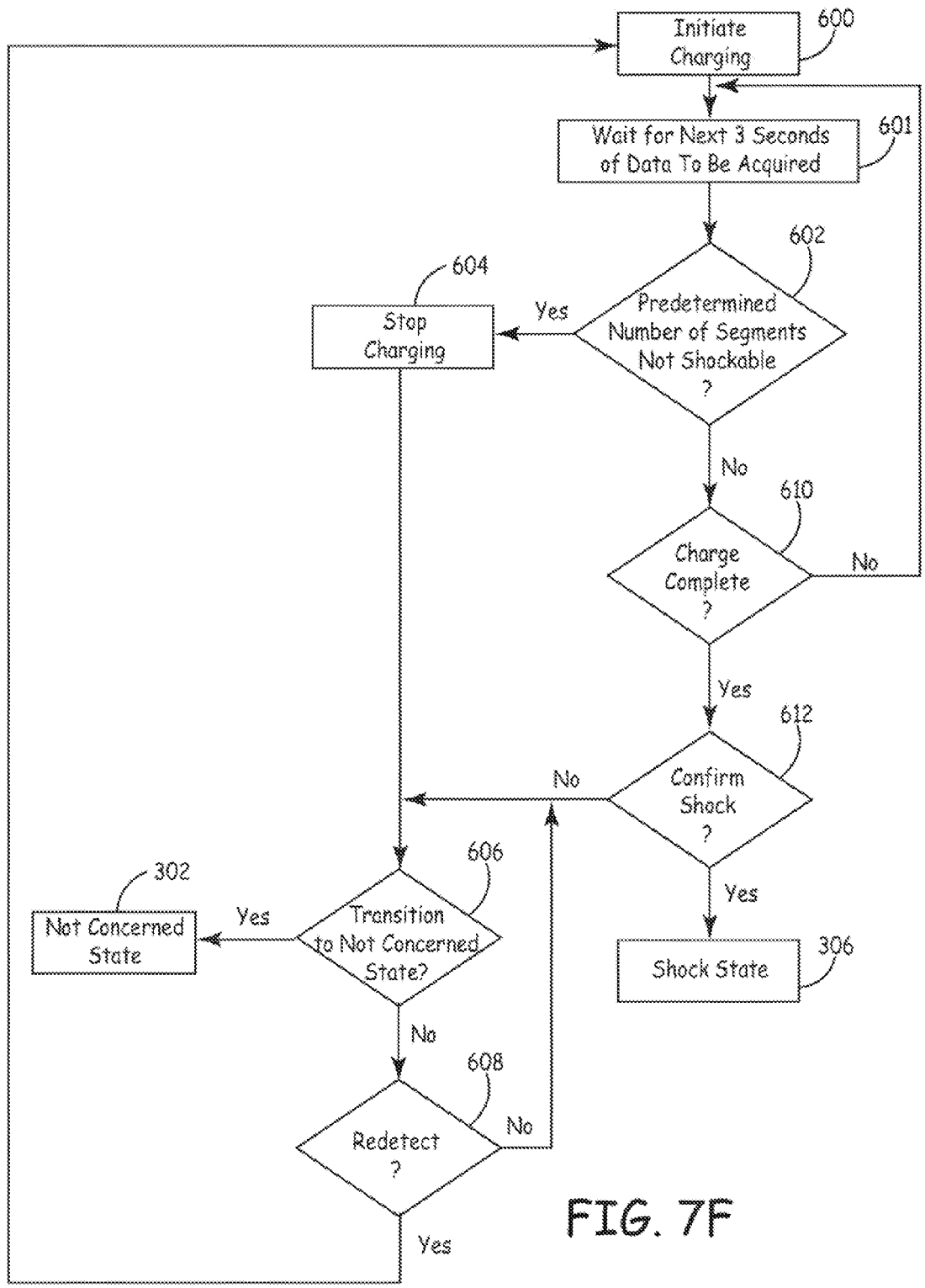

According to an embodiment of the present invention, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular. For example, as illustrated in FIG. 7H, predetermined maximum and minimum intervals for the clean channel are identified, Block 700, from the updated buffer of 12 RR-intervals, Block

342 of FIG. 7B. According to an embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel, 702. A determination is then made as to whether the interval difference is greater than a predetermined stability threshold, Block 704, such as 110 milliseconds, for example.

If the interval difference is greater than the stability threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the interval difference is less than or equal to the stability threshold, No in Block 704, the device determines whether the minimum RR interval is greater than a minimum interval threshold, Block 710, such as 200 milliseconds, for example.

If the minimum interval is less than or equal to the minimum interval threshold, No in Block 710, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the minimum interval is greater than the minimum interval threshold, Yes in Block 710, the device determines whether the maximum interval is less than or equal to a maximum interval threshold, Block 712, such as 333 milliseconds for example. If the maximum interval is greater than the maximum interval threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the maximum interval is less than or equal to the maximum interval threshold, the event is classified as a stable event, Block 714, and therefore the clean channel is determined to include regular intervals, Yes in Block 348, and a determination is made as to whether the signal associated with the clean channel is within a predetermined VT shock zone, Block 352 of FIG. 7B, described below.

Returning to FIG. 7B, according to an embodiment of the present invention, the determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the clean channel, the determination of whether the clean channel is in the VF shock zone is made using Equations 1 and 2, so that if either the low slope content for the clean channel is not less than the first boundary 502 or the spectral width is not less than the second boundary 504, the clean channel is determined not to be in the VF zone, No in Block 350 and both channels are classified as not shockable, Block 351, and the associated buffers are updated accordingly.

If the low slope content for the clean channel is less than the first boundary 502 and the spectral width is less than the second boundary 504, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary 502 or the spectral width is not less than the second boundary 504, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary 502 and the spectral width is less than the second boundary 504, the noisy channel is determined to be in the VF zone, Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone 520 is defined based on the relationship between the low slope content and the spectral width associated with the clean channel according to Equation 3, for example, and the second VT shock zone 524 is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present invention, the second VT shock zone 524 is defined by a second boundary 526 associated with the relationship between the low slope count and the normalized mean rectified amplitude of the clean channel using Equation 4.

If both the low slope count is less than the first boundary 522, i.e., −0.004×spectral width of clean channel+0.93, and the normalized mean rectified amplitude is greater than the second boundary 526, i.e., 68×low slope count of clean channel+8.16, the clean channel is determined to be in the VT shock zone, Yes in Block 352, both channels are classified as being shockable, Block 353, and the associated buffers are updated accordingly.

If either the low slope count is not less than the first boundary 522 or the maximum normalized mean rectified amplitude is not greater than the second boundary 526, the clean channel is determined to be outside the VT shock zone, No in Block 352, both channels are classified as being not shockable, Block Block 351, and the associated buffers are updated accordingly.

Figure 12:
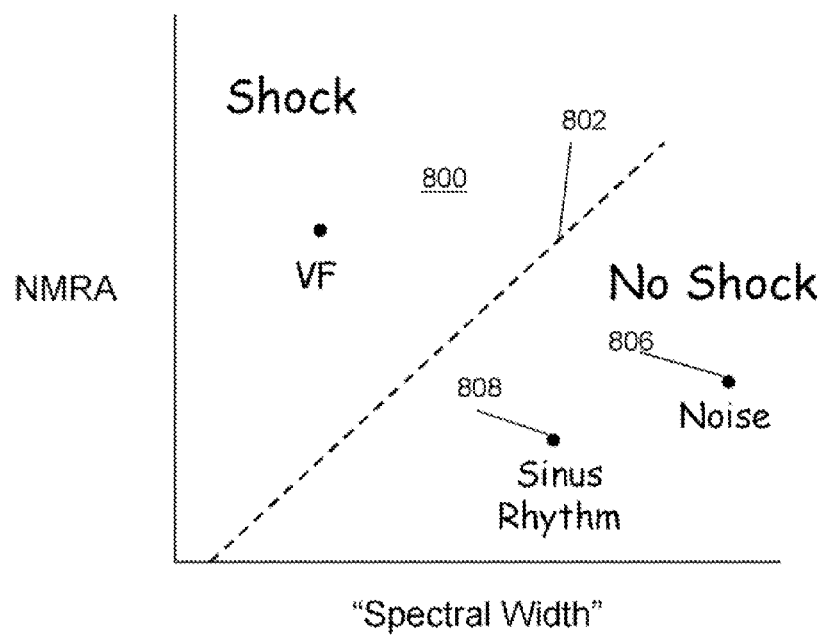
FIG. 12 is a graphical representation of a shock zone according to an embodiment of the present invention.

FIG. 12 is a graphical representation of a shock zone according to an embodiment of the present invention. According to an embodiment of the present invention, during the determination of whether the signal associated with each of the channels ECG1 and ECG2 is within the VF shock zone, Blocks 360 and 362, the VF shock zone is defined based upon a normalized mean rectified amplitude metric and a spectral width metric for each of the two channels ECG1 and ECG2, both of which may be generated, for example, as described above. In particular, according to the embodiment of FIG. 12, a VF shock zone 800 is defined for each channel ECG1 and ECG2, during a given three second sensing window, based on the relationship between the calculated normalized mean rectified amplitude and the spectral width associated with the channel, with the shock zone 800 being defined by a boundary 802 associated with the normalized mean rectified amplitude by the equation:

$$\text{Normalized Mean Rectified Amplitude} = 0.2 \times \text{spectral width} + 3 \quad \text{Equation. 5}$$

As can be seen in FIG. 12, since noise 806 tends to have a relatively higher spectral width, and normal sinus rhythm 808 tends to have a relatively lower normalized mean rectified amplitude relative to VF, both noise 806 and normal sinus rhythm 808 are located outside the VF shock zone 800. Therefore, a determination is made for each channel ECG1 and ECG2, during a given three second sensing window, as to whether the normalized mean rectified amplitude for that channel is greater than or equal to the boundary 802, i.e., the normalized mean rectified amplitude is greater than or equal to 0.2×spectral width+3. For example, once the event is determined to be associated with VF, i.e., the intervals for both channels are determined to be irregular, No in Block 356, a determination is made that channel ECG1 is in the VF shock zone, Yes in Block 360, if, for channel ECG1, the normalized mean rectified amplitude is greater than or equal to the boundary 802. The three second segment for that channel ECG1 is then determined to be shockable, Block 363 and the associated buffer for that channel is updated accordingly. If the normalized mean rectified amplitude for the channel is less than the boundary 802, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, the normalized mean rectified amplitude is greater than or equal to the boundary 802. The three second segment for that channel ECG2 is then determined to be shockable, Block 369 and the associated buffer for that channel is updated accordingly. If the normalized mean rectified amplitude for the channel is less than the boundary 802, the channel ECG2 is determined not to be in the VF shock zone, No in Block 362, the three second segment for that channel ECG2 is then determined to be not shockable, Block 367, and the associated buffer is updated accordingly.

Figure 13:
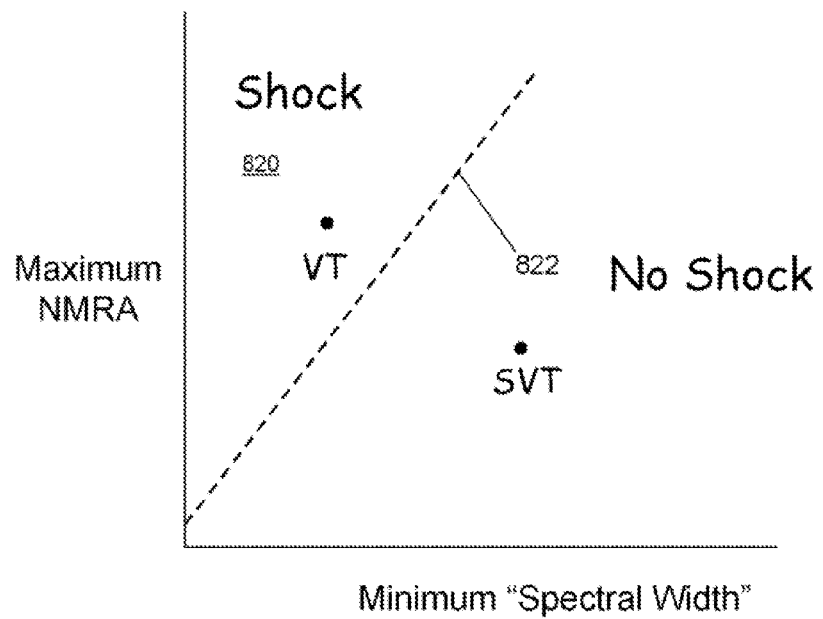
FIG. 13 is a graphical representation of the determination of whether an event is within a shock zone according to an embodiment of the present invention.

FIG. 13 is a graphical representation of the determination of whether an event is within a shock zone according to an embodiment of the present invention. According to another embodiment of the present invention, during the determination of whether the event is within the VT shock zone, Block 358 of FIG. 7B, the normalized mean rectified amplitude and the spectral width are determined for each channel ECG1 and ECG2 during a given three second sensing window, as described above in reference to determining the VF shock zone. A determination is made as to which channel of the two signal channels ECG1 and ECG2 contains the maximum normalized mean rectified amplitude and which channel of the two signal channels ECG 1 and ECG2 contains the minimum spectral width. A VT shock zone 820 is defined based on the relationship between the normalized mean rectified amplitude associated with the channel determined to have the maximum normalized mean rectified amplitude and the spectral width associated with the channel determined to have the minimum spectral width. For example, according to an embodiment of the present invention, the VT shock zone 820 is defined, for a given three second sensing window, by a boundary 822 associated with the maximum normalized mean rectified amplitude and the minimum spectral width set forth by the equation:

$$NMRA = 0.3636 \times SW - 15 \quad \text{Equation 6}$$

If the maximum normalized mean rectified amplitude is greater than or equal to the boundary 822, i.e., 0.3636×minimum spectral width−15, the event is determined to be in the VT shock zone, YES in Block 358, and the three second segment for both channels ECG1 and ECG2 are determined to be shockable, Block 357, and the associated buffers are updated accordingly. If the maximum normalized mean rectified amplitude is less than the boundary 822, the event is determined to be outside the VT shock zone, NO in Block 358, and both channels ECG1 and ECG2 are determined to be not shockable, Block 359.

Returning to FIG. 7B, according to another embodiment of the present invention, the determination of whether the clean channel is within the VF shock zone, Block 350, is made based upon a normalized mean rectified amplitude metric and a spectral width metric, similar to the VF shock zone determination described above in reference to Blocks 360 and 362, both of which are determined for the clean channel using the VF shock zone described above in reference to FIG. 12. In particular, once the normalized mean rectified amplitude metric and a spectral width metric are determined for the clean channel, the determination of whether the clean channel is in the VF shock zone is made using Equation 5, so that if the normalized mean rectified amplitude for the clean channel is less than the boundary 802, the clean channel is determined not to be in the VF zone, No in Block 350 and both channels are classified as not shockable, Block 351, and the associated buffers are updated accordingly.

If the normalized mean rectified amplitude for the clean channel is greater than or equal to the boundary 802, the clean channel is determined to be in the VF zone, Yes in Block 350. A determination is then made as to whether the channel determined to be corrupted by noise, i.e., the "noisy channel", is within the VF shock zone, Block 354. If the normalized mean rectified amplitude for the noisy channel is less than the boundary 802, the noisy channel is determined not to be in the VF zone, No in Block 354, the clean channel is classified as shockable and the noisy channel is classified as not shockable, Block 355, and the associated buffers are updated accordingly.

If the normalized mean rectified amplitude for the noisy channel is greater than or equal to the boundary 802, the noisy channel is determined to be in the VF zone, Yes in Block 354, both the clean channel and the noisy channel are classified as being shockable, Block 353, and the associated buffers are updated accordingly.

Similar to the VT shock zone determination described above in Block 358 using the VT shock zone of FIG. 13, during the determination as to whether the clean channel is within the VT shock zone in Block 352, the normalized mean rectified amplitude and the spectral width are determined for the clean channel as described above in reference to determining the VF shock zone. The VT shock zone 820 is then defined based on the relationship between the normalized mean rectified amplitude and the spectral width associated with the clean channel according to Equation 6. If the maximum normalized mean rectified amplitude for the clean channel is greater than or equal to the boundary 822, i.e., 0.3636× minimum spectral width−15, the clean channel is determined to be in the VT shock zone, YES in Block 352, and both channels ECG1 and ECG2 are determined to be shockable, Block 353, and the associated buffers are updated accordingly. If the maximum normalized mean rectified amplitude for the clean channel is less than the boundary 822, the clean channel is determined to be outside the VT shock zone, NO in Block 352, and both channels ECG1 and ECG2 are determined to be not shockable, Block 351.

Once the classification of both of the channels ECG1 and ECG2 is made subsequent to the determination of whether the clean channel or channels is in the VT shock zone, Block 352 and 358, or the VF shock zone, Blocks 350 and Blocks 360 and 362 in combination, a determination is made as to whether the device should transition from the concerned state 304 to the armed state 306, Block 370. For example, according to an embodiment of the present invention, the transition from the concerned state 304 to the armed state 306 is confirmed if a predetermined number, such as two out of three for example, of three-second segments for both channels ECG1 and ECG2 have been classified as being shockable. If the predetermined number of three-second segments in both channels ECG1 and ECG2 have been classified as shockable, the device transitions from the concerned state 304 to the armed state 306, Yes in Block 370. If the predetermined number of three-second segments in both channels ECG1 and ECG2 have not been classified as shockable, the device does not transition from the concerned state 304 to the armed state 306, no in Block 370, and a determination as to whether to transition back to the not concerned state 302 is made, Block 372. The determination as to whether to transition from the concerned state 304 back to the not concerned state 302 is made, for example, by determining whether the heart rate estimate is less than a heart rate threshold level in both of the two channels ECG1 and ECG2. If it is determined that the device should not transition to the not concerned state 302, i.e., both of the two heart rate estimates are greater than the heart rate threshold, the process is repeated using the signal generated during a next three-second window, Block 341.

According to an embodiment of the present invention, the heart rate threshold level is set as 180 bpm, for example, and a single estimate of heart rate (that occurs every three seconds) in at least one of the two channels ECG1 and ECG2 that is less than the heart rate threshold level will suffice to cause the device to transition from the concerned state 304 to the not concerned state 302, Yes in Block 372.

When the device transitions from the concerned state 304 to the armed state 306, Yes in Block 370, processing continues to be triggered by a three-second time out as is utilized during the concerned state 304, described above. As illustrated in FIG. 7F, once the device transitions from the concerned state 302 to the armed state 306, charging of the capacitors is initiated, Block 600. During the charging of the capacitors, the classification of segments for each channel ECG1 and ECG2 as being either shockable or not shockable generated during the shock zone tests described above continues and once the next three seconds of data has been acquired, Block 601, a determination is made as whether the event continues to be a shockable event by determining whether a predetermined number of segments, such as the most recent two segments for example, have been classified in both of the two channels ECG1 and ECG2 as not shockable, Block 602. If the predetermined number of three second segments have been classified as not shockable, indicating that the event may possibly no longer be a shockable event, Yes in Block 602, the charging of the capacitors is stopped, Block 604, and a determination is made as to whether to transition to the not concerned state 302, Block 606.

According to an embodiment of the present invention, the device will transition from the armed state 306 to the not concerned state 302, Yes in Block 606, if certain termination requirements are met. For example, return to the not concerned state 302 occurs if, for both channels ECG1 and ECG2 simultaneously, less than two out of the last three three-second segments are classified as shockable, less than three out of the last eight three-second segments are classified as shockable, and the most recent three second segment is classified as not shockable. Another possible criteria for returning to the not concerned state 302 is the observation of 4 consecutive not shockable classifications in both channel ECG1 and ECG2 simultaneously.

In addition to the two criteria described above, at least one of the current heart rate estimates must be slower than the programmed rate threshold 403, and capacitor charging must not in progress. If each of these requirements are satisfied, Yes in Block 606, the device transitions from the armed state 306 to the not concerned state 302.

If one or more of these requirements are determined not to be satisfied, return to the not concerned state is not indicated, No in Block 606, and a determination is then made as whether the shockable rhythm is redetected, Block 608, by determining whether predetermined redetection requirements have been satisfied. For example, a determination is made as to whether a predetermined number of three-second segments in both of the two channels ECG1 and ECG2, such as two out of the most recent three for example, have been classified as being shockable. If the predetermined redetection requirements are not satisfied, No in Block 608, the determination of whether to terminate delivery of the therapy, Block 606, is repeated so that the processing switches between the determination of whether to terminate delivery of therapy, Block 606 and the determination as to whether the shockable event is redetected, Block 608, until either the event has terminated and the device transitions from the armed state 306 to the not concerned state 302 or the event is redetected. If the predetermined redetection requirements are met, Yes in Block 608, charging is re-initiated, Block 600, and the process is repeated.

If, during the charging of the capacitors, the predetermined number of three second segments have not been classified as not shockable, No in Block 602, a determination is made as to whether the charging of the capacitors is completed, Block 610. As long as the predetermined number of three second segments continue to be classified as shockable, No in Block 602, charging of the capacitors continues until charging is completed. Once the charging of the capacitors is completed, Yes in Block 610, a determination is made as to whether delivery of the therapy is still appropriate, Block 612, by determining whether predetermined therapy delivery confirmation requirements have been satisfied. For example, according to an embodiment of the present invention, the predetermined therapy delivery confirmation requirements include determining whether, for both channels ECG1 and ECG2, at least five out of the last eight three-second segments are classified as being shockable, and at least two of the last three three-second segments are classified as being shockable. In addition, a determination is made as to whether the most recent three-second segment has been classified as being shockable for at least one of the two channels ECG1 and ECG2.

If the predetermined therapy delivery requirements have not been satisfied, and therefore the delivery of the therapy is not confirmed, No in Block 612, the determination of whether to transition from the armed state 306 to the not concerned state 302, Block 606, is repeated. If the predetermined therapy delivery requirements are satisfied, and therefore the delivery of the therapy is confirmed, Yes in Block 612, the device transitions from the armed state 306 to the shock state 308.

Figure 7G:
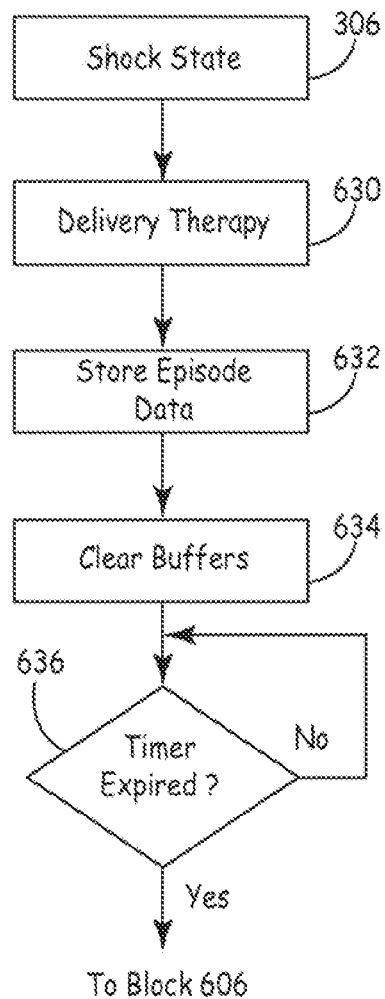
Figure 7H:
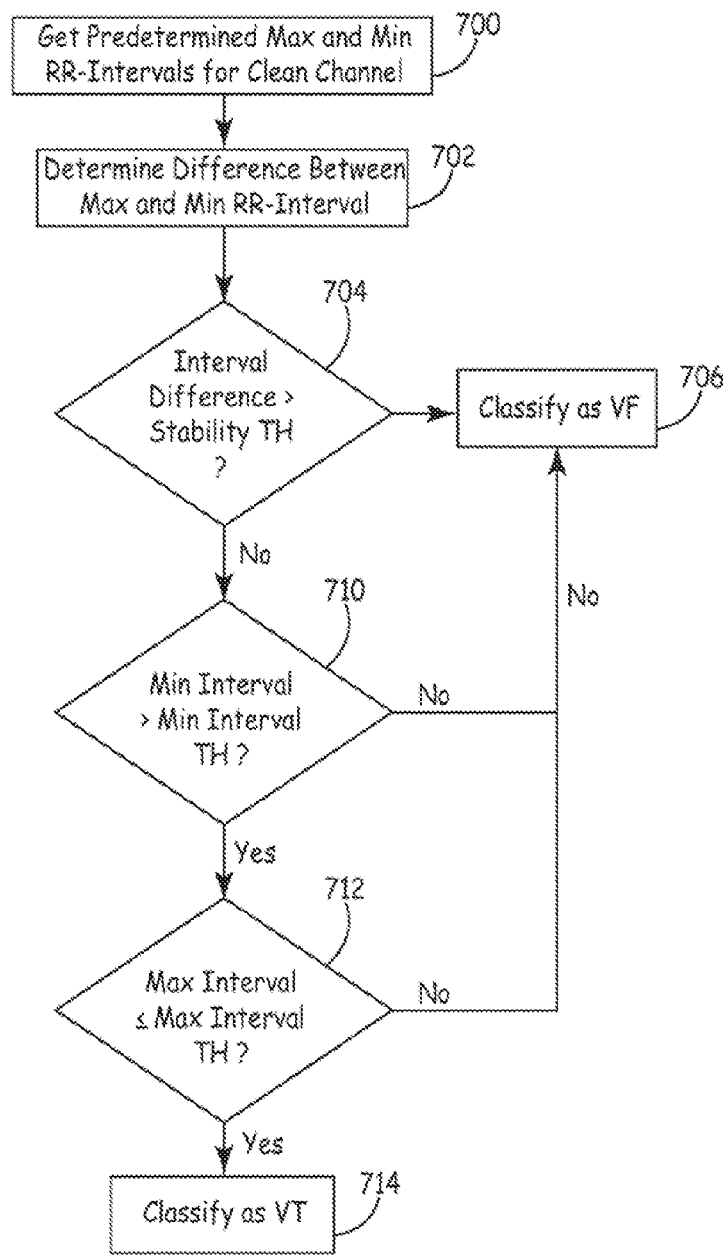
Figure 7I:
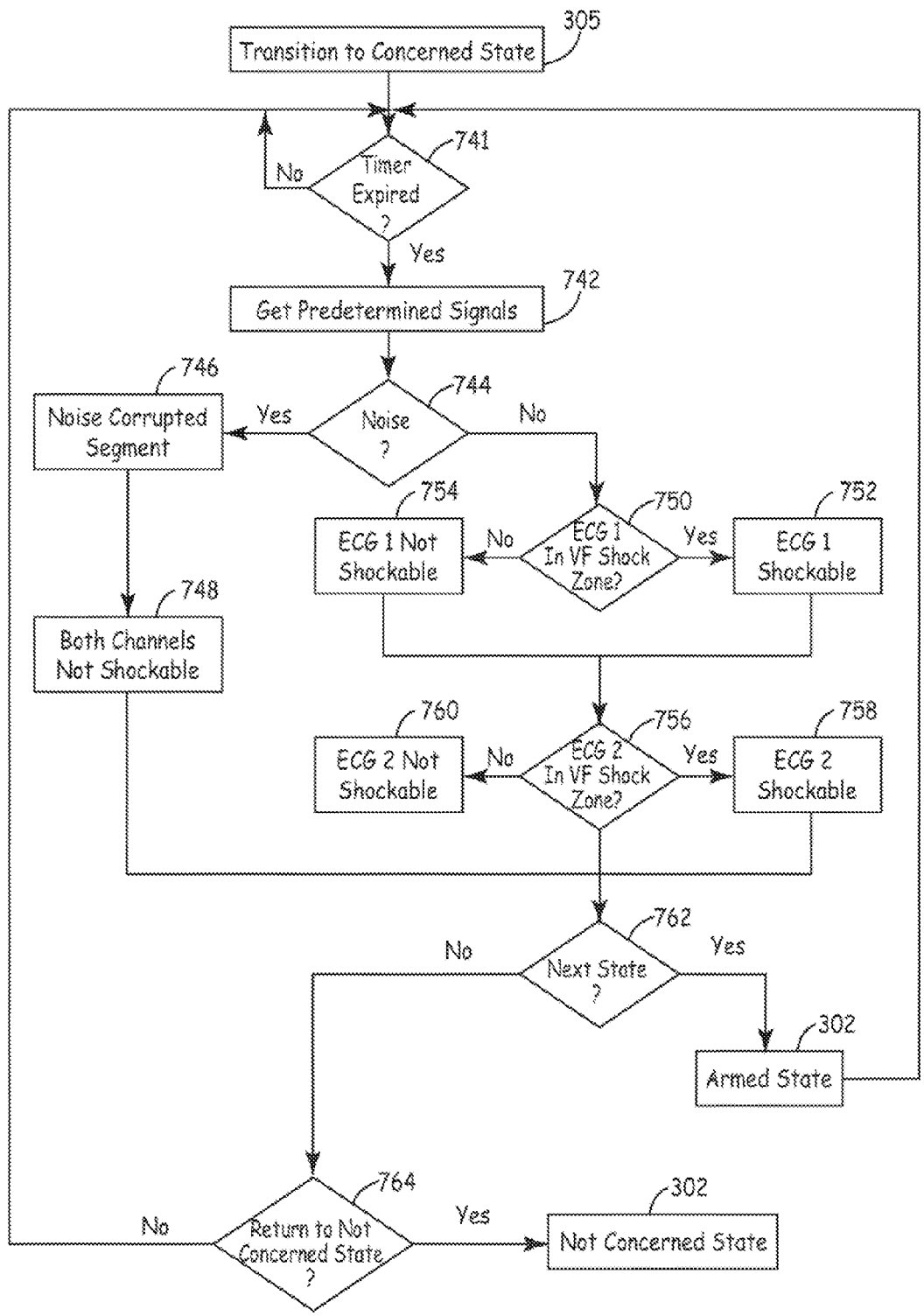
Figure 7J:
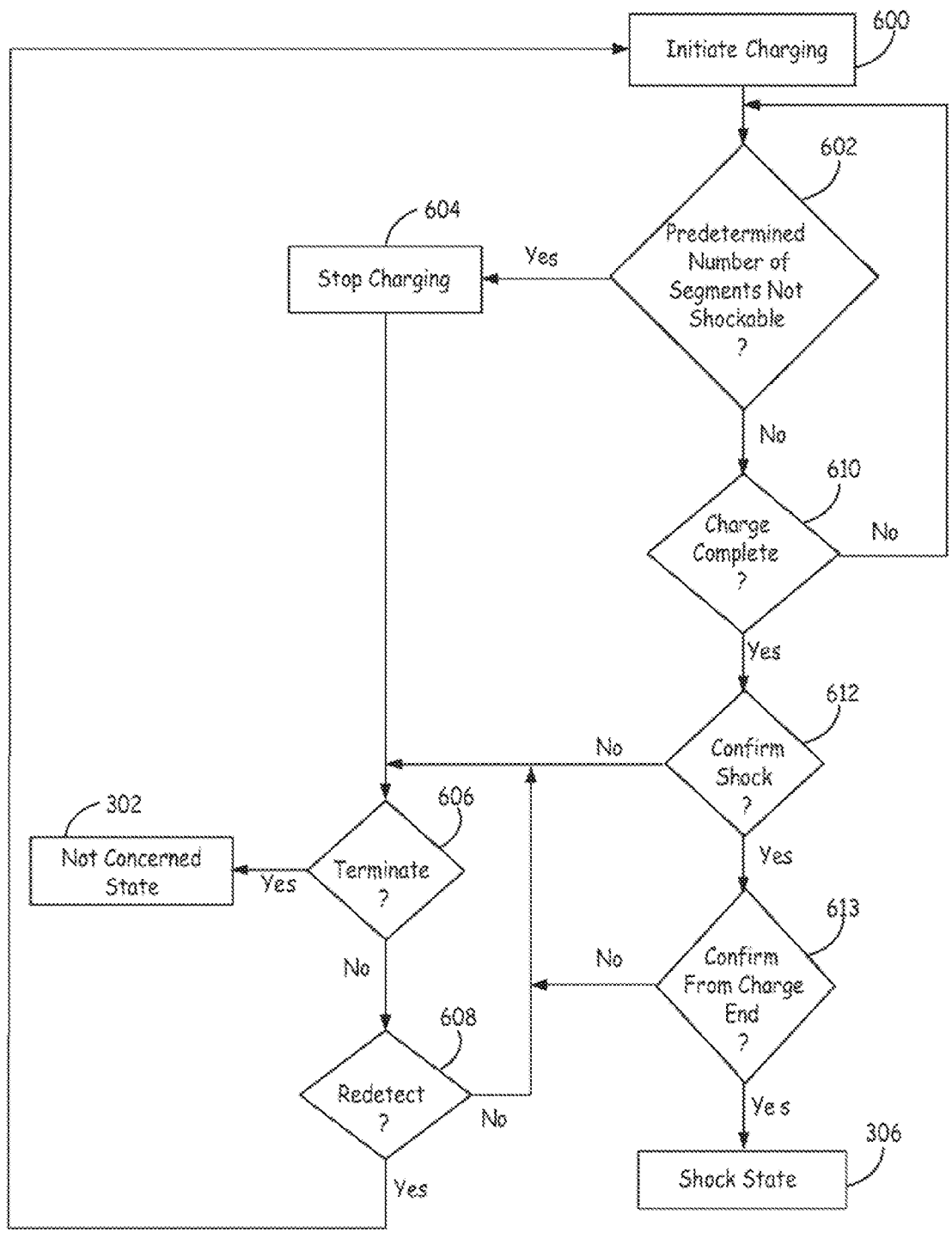

As illustrated in FIG. 7G, once the device transitions from the armed state 306 to the shock state 308, the therapy is delivered upon observation of the first sensed R-wave, Block 630, the episode data is stored, Block 632, and the buffers for storing the eight three second segments are cleared, Block 634. Once a post shock timer, such as three seconds for example, has expired, Yes in Block 636, the device transitions from the shock state 308 to Block 606 of the armed state 306. Since, as described above, classification of at least three subsequent three-second segments is required before the termination decision can be made in Block 606 subsequent to the delivery of therapy in the shock state 308, a determination based on the termination requirements cannot be initiated until at least twelve seconds after the initial shock therapy was delivered. The termination and redetection requirements are then reviewed until one of the two requirements are satisfied, i.e., the event is determined to have terminated, Yes in Block 606, or the event is redetected, Yes in Block 608. If the redetection requirements are satisfied, the charging of the capacitors is again initiated, Block 600, and processing in the armed state 306 continues as described above until all available therapies have been exhausted.

Figure 14:
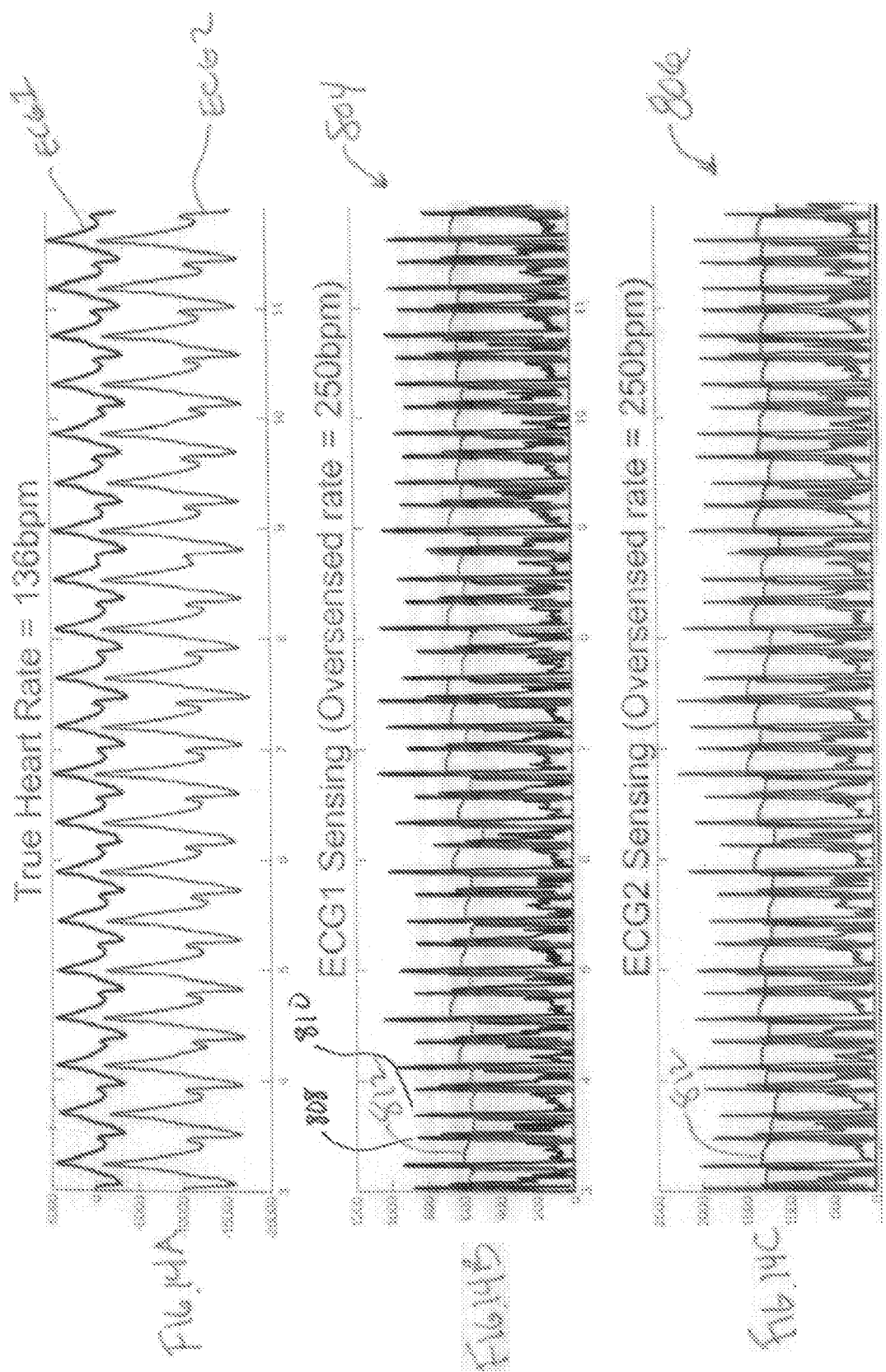
FIGS. 14A-14C are graphical representations illustrating the occurrence of oversensing due to a slow monomorphic ventricular tachycardia with a wide QRS complex.

FIGS. 14A-14C are graphical representations illustrating the occurrence of oversensing due to a slow monomorphic ventricular tachycardia with a wide QRS complex. The graphical representation in FIG. 14A is an exemplary illustration of a slow (less than the VT/VF threshold, i.e., 180 bpm) monomorphic ventricular tachycardia with a wide QRS complex, commonly referred to as a slow VT, sensed via the first sensing channel ECG1 and the second sensing channel ECG2. A resulting filtered and rectified signal 804 for the first sensing channel ECG1 is shown in FIG. 14B and a resulting filtered and rectified signal 806 for the second sensing channel ECG2 is shown in FIG. 14C. As can be seen in FIGS. 14A-14C, oversensing tends to occur during slow VT because each QRS complex results in two peak amplitudes 808 and 810 that exceed a sensing threshold 812 in one or more of the sensing channels ECG1 and ECG2, resulting in double counting of R-waves in one or more of the sensing channels ECG1 and ECG2. As a result, although the actual true heart rate occurring during slow VT may be less than the VT/VF threshold (i.e., 180 bpm), this oversensing resulting from the double counting of R-waves during such events causes the rhythm to be erroneously identified as a VT/VF rhythm.

Figure 15:
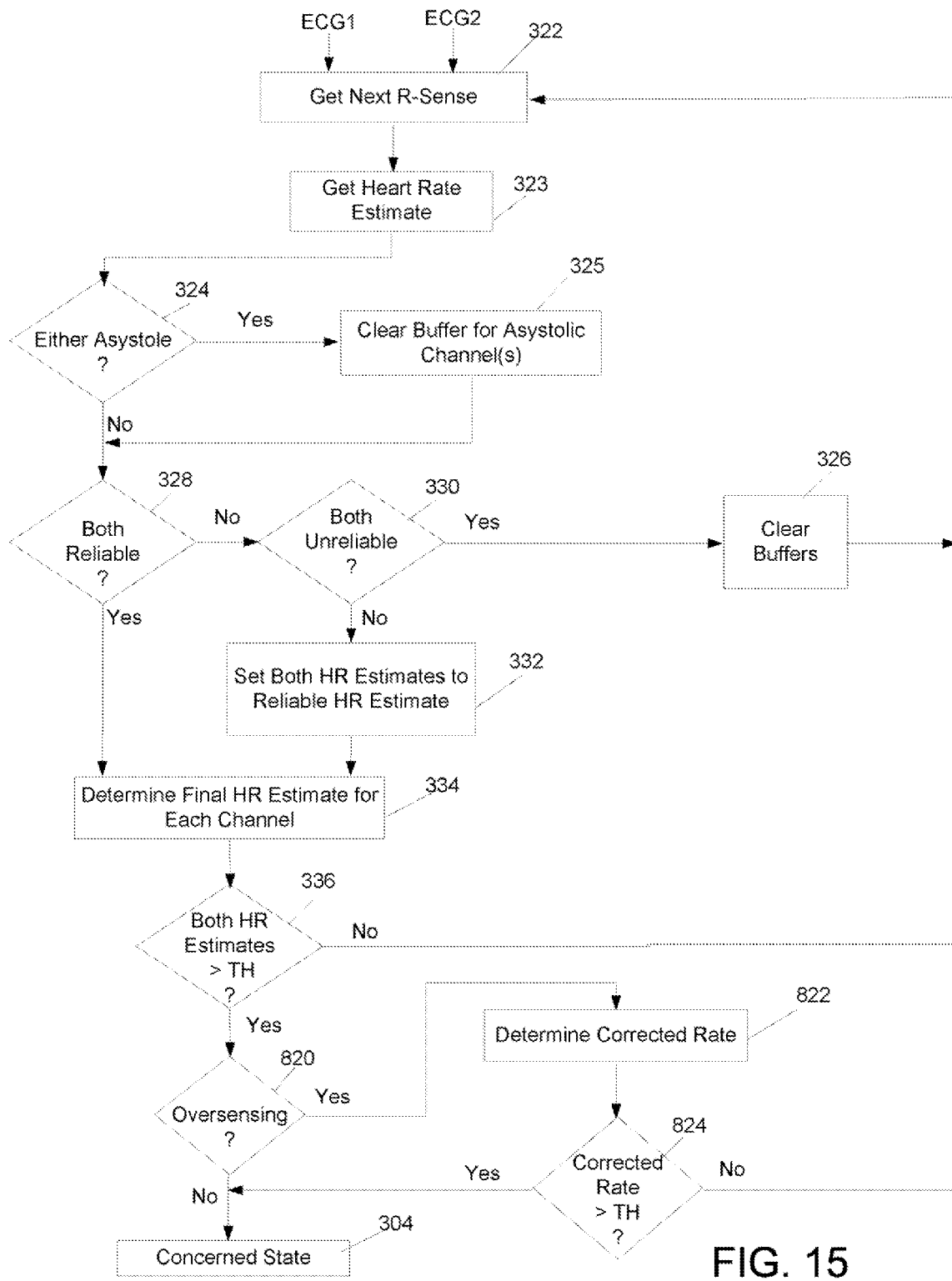
FIG. 15 is a flowchart of a method for detecting cardiac events in a medical device according to an embodiment of the present invention.

FIG. 15 is a flowchart of a method for detecting cardiac events in a medical device according to an embodiment of the present invention. The method illustrated in FIG. 15 is similar to the method described above in reference to FIG. 7A, but differs in that according to the method for detecting cardiac events according to the embodiment of FIG. 15 includes the additional process of detecting oversensing, which is described below. The process leading up to the oversensing detection is the same as described in FIG. 7A and will not be repeated here for brevity sake.

As illustrated in FIG. 15, once a VT/VF event has been determined to be present, i.e., the final heart rate estimates for both channels are determined to be greater than the predetermined VT/VF threshold, Yes in Block 336, a determination is made as to whether this determination occurred as a result of oversensing, Block 820. If oversensing is determined to have occurred, Yes in Block 820, the determined heart rate is corrected for the oversensing, Block 822, and a determination is made as to whether the corrected heart rate is greater than the predetermined VT/VF threshold, Block 824. If the corrected heart rate is not greater than the predetermined VT/VF threshold, No in Block 824, the buffer containing the 12 R-R intervals for the channel where the corrected heart rate not greater than the predetermined VT/VF threshold is updated by removing the first R-sense, shifting the remaining eleven R-sense samples back so that the second R-sense becomes the first R-sense, and so forth, and inserting the next detected R-sense, Block 322, as the twelfth R-sense. A new current heart rate estimate is then determined, Block 323 and the process is repeated.

If oversensing is not determined to have occurred, No in Block 820, or if oversensing is determined to be present and the subsequently generated corrected heart rate Block 822 is determined to be greater than the VT/VF threshold, Yes in Block 824, a VT/VF event is determined to be present and the process transitions from the not concerned state 302 to the concerned state 304.

Figure 16A:
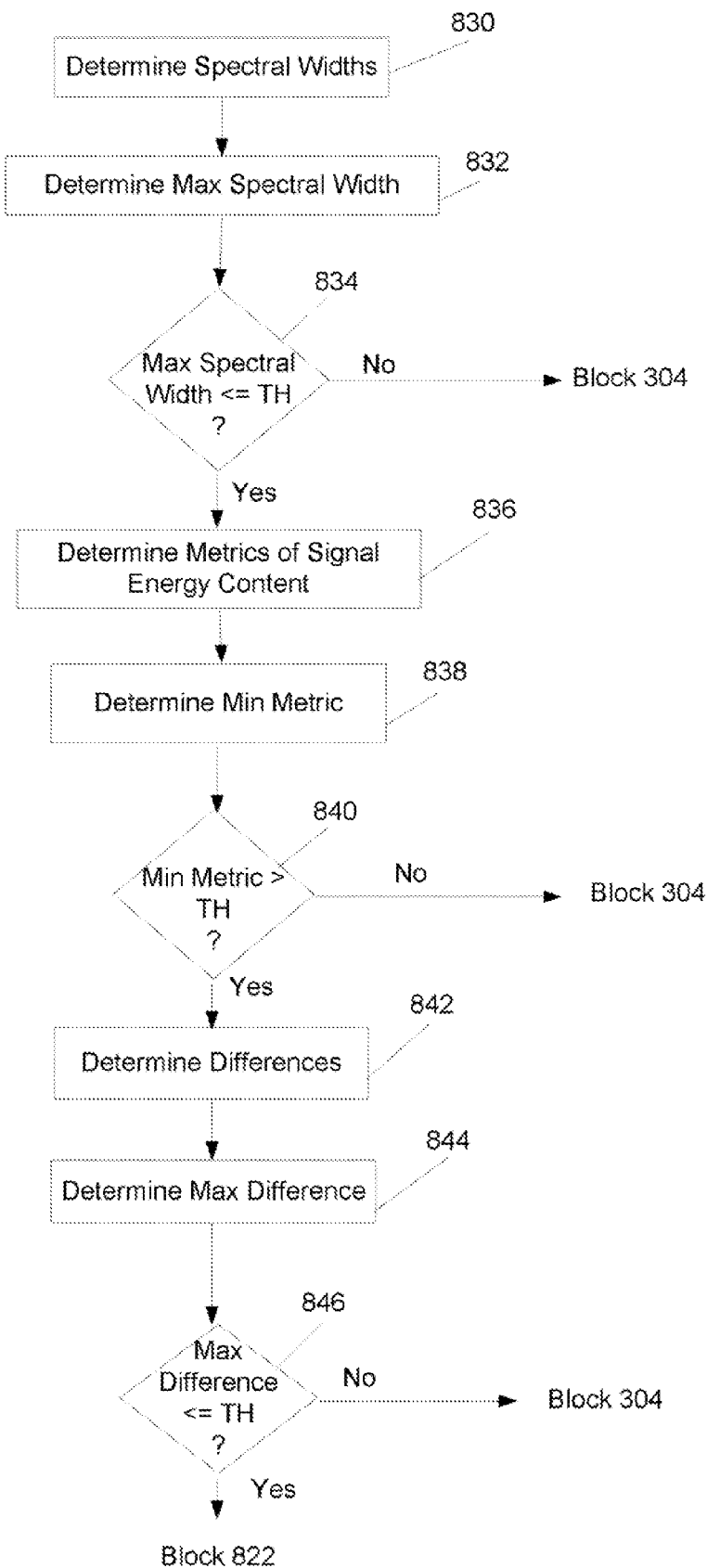
FIGS. 16A and 16B are flowcharts of a method of determining whether oversensing has occurred according to an embodiment of the present invention.
Figure 16B:
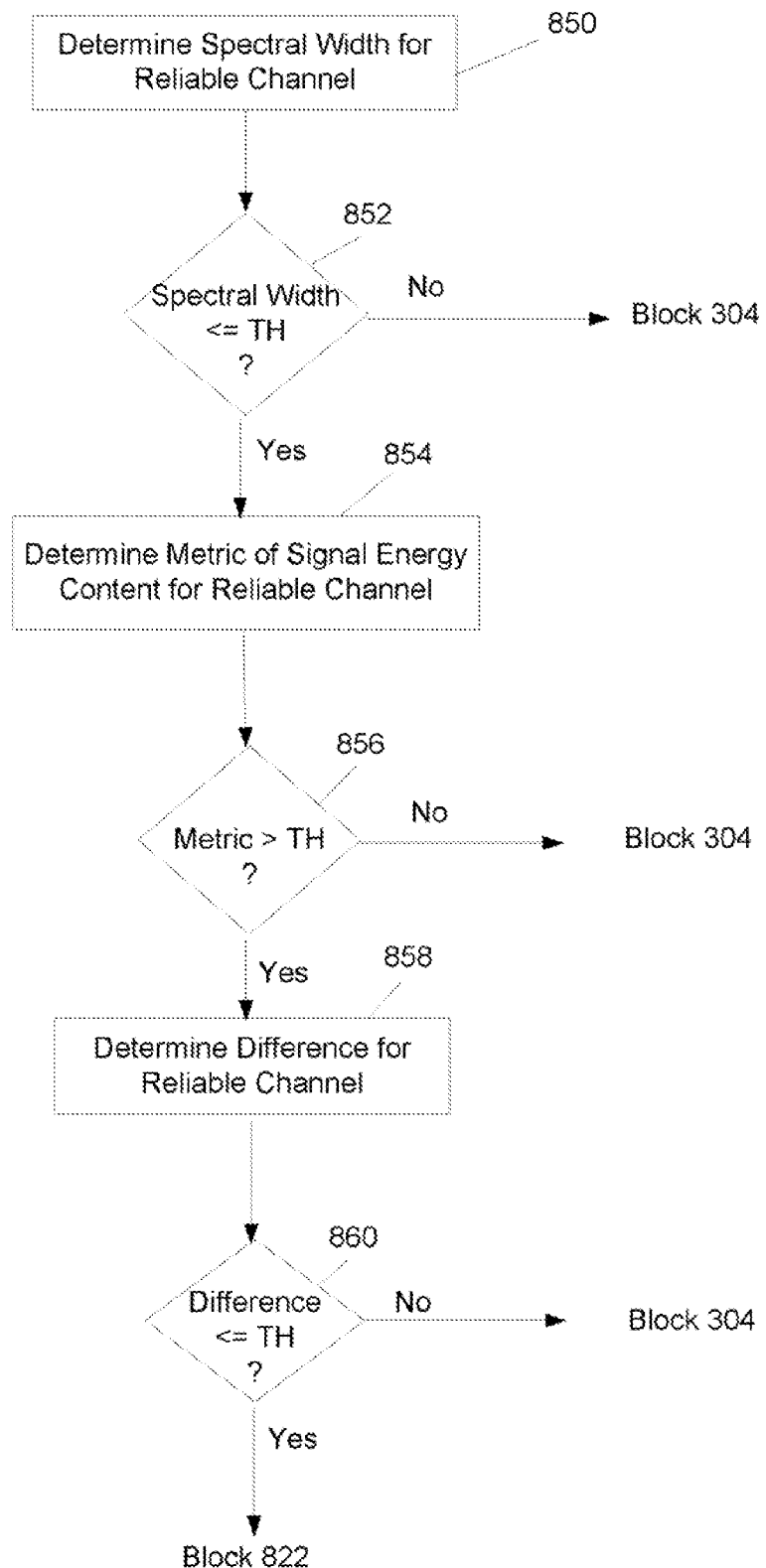

FIGS. 16A and 16B are flowcharts of a method of determining whether oversensing has occurred according to an embodiment of the present invention. According to an embodiment of the present invention, during the determination in Block 820 of whether oversensing has occurred, a determination is made as to whether predetermined criteria associated with oversensing are met. For example, as illustrated in FIG. 16A, if, after determining that both heart rate estimates are greater than VT/VF threshold, Block 336 of FIG. 15, both channels ECG1 and ECG2 were determined to be reliable, a spectral width is determined for each channel ECG1 and ECG2, Block 830, and a determination is made as to which one of the spectral width for the first channel ECG1 and the spectral width of the second channel ECG2 is the maximum spectral width, Block 832. A determination is then made as to whether the maximum spectral width is less than or equal to a spectral width threshold, Block 834. According to an embodiment of the present invention, the spectral width threshold is set as −20, although it is understood that any desired value may be utilized.

If the maximum spectral width is not less than or equal to the spectral width threshold, No in Block 834, oversensing is determined not to be occurring, and the device transitions to the concerned state, Block 304. If the maximum spectral width is less than or equal to the spectral width threshold, Yes in Block 834, a metric of signal energy content is determined for each channel ECG1 and ECG2, Block 836, and a determination is made as to which one of the metric of signal energy content for the first channel ECG1 and the metric of signal energy content for the second channel ECG2 is the minimum metric of signal energy content, Block 838. A determination is then made as to whether the minimum metric of signal energy content is greater than a metric of signal energy content threshold, Block 840. According to an embodiment of the present invention, the metric of signal energy content is a normalized mean rectified amplitude, generated as described above, and the metric of signal energy content threshold is 40.

If the minimum metric of signal energy content is not greater than the metric of signal energy content threshold, No in Block 840, oversensing is determined to not be occurring, and the device transitions from the not concerned state 302 to the concerned state 304. If the minimum metric of signal energy content is greater than the metric of signal energy content threshold, Yes in Block 840, a heart rate metric difference is determined for each channel ECG1 and ECG2, Block 842, and a determination as to which one of the heart rate metric difference for the first channel ECG1 and the heart rate metric difference for the second channel ECG2 is the maximum heart rate metric difference, Block 844. A determination is then made as to whether the maximum heart rate metric difference is less than or equal to a heart rate metric difference threshold, Block 846, such as 52.5 ms for example. If the maximum heart rate metric difference is greater than the heart rate metric difference threshold, No in Block 846, oversensing is determined to not be occurring, and the device transitions from the not concerned state 302 to the concerned state 304. If the maximum heart rate metric difference is less than or equal to the heart rate metric difference threshold, Yes in Block 846, oversensing is determined to likely be occurring and the corrected rate is determined, Block 822 of FIG. 15, described below.

According to an embodiment of the present invention, the heart rate metric difference is derived from the 12 RR intervals currently stored in the buffer so that the heart rate metric difference for each channel ECG 1 and ECG2 is generated by first determining the trimmed mean of the third through the tenth RR intervals TM=Mean $\{RR_3:RR_{10}\}$, and calculating an absolute difference between the second RR interval and the trimmed mean $|RR_2-TM|$, between the fifth RR interval and the trimmed mean $|RR_5-TM|$, between the eight RR interval and the trimmed mean $|RR_8-TM|$, and between the eleventh RR interval and the trimmed mean $|RR_{11}-TM|$. The heart rate metric difference for the channel is then set equal to the average of the four calculated absolute differences, As illustrated in FIG. 16B, if, after determining that both heart rate estimates are greater than the VT/VF threshold, Block 336, only one of the channels ECG1 and ECG2 was determined to be reliable, No in Block 328 and Yes in Block 330, the oversensing criteria are applied using only the reliable channel. For example, if the first channel ECG1 was determined to be unreliable and the second channel ECG2 was determined to be the reliable channel, a spectral width is determined for the reliable channel ECG2, Block 850, and a determination is made as to whether the spectral width is less than or equal to the spectral width threshold, Block 852.

If the spectral width is not less than or equal to the spectral width threshold, No in Block 852, oversensing is determined not to be occurring, and the device transitions to the concerned state, Block 304. If the spectral width is less than or equal to the spectral width threshold, Yes in Block 852, a metric of signal energy content is determined for the reliable channel ECG2, Block 854, and a determination is made as to whether the metric of signal energy content is greater than the metric of signal energy content threshold, Block 856.

If the metric of signal energy content is not greater than the metric of signal energy content threshold, No in Block 856, oversensing is determined to not be occurring, and the device transitions from the not concerned state 302 to the concerned state 304. If the metric of signal energy content is greater than the metric of signal energy content threshold, Yes in Block 856, a heart rate metric difference is determined for the reliable channel ECG2, Block 858, and a determination as to whether the heart rate metric difference is less than or equal to the heart rate metric difference threshold, Block 860. If the heart rate metric difference is greater than the heart rate metric difference threshold, No in Block 860, oversensing is determined to not be occurring, and the device transitions from the not concerned state 302 to the concerned state 304. If the heart rate metric difference is less than or equal to the heart rate metric difference threshold, Yes in Block 860, oversensing is determined to likely be occurring and the corrected rate is determined, Block 822 of FIG. 15, using the rate correction technique described below.

It is understood that while the method of determining whether oversensing has occurred described above in reference to FIGS. 16A and 16B includes three oversensing characteristics that must be satisfied, spectral width, the metric of signal energy content, and the heart rate metric difference, in order for oversensing to be detected, the present invention may require that a combination of any two, or only one of the three oversensing characteristics to be satisfied in order for oversensing to be detected. In addition, while the three oversensing characteristics are described in terms of the spectral width being the first to be determined, followed by the metric of signal energy content, and then the heart rate metric difference, if more than one of the oversensing characteristics is utilized, they may occur in any order.

Figure 17:
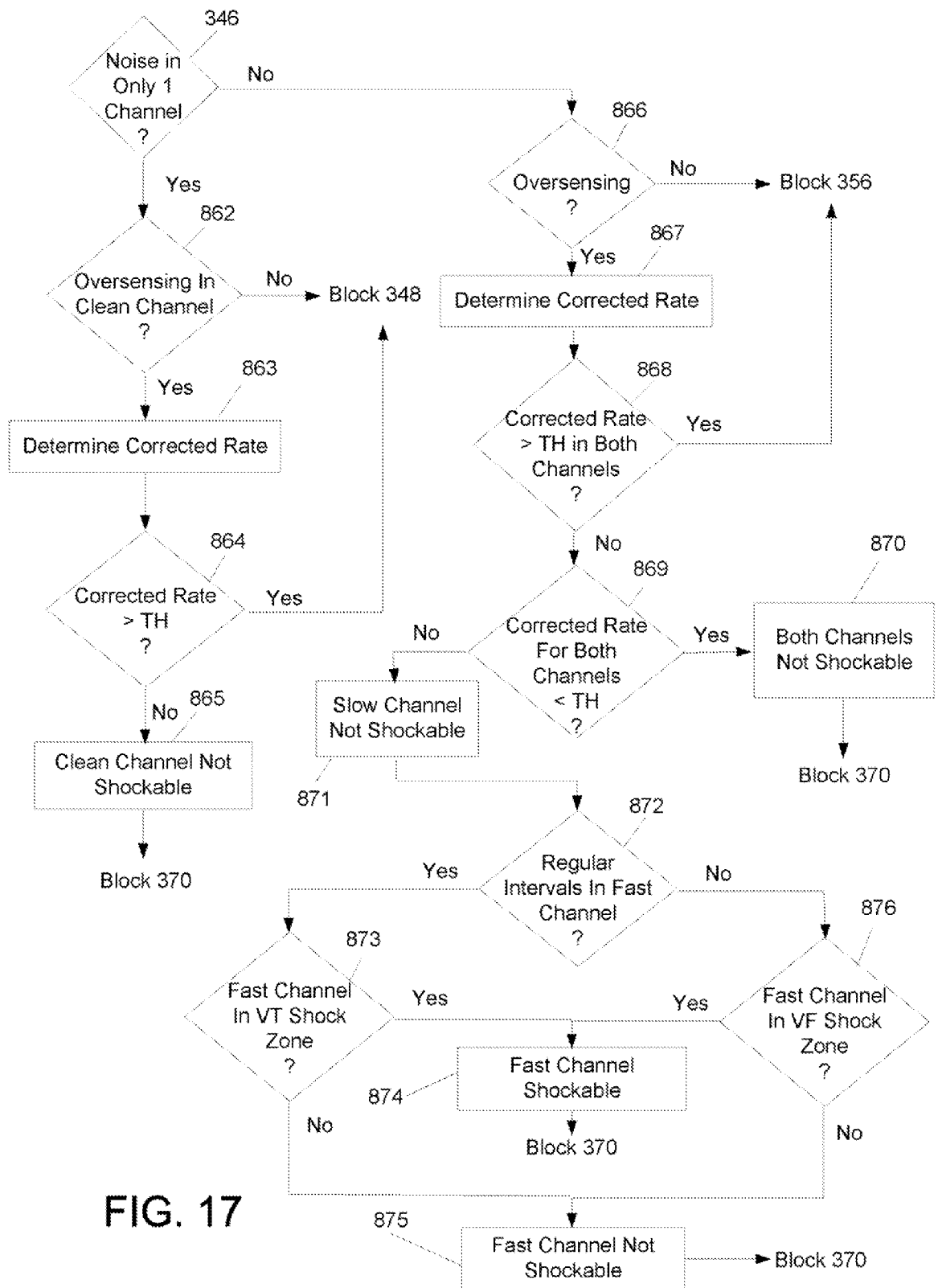
FIG. 17 is a flowchart of a method of determining whether oversensing has occurred according to an embodiment of the present invention.

FIG. 17 is a flowchart of a method of determining whether oversensing has occurred according to an embodiment of the present invention. As illustrated in FIGS. 7B and 17, once the device has transitioned from the not concerned state 302 to the concerned state 304, and it is determined that noise was detected in only one of the channels, Yes in Block 346, a determination is made as to whether oversensing has occurred in the clean channel, Block 862. Since the oversensing is determined for only one of the two channels ECG1 and ECG 2, i.e., the non-noisy or clean channel, the oversensing criteria as describe above in reference to FIG. 16B is utilized in the oversensing determination of Block 862. If oversensing is not detected, No in Block 862, the above-described determination of whether there are regular intervals in the clean channel, Block 348, is made and the process continues in FIG. 7B as described above.

If oversensing is determined to be detected, a corrected rate for the clean channel is determined, Block 863, using the rate correction process described below, and a determination is then made as to whether the corrected rate is greater than the VT/VF detection threshold, Block 864. If the corrected heart rate is greater than the VT/VF threshold, the above-described determination of whether there are regular intervals in the clean channel, Block 348, is made and the process continues in FIG. 7B as described above. If the corrected rate is not greater than the VT/VF threshold, No in Block 864, the clean channel is classified as being unshockable, Block 865, and the determination is made as to whether the device should transition from the concerned state 304 to the armed state 306, Block 370, as described above.

If it is determined that both channels ECG1 and ECG2 are noise-free, i.e., both are clean channels, No in Block 346, a determination is made as to whether oversensing has occurred, Block 866, using both channels ECG1 and ECG2. Since the oversensing is determined using both channels ECG1 and ECG 2, the oversensing criteria as describe above in reference to FIG. 16A is utilized in the oversensing determination of Block 866. If oversensing is not detected, No in Block 866, the determination of whether there are regular intervals in both channels ECG1 and ECG2, Block 356, is made and the process continues in FIG. 7B as described above.

If oversensing is determined to be detected, a corrected rate is determined for each channel ECG1 and ECG2, Block 867, using the rate correction process described below, and a determination is then made as to whether the corrected rates for both channels ECG 1 and ECG2 are greater than the VT/VF detection threshold, Block 868. If the corrected heart rates for both channels ECG1 and ECG2 are greater than the VT/VF threshold, Yes in Block 868, the determination of whether there are regular intervals in both channels, Block 356, is made and the process continues in FIG. 7B as described above. If the corrected rates for both channels ECG1 and ECG2 are not greater than the VT/VF threshold, No in Block 868, a determination is made as to whether the corrected rate for both of the channels ECG1 and ECG2 is less than or equal to the VF/VF threshold, Block 869. If the corrected rates for both of the channels ECG1 and ECG2 is less than or equal to the VF/VF threshold, Yes in Block 869, i.e., both channels ECG1 and ECG2 are slow, and therefore both channels ECG1 and ECG 2 are classified as being not shockable, Block 870, and the determination is made as to whether the device should transition from the concerned state 304 to the armed state 306, Block 370, as described above.

If the corrected rates for both of the channels ECG1 and ECG2 are not less than or equal to the VF/VF threshold, No in Block 869, indicating that the corrected rate for one of the channels ECG1 and ECG2 is less than or equal to the VF/VF threshold and the corrected rate for the other of the channels ECG1 and ECG2 is greater than the VT/VF threshold, the channel that was determined to be less than the VT/VF threshold, i.e., the slow channel, is classified as being non-shockable, Block 871, and a determination is made as to whether there are regular intervals in the channel that was greater than the VT/VF threshold, i.e., the fast channel, Block 872, using the regular intervals processing as described above, indicating the channel can be classified as being stable.

If the fast channel is determined to have regular intervals, a determination is made as to whether the fast channel is in the VT shock zone, Block 873, using the VT shock zone determination described above. If the fast channel is in the VT shock zone, the fast channel is classified as shockable, Block 874, and the determination is made as to whether the device should transition from the concerned state 304 to the armed state 306, Block 370, as described above. If the fast channel is not in the VT zone, the fast channel is classified as being not shockable, Block 875, and the determination is made as to whether the device should transition from the concerned state 304 to the armed state 306, Block 370, as described above.

If the fast channel is determined not to have regular intervals, No in Block 872, a determination is made as to whether the fast channel is in the VF shock zone, Block 876, using the VF shock zone criteria described above. If the fast channel is in the VF shock zone, the fast channel is classified as shockable, Block 874, and the determination is made as to whether the device should transition from the concerned state 304 to the armed state 306, Block 370, as described above. If the fast channel is not in the VF zone, the fast channel is classified as being not shockable, Block 875, and the determination is made as to whether the device should transition from the concerned state 304 to the armed state 306, Block 370, as described above.

Figure 18:
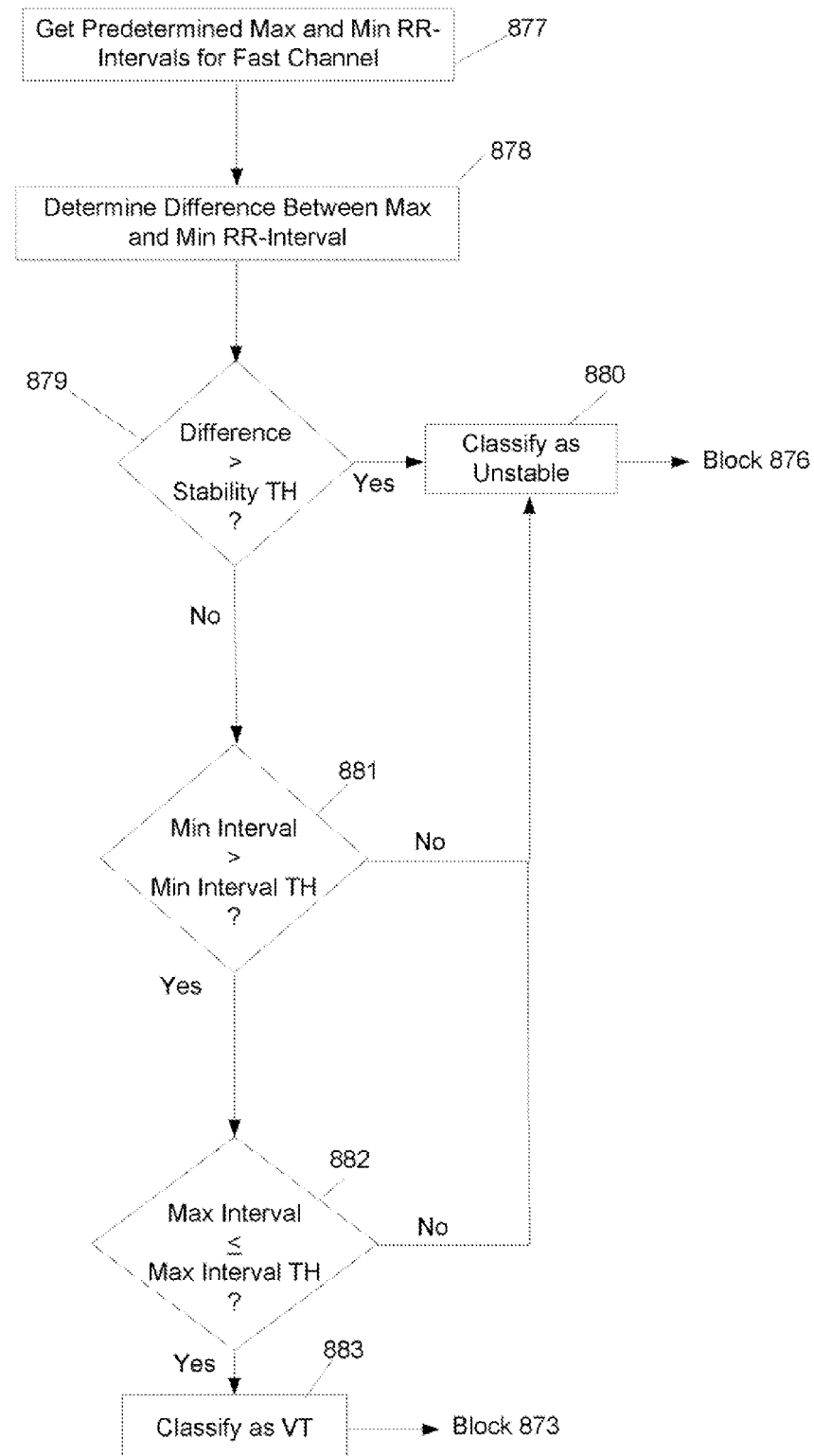
FIG. 18 is a flowchart of a method of determining whether oversensing has occurred according to an embodiment of the present invention.

FIG. 18 is a flowchart of a method of determining whether oversensing has occurred according to an embodiment of the present invention. As illustrated in FIG. 18, in order to determine whether the fast channel has regular intervals, Block 872 of FIG. 17, and can therefore be classified as being relatively stable, predetermined maximum and minimum intervals for the fast channel are identified, Block 877, using the updated buffer of 12 RR-intervals. According to one embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated, Block 878, to generate an interval difference associated with the fast channel. A determination is made as to whether the interval difference is greater than a predetermined stability threshold, Block 879, such as 110 milliseconds, for example.

If the interval difference is greater than the stability threshold, the segment is classified as an unstable segment, Block 880, and a determination is made as to whether the signal associated with the fast channel is within a predetermined VF shock zone, Block 876, described above. If the interval difference is less than or equal to the stability threshold, No in Block 879, the device determines whether the minimum RR-interval associated with the fast channel is greater than a minimum interval threshold, Block 881, such as 200 milliseconds, for example.

If the minimum RR interval is less than or equal to the minimum interval threshold, the segment is classified as an unstable segment, Block 880, and a determination is made as to whether the signal associated with the fast channel is within a predetermined VF shock zone, Block 876, described above. If the minimum interval is greater than the minimum interval threshold, the device determines whether the maximum RR-interval associated with the fast channel is less than or equal to a maximum interval threshold, Block 882, such as 333 milliseconds for example. If the maximum interval is greater than the maximum interval threshold, the segment is classified as an unstable segment, Block 880, and a determination is made as to whether the signal associated with the fast channel is within a predetermined VF shock zone, Block 876, described above.

If the maximum interval is less than or equal to the maximum interval threshold, the segment is classified as a stable segment, Block 883, and a determination is made as to whether the signal associated with the fast channel is within a predetermined VT shock zone, Block 873, described above.

It should be noted that, as described above in reference to FIG. 7F, when the device transitions from the concerned state 304 to the armed state 306, Yes in Block 370, processing continues to be triggered by a three-second time out as is utilized during the concerned state 304, described above, and once the device transitions from the concerned state 302 to the armed state 306, charging of the capacitors is initiated, Block 600. During the charging of the capacitors, the classification of segments for each channel ECG1 and ECG2 as being either shockable or not shockable generated during the shock zone tests described above continues, and, according to an embodiment of the present invention, this classification of the segments while in the armed state 306 includes the determination of whether oversensing has occurred, along with the generation of the corrected rate when oversensing has occurred, as described above.

Figure 20A:
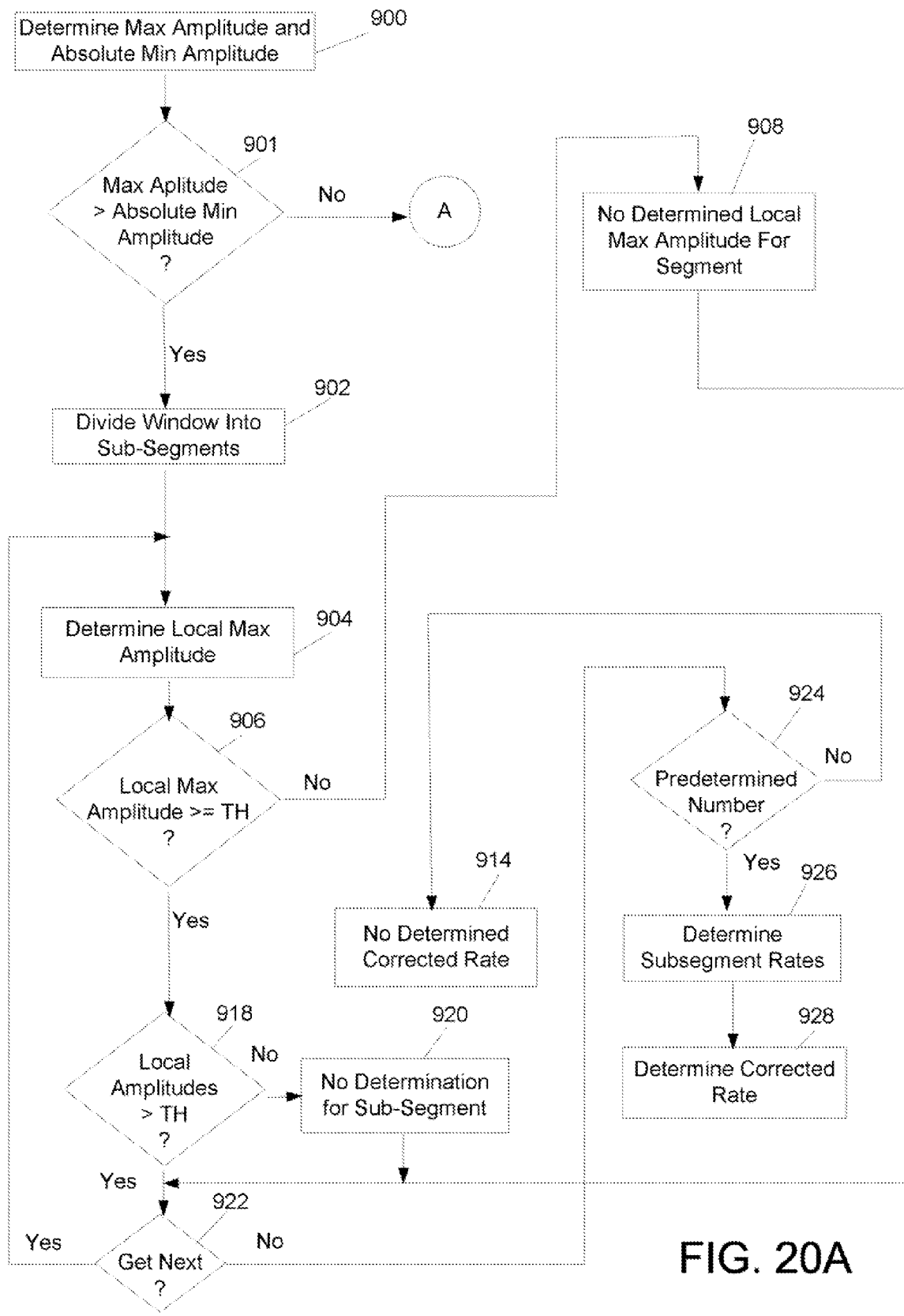
FIGS. 20A and 20B are flowcharts of a method of determining a corrected heart rate in response to oversensing according to an embodiment of the present invention.
Figure 20B:
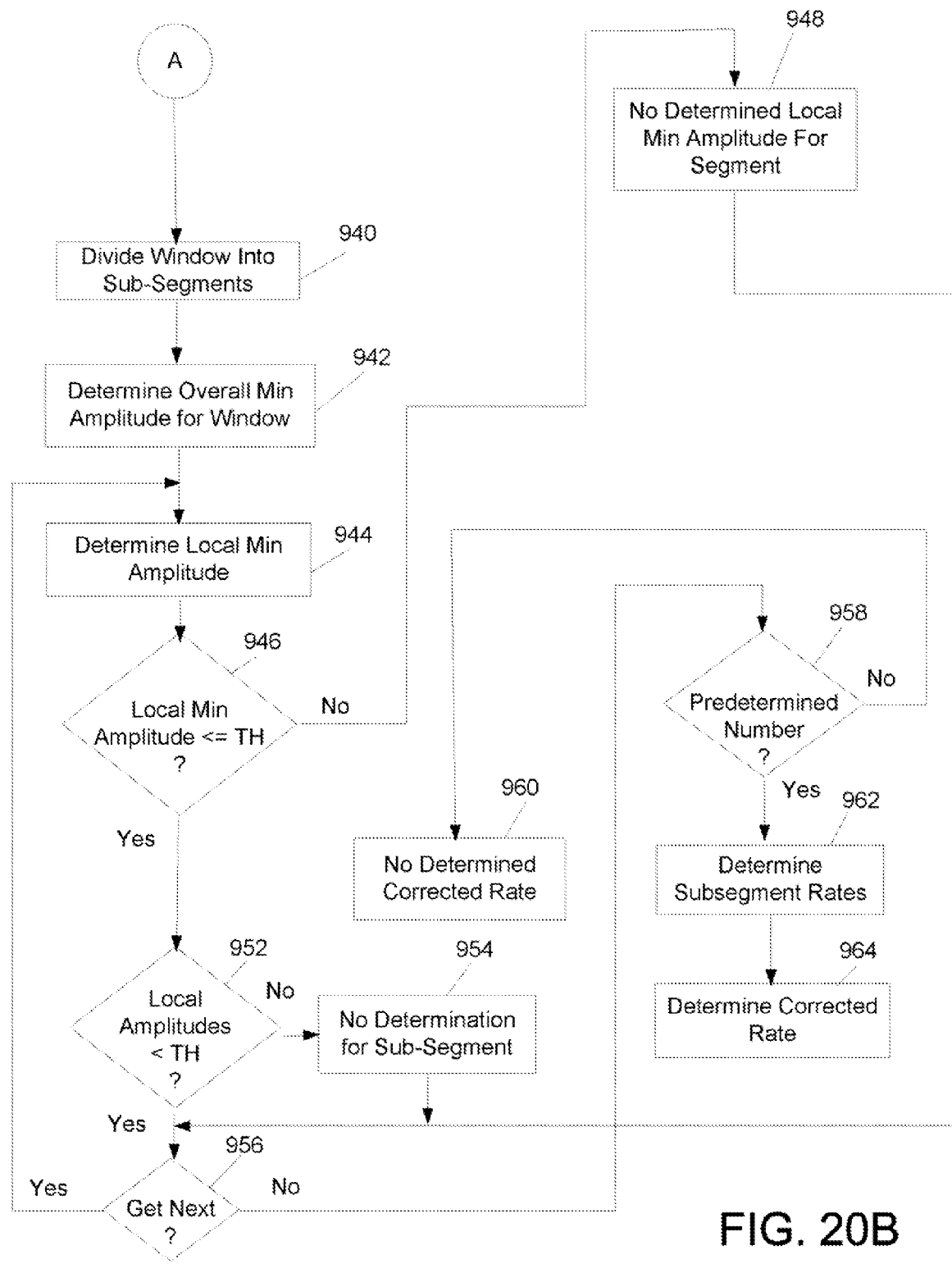

FIGS. 19A and 19B are graphical representations of determining a corrected heart rate in response to oversensing according to an embodiment of the present invention. FIGS. 20A and 20B are flowcharts of a method of determining a corrected heart rate in response to oversensing according to an embodiment of the present invention. As illustrated in FIGS. 19A, 19B and FIGS. 20A and 20B, during the determination of an updated or corrected heart rate in response to determining the presence of oversensing, the device first determines a maximum amplitude 886 and an absolute value of the minimum amplitude for the current three second window, Block 900, and determines whether the maximum amplitude for the three second window is greater than the absolute value of the minimum amplitude for the three second window, Block 901. If the maximum amplitude for the three second window is not greater than the absolute value of the minimum amplitude for the three second window, No in Block 901, the device uses the minimum amplitudes to determine the corrected rates, Block A, described below in FIG. 20B.

In order to determine an updated or corrected heart rate, a determination is made as to whether certain predetermined criteria associated with the corrected heart rate are met. For example, if the maximum amplitude 886 for the three second window is greater than the absolute value of the minimum amplitude for the three second window, Yes in Block 901, the device divides the three second window 884 into a predetermined number of window sub-segments 885, Block 902. A local maximum amplitude 887 is determined for one of the sub-segments 885, Block 904, and a determination is made as to whether the local maximum 887 for that sub-segment 885 is greater than a predetermined local maximum amplitude threshold, Block 906. According to an embodiment of the present invention, the predetermined local maximum amplitude threshold is a percentage of the overall maximum amplitude 886 for the sensing window, such as 65% of the overall maximum amplitude 886.

If the current local maximum amplitude 887 is not greater than the local maximum amplitude threshold, No in Block 906, no determination of a maximum amplitude is made for that sub-segment, Block 908, and the device determines whether the local maximum amplitude 887 and local amplitudes 888 have been determined for all of the four sub-segments 885, Block 922, described below. If the current local maximum amplitude 887 is greater than the local maximum amplitude threshold, Yes in Block 906, the device determines whether the sub-segment 885 includes a local amplitude 888 that is greater than a local amplitude threshold, Block 918.

According to an embodiment of the present invention, the local amplitude threshold of Block 918 is a percentage of the local maximum amplitude 887 for that sub-segment 885, such as 70% of the local maximum amplitude 887 for that sub-segment 885, for example. If the sub-segment 885 does not include a local amplitude 888 that is greater than the local amplitude threshold, No in Block 918, a determination cannot be made for that sub-segment 885, Block 920, and the device determines whether a local maximum amplitude 887 and local amplitudes 888 have been determined for all of the four sub-segments 885, Block 922, described below.

If the sub-segment 885 includes at least one local amplitude 888 that is greater than the local amplitude threshold, Yes in Block 918, or if no determination of a local maximum amplitude was made, Block 908, the device determines whether the local maximum amplitude 887 and local amplitudes 888 have been determined for all of the four sub-segments 885, Block 922. If all of the local maximum amplitude 887 and local amplitudes 888 have not been determined for all of the sub-segments 885, Yes in Block 922, the process is repeated for the next sub-segment 885.

In order to obtain a corrected heart rate for a three second window, the device must be successful in locating a local maximum amplitude 887 and at least one local amplitude 888 in a predetermined number of the sub-segments, such as two sub-segments for example. Therefore, once the determination of a local maximum amplitude 887 and the local amplitudes 888, Blocks 904-918, has been made for all of the sub-segments 885, No in Block 922, a determination is made as to whether a local maximum amplitude 887 and at least one local amplitude 888 were found to exist in the predetermined number of sub-segments 885, Block 924. If a local maximum amplitude 887 and at least one local amplitude 888 greater than the local amplitude threshold were not found for the predetermined number of sub-segments 885, No in Block 924, no corrected heart rate is determined for the three second window, Block 914. If a local maximum amplitude 887 and at least one local amplitude 888 greater than the local amplitude threshold was found for the predetermined number of sub-segments 885, Yes in Block 924, rates are determined for each of the four sub-segments 885, Block 926, and the corrected rate is determined using the determined sub-segment rates, Block 928.

If the maximum amplitude for the three second window is not greater than the absolute value of the minimum amplitude for the three second window, No in Block 901, the device uses the minimum amplitudes to determine the corrected rates, Block A in FIG. 20A. In particular, as illustrated in FIG. 20B, the device divides the three second window 934 into a predetermined number of window sub-segments 935, Block 940, and determines an overall minimum amplitude 936 associated with the entire window, Block 942. A local minimum amplitude 937 is determined for one of the sub-segments 935, Block 944, and a determination is made as to whether the local minimum 937 for that sub-segment 935 is less than a predetermined local minimum amplitude threshold, Block 946. According to an embodiment of the present invention, the predetermined local minimum amplitude threshold is a percentage of the overall minimum amplitude 936 for the sensing window, such as 65% of the overall minimum amplitude 936.

If the current local minimum amplitude 937 is not less than the local minimum amplitude threshold, No in Block 946, no determination of a minimum amplitude is made for that sub-segment, Block 948, and the device determines whether the local minimum amplitude 937 and local amplitudes 938 have been determined for all of the four sub-segments 935, Block 956, described below. If the current local minimum amplitude 937 is less than the local minimum threshold, Yes in Block 946, the device determines whether the sub-segment 935 includes local amplitudes 938 that are less than a local amplitude threshold, Block 952.

According to an embodiment of the present invention, the local amplitude threshold of Block 952 is a percentage of the local minimum amplitude 937 for that sub-segment 935, such as 70% of the local minimum amplitude 937 for that sub-segment 935, for example. If the sub-segment 935 does not include at least one local amplitude 938 that is less than the local amplitude threshold, No in Block 952, a determination cannot be made for that sub-segment 935, Block 954, and the device determines whether the local minimum amplitude 937 and local amplitudes 938 have been determined for all of the four sub-segments 935, Block 956, described below.

If the sub-segment 935 includes at least one local amplitude 938 that is less than the local amplitude threshold, Yes in Block 952, or if no determination of a local minimum amplitude was made, Block 948, the device determines whether the local minimum amplitude 937 and local amplitudes 938 have been determined for all of the four sub-segments 935, Block 956. If all of the local minimum amplitudes 937 and local amplitudes 938 have not been determined for all of the sub-segments 935, Yes in Block 956, the process is repeated for the next sub-segment 935.

In order to obtain a corrected heart rate for a three second window, the device must be successful in locating a local minimum amplitude 937 and at least one local amplitude 938 in a predetermined number of the sub-segments, such as two sub-segments for example. Therefore, once the determination of a local minimum amplitude 937 and the local amplitudes 938, Blocks 942-952, has been made for all of the sub-segments 935, No in Block 956, a determination is made as to whether a local minimum amplitude 937 and at least one local amplitude 938 less than the local amplitude threshold has been found for the predetermined number of sub-segments 935, Block 958. If a local minimum amplitude 937 and at least one local amplitude 938 less than the local amplitude threshold were not found for the predetermined number of sub-segments 935, No in Block 958, no corrected heart rate is determined for the three second window, Block 960. If a local minimum amplitude 937 and at least one local amplitude 938 less than the local amplitude threshold were found for the predetermined number of sub-segments 935, Yes in Block 958, rates are determined for each of the four sub-segments

935, Block 962, and the corrected rate is determined using the determined sub-segment rates, Block 964.

Figure 21:
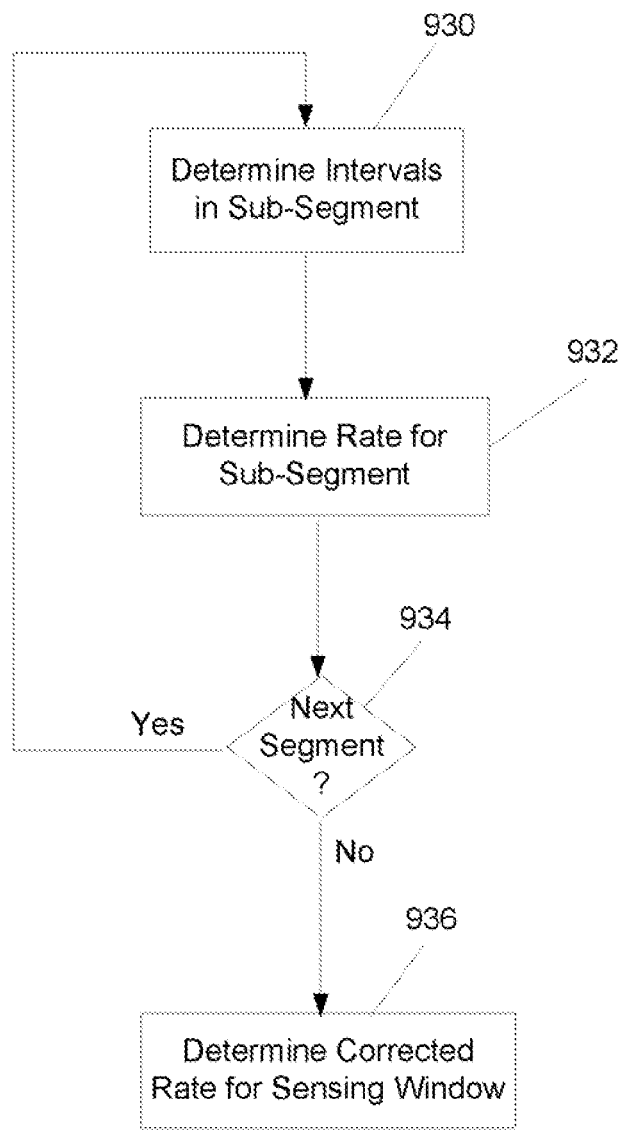
FIG. 21 is a flowchart of a method for determining a corrected rate according to an embodiment of the present invention.

FIG. 21 is a flowchart of a method for determining a corrected rate according to an embodiment of the present invention. The flowchart of FIG. 21 describes the determination of the sub-segment rates when the maximum amplitude is utilized, Yes in Block 901 of FIG. 20A. The determination of the sub-segment rates when the minimum amplitudes are utilized, No in Block 901, is similar to the determination when the maximum amplitude is utilized, differing only in that minimum amplitudes are used in place of the maximum amplitudes, and therefore is not included merely for brevity sake.

In particular, according to an embodiment of the present invention, in order to determine sub-segment rates, Block 926, the device determines interval rates associated with the local maximum amplitude 887 and the local amplitudes 888 within a sub-segment 885 that were determined in Block 918, and a sub-segment rate for each of the sub-segments 885 is determined based on the RR interval rates, Block 932. For example, as illustrated in FIG. 19A, one of the sub-segments 885 includes the local maximum amplitude 887 and two local amplitudes 888 so that two RR intervals, RR1 and RR2 are determined as the intervals for that sub-segment 885 in Block 930. The rate for that sub-segment 885 is determined in Block 932 based on RR intervals RR1 and RR2, such as based on the average of the RR intervals RR1 and RR2. If a sub-segment rate has not been determined for all of the sub-segments 885 for which a local maximum amplitude 887 and at least one local amplitude 888 were previously determined, Yes in Block 334, the device determines a sub-segment rate for the next sub-segment 885, Blocks 930 and 932.

For example, the next sub-segment 885 includes the local maximum amplitude 887 and one local amplitude 888, so that the sub-segment rate is equal to the RR interval RR3. The next sub-segment 885 includes the local maximum amplitude 887 and one local amplitude 888, so that the sub-segment rate is equal to the RR interval, RR4. No sub-segment rate is determined for the last sub-segment 885 since, although the last sub-segment included a local maximum amplitude, which corresponded to the overall maximum amplitude for the window 886, the last sub-segment did not include at least one additional local amplitude 888 that was determined in Block 918 to be greater than the local amplitude threshold.

Once a rate has been determined for each of the qualified sub-segments 885, No in Block 934, the device determines the corrected rate for the three second window, Block 936, based on the determined sub-segment rates. For example, the device sorts the determined sub-segment rates from fastest to slowest, and uses the average of a predetermined number of the sorted sub-segment rates to determine the corrected rate. In particular, according to an embodiment of the present invention, the device makes the determination based on the number of sub-segment rates that were determined, so that if a sub-segment rate was determined for all four of the sub-segments, the corrected rate is determined as the average of the second and third sub-segment rates of the sorted sub-segment rates. If a sub-segment rate was determined for three of the four sub-segments, the corrected rate is determined as the average of the second and third sub-segment rates of the sorted sub-segment rates, and if a sub-segment rate was determined for only two of the sub-segments, the corrected rate is determined as the average of the first and second sub-segment rates of the sorted sub-segment rates.

Figure 22:
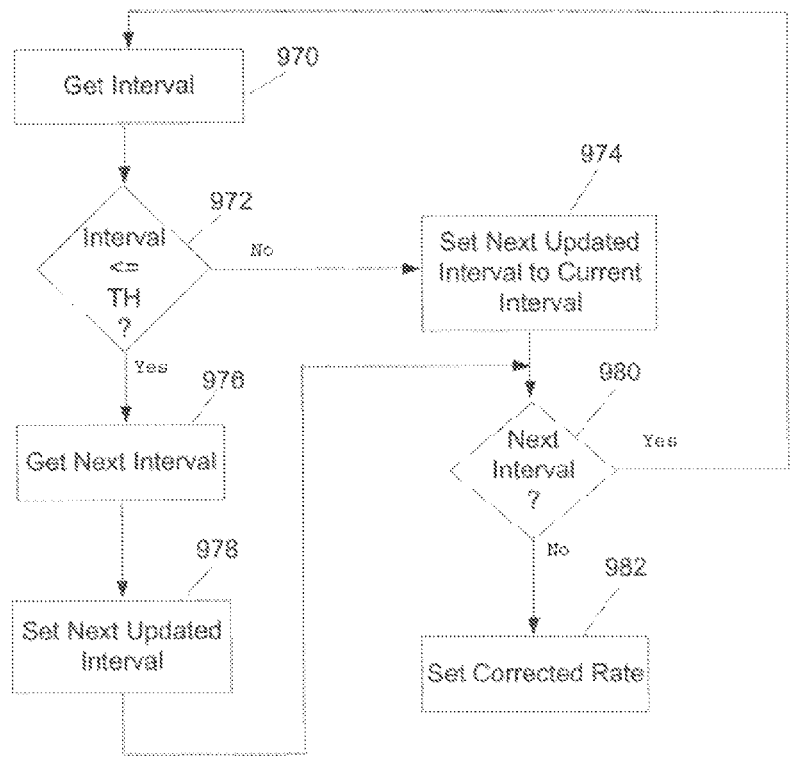
FIG. 22 is a flowchart of a method of determining a corrected heart rate in response to oversensing according to an embodiment of the present invention.
Figure 23:
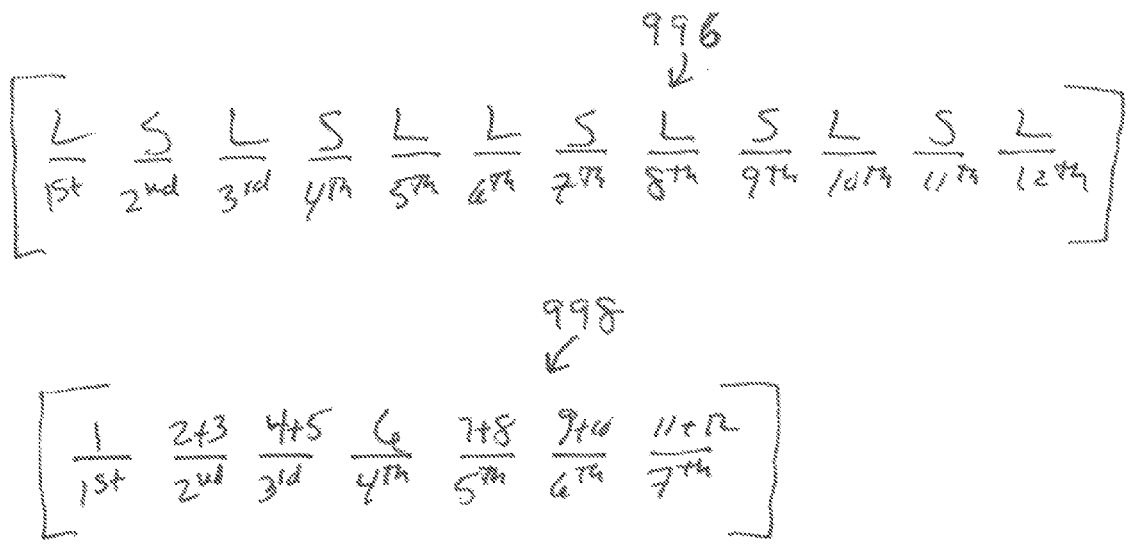
FIG. 23 is an exemplary schematic diagram of a buffer of RR intervals generated according to an embodiment of the present invention.

FIG. 22 is a flowchart of a method for determining a corrected rate according to an embodiment of the present invention. FIG. 23 is an exemplary schematic diagram of a buffer of RR intervals generated according to an embodiment of the present invention. In particular, FIG. 23 illustrates an example of a buffer of twelve RR intervals 996 that were stored during an instance of oversensing due to a slow monomorphic ventricular tachycardia with a wide QRS complex, in which the first interval is a long interval L, the second interval is a short interval S, the third interval is a long interval L, and so forth.

According to another embodiment of the present invention, in order to determine the corrected heart rate in response to the determination of oversensing, the device identifies short-long interval patterns by looking sequentially at each RR interval, Block 970, starting with the first RR interval of the stored buffer of 12 RR intervals, and generating an update RR interval to be stored in an updated RR interval buffer based on a determination as to whether the interval is a short interval or a long interval. In particular, as illustrated in FIG. 22, in order to identify short-long interval patterns, the device obtains an RR interval, Block 970, and determines whether the RR interval is less than or equal to an interval threshold, Block 972. If the current RR interval is not less than the interval threshold, No in Block 972, the RR interval is likely a long interval and therefore not a first interval of a short-long interval pattern. Therefore the current RR interval is set as the next RR interval of the updated RR intervals, Block 974. If the current RR interval is less than or equal to the interval threshold, Yes in Block 972, the current RR interval is likely a short interval, and therefore the device obtains the next RR interval immediately subsequent to the current RR interval, Block 976, and sets the next updated RR interval equal to the sum of the current RR interval, i.e., the short RR interval and the next RR interval, Block 978.

According to an embodiment of the present invention, the interval threshold is the sum of the blanking period, i.e., 180 ms for example, and a rate correction constant associated with a maximum width of the particular waveform that the device is attempting to identify. For example, in an embodiment of the present invention, the rate correction constant is set as 20 ms when the device is attempting to identify instances of oversensing due to a slow monomorphic ventricular tachycardia with a wide QRS complex.

Once an updated RR interval has been determined based on a single long RR interval, Block 974, or based on the sum of a short interval and a next interval, Block 978, the device then determines in Block 980 whether each one of the 12 buffered RR intervals have been either identified as being a long interval, Block 972, and therefore used alone to generate a next update interval, or utilized in combination with a preceding interval determined to be a short interval to generate the next updated interval Blocks 976-978. If all of the 12 buffered RR intervals have not been utilized to generate a next updated RR interval, Yes in Block 980, the process is repeated with the next available buffered RR interval, Block 970. If all of the 12 buffered RR intervals have been utilized to generate an updated RR interval, No in Block 980, the device sets the corrected rate based on the buffer of updated RR intervals, Block 982. For example, according to an embodiment of the present invention, the device sets the corrected rate equal to the mean of the second through the last updated RR interval of the buffer of updated RR intervals.

As illustrated in FIGS. 22 and 23, since the first interval of buffer 996 is a long interval, No in Block 972, the first updated interval of a buffer of updated RR intervals 998 is set equal to the first interval of buffer 996. Since the second interval of buffer 996 is a short interval, the second updated interval of buffer 998 is set equal to the sum of the second and third intervals of buffer 996. The process is repeated, resulting in the buffer of updated RR intervals 998 containing seven updated intervals, so that the corrected rate is determined in Block 982 as the mean of the second through the seventh updated RR interval from buffer 998.

According to an embodiment of the present invention, the interval threshold in Block 972 may correspond to a trimmed mean of the buffered 12 RR intervals, such as a trimmed mean of the third through the tenth sorted RR intervals, as utilized above for example TM. In this way, in the determination of the corrected rate, the device first sorts the 12 buffered RR intervals from smallest to largest, and sets the interval threshold utilized in Block 972 as the trimmed mean of the third through tenth RR interval. Once the interval threshold has been set, the rate correction process, Blocks 970-982, is performed as described above. As a result, the corrected rate is determined in response to both a sorted and a non-sorted buffer of the buffer of 12 RR intervals.

Figure 24:
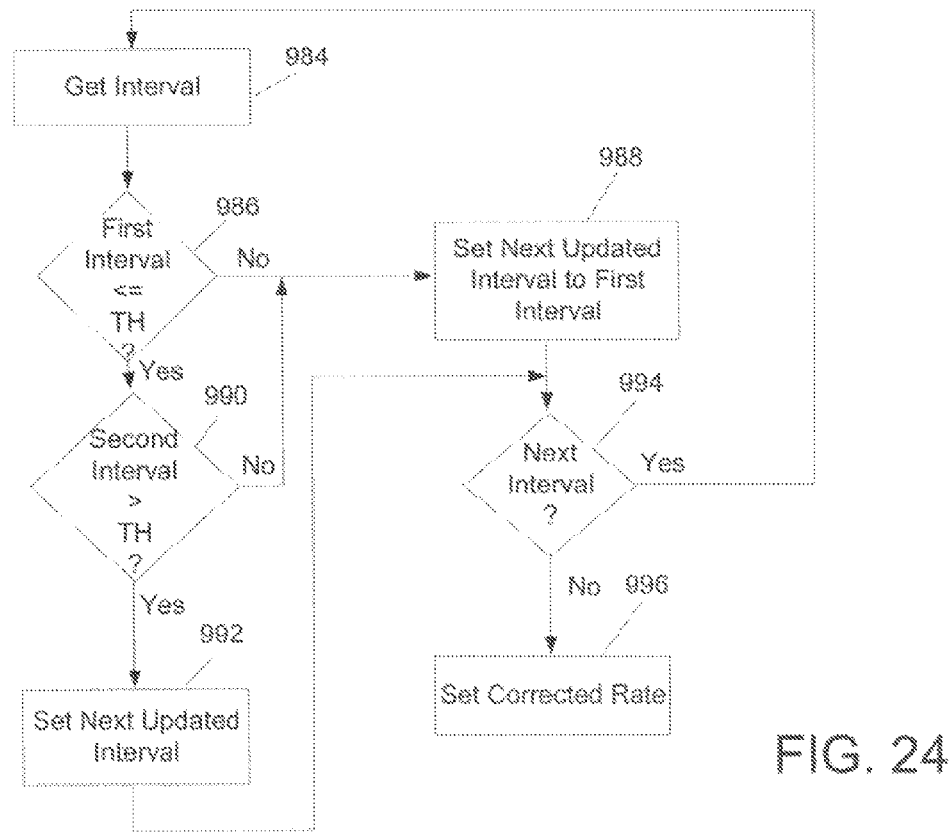
FIG. 24 is a flowchart of a method for determining a corrected rate according to an embodiment of the present invention.
Figure 25:
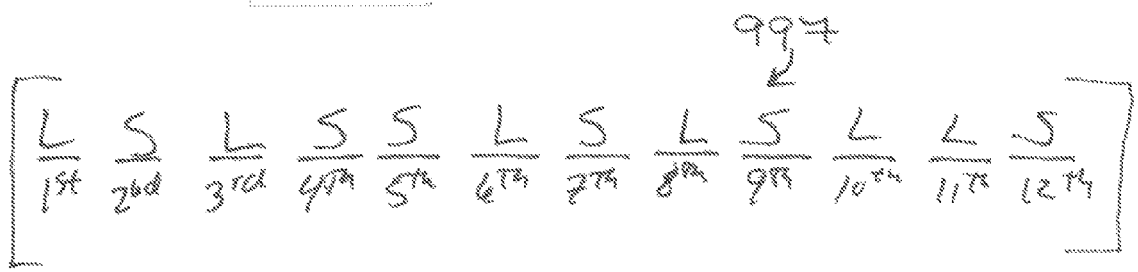
FIG. 25 is an exemplary schematic diagram of a buffer of RR intervals generated according to an embodiment of the present invention.

FIG. 24 is a flowchart of a method for determining a corrected rate according to an embodiment of the present invention. FIG. 25 is an exemplary schematic diagram of a buffer of RR intervals generated according to an embodiment of the present invention. In particular, FIG. 25 illustrates an example of a buffer of twelve RR intervals 997 that were stored during an instance of oversensing due to a slow monomorphic ventricular tachycardia with a wide QRS complex, in which the first interval is a long interval L, the second interval is a short interval S, the third interval is a long interval L, the fourth and fifth intervals are short intervals, and so forth. In order to further insure that rate correction is only applied when a short-long RR interval pattern exists, the device performs the rate correction according to another embodiment of the present by looking sequentially at two adjacent RR intervals, Block 984, starting with the first two RR intervals of the stored buffer of 12 RR intervals, generates an updated RR interval buffer based on whether the first RR interval of the adjacent RR intervals is a short interval and the second RR interval is a long interval, and determines the corrected rate based on the updated intervals in the updated RR interval buffer. In particular, as illustrated in FIG. 24, the device obtains adjacent RR intervals, Block 984, starting with the first and second RR interval for example, and determines whether the first RR interval of the two adjacent RR intervals is less than or equal to an interval threshold, Block 986. If the first RR interval is not less than or equal to the interval threshold, No in Block 986, the first RR interval is likely a long interval, negating the possibility that the current two intervals correspond to a short-long interval sequence, and therefore the first RR interval is set as the next updated RR interval of the buffer of updated RR intervals, Block 988.

If the first RR interval is less than or equal to the interval threshold, Yes in Block 986, the current RR interval is likely a short interval, and therefore the device determines whether the second RR interval, i.e., the subsequent interval adjacent to the first RR interval, is greater than the interval threshold, Block 990. If the second RR interval is not greater than the interval threshold, No in Block 990, both the first RR interval and the second RR interval are likely short intervals, negating the possibility that the current two RR intervals correspond to a short-long interval sequence, and therefore the first RR interval is set as the next updated RR interval of the buffer of updated RR intervals, Block 988. If the first RR interval is less than or equal to the interval threshold, Yes in Block 986, and the second RR interval is greater than the interval threshold, Yes in Block 990, indicating that the first RR interval is a short interval and the second RR interval is a long interval, the device sets the next updated RR interval in the stored buffer of RR intervals based on the two current intervals, Block 992. For example, according an embodiment of the present invention, the device sets the next updated RR interval equal to the sum of the current first RR interval and second RR interval.

According to an embodiment of the present invention, the interval threshold of Blocks 986 and 990 is the sum of the blanking period, i.e., 180 ms for example, and a rate correction constant associated with a maximum width of the particular waveform that the device is attempting to identify. For example, in an embodiment of the present invention, the rate correction constant is set as 60 ms when the device is attempting to identify instances of oversensing due to a slow monomorphic ventricular tachycardia with a wide QRS complex.

Once an updated RR interval has been determined based on a single long RR interval, Block 988, or based on the sum of a short interval and a long interval, Block 992, the device then determines in Block 994 whether each one of the 12 buffered RR intervals have been either identified as being a long interval, Block 986, and therefore used alone to generate a next update interval, Block 988, or utilized in combination with an adjacent RR interval determined to form a short-long interval sequence, Block 992. If all of the 12 buffered RR intervals have not been utilized to generate a next updated RR interval, Yes in Block 994, the process is repeated with the next available adjacent buffered RR intervals, Block 984. If all of the 12 buffered RR intervals have been utilized to generate a next updated RR interval, No in Block 994, the device sets the corrected rate based on the updated RR intervals, Block 996. For example, according to an embodiment of the present invention, the device sets the corrected rate equal to the mean of the second through the last updated RR intervals of the updated RR intervals.

As illustrated in FIGS. 24 and 25, since the first interval of buffer 997 is a long interval, No in Block 986, the first updated interval of a buffer of updated RR intervals 999 is set equal to the first interval of buffer 997. Since the second interval of buffer 997 is a short interval, Yes in Block 986, and the third interval is a long interval, Yes in Block 990, the second updated interval of buffer 999 is set equal to the sum of the second and third RR intervals of buffer 997. Since the fourth RR interval of buffer 997 is a short interval, Yes in Block 986, and the fifth RR interval is a short interval, No in Block 990, the third updated interval of buffer 999 is set equal to the fourth interval of buffer 997. Since the fifth interval was not included in generating the third updated interval, the device utilizes the fifth and sixth intervals of buffer 997 in the next iteration, resulting in a determination that the fifth RR interval of buffer 997 is a short interval, Yes in Block 986, and the sixth RR interval is a long interval, Yes in Block 990, so that the fourth updated RR interval of buffer 999 is set equal to the sum of the fifth and sixth intervals of buffer 997. The process is repeated, resulting in the buffer of updated RR intervals 998 containing eight updated intervals, so that the corrected rate is determined in Block 996 as the mean of the second through the seventh updated RR interval from buffer 999.

The present invention may utilize other embodiments for determining the corrected rate in place of the embodiments described above. For example, according to another embodiment of the present invention, in order to determine the corrected heart rate in response to oversensing, the device sorts the 12 buffered RR intervals from smallest to largest so that the corrected rate is determined based on predetermined RR intervals from the sorted RR intervals. For example, according to an embodiment of the present invention, the corrected rate is determined as the sum of the mean of second through fifth smallest RR interval and the mean of the eighth through eleventh RR interval.

According to another embodiment of the present invention, in order to determine the corrected heart rate in response to oversensing, the device sorts the 12 buffered RR intervals from smallest to largest so that the corrected rate is determined based on one or more predetermined RR intervals from the sorted RR intervals and the spectral width of the signal for the three-second segment associated with each channel ECG1 and ECG2, determined as described above. For example, according to an embodiment of the present invention, the corrected rate is determined as the sum of the $9^{th}$ fastest RR interval of the sorted RR intervals and the spectral width associated with the three second segment for the channel ECG1 or ECG2.

Figure 26:
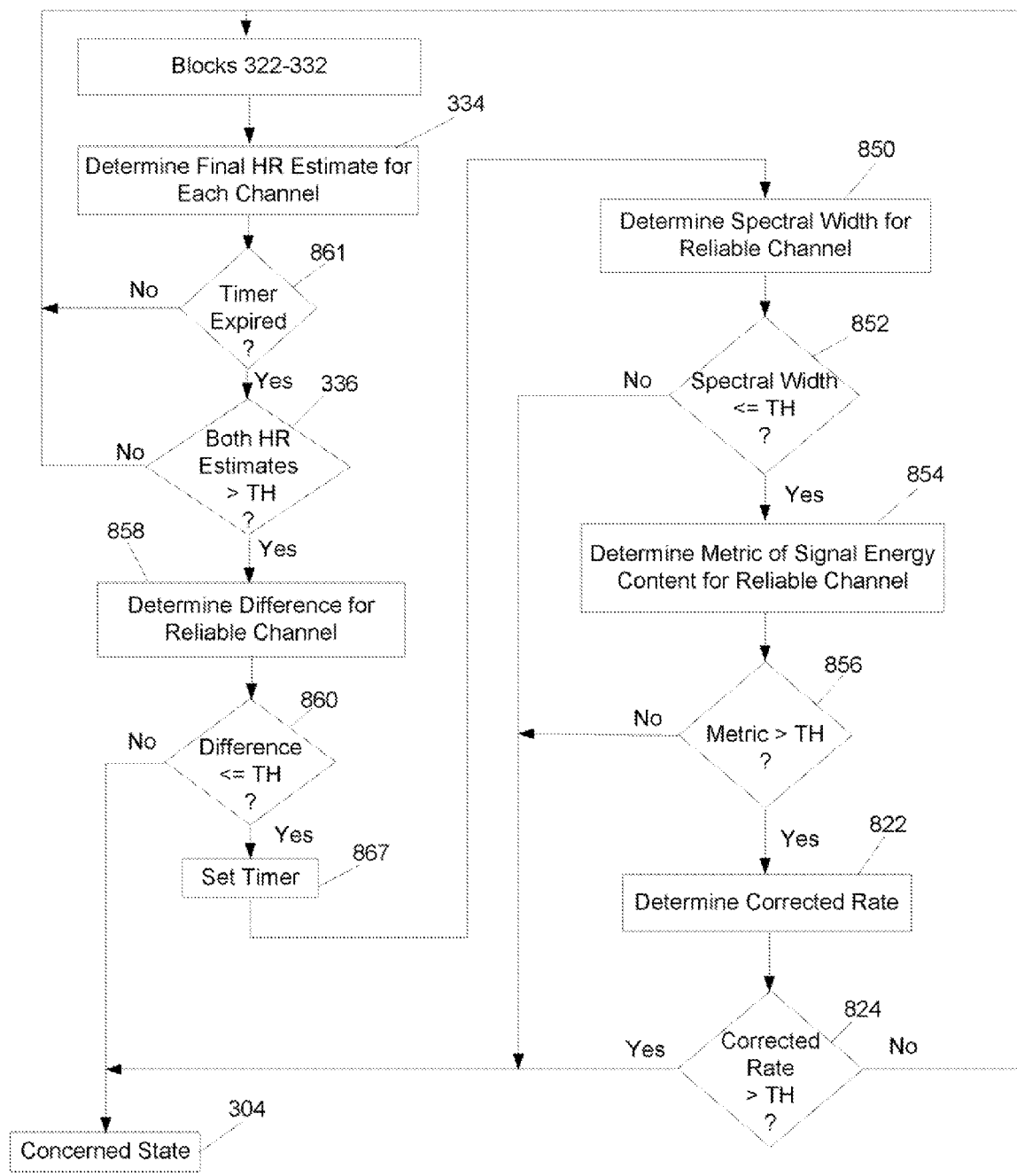
FIG. 26 is a flowchart of a method for detecting cardiac events in a medical device according to an embodiment of the present invention.

FIG. 26 is a flowchart of a method for detecting cardiac events in a medical device according to an embodiment of the present invention. The method described in FIG. 26 is similar to the method described above in reference to FIG. 15, and includes the determination of whether oversensing has occurred in a situation where only one of the sensing channels ECG1 and ECG2 has been determined to be reliable, described above in reference to FIG. 16B. Therefore, a description of those steps already described above in reference to FIGS. 15 and 16B will not be repeated for brevity sake. The embodiment of FIG. 26 differs only in that it includes additional steps associated with a timer for controlling the rate at which the oversensing determination is performed, which results in a reduction in the amount of processing that occurs during the oversensing determination, thereby increasing the battery life of the device.

In particular, as illustrated in FIG. 26, once the device has determined the final heart rate estimate for each channel ECG1 and ECG2 using the methods described above in reference to Blocks 322-334 of FIG. 7A, for example, a determination is made as whether a timer has expired, Block 861. The timer of Block 861, which is initialized as being expired, i.e., equal to zero, is set during the oversensing determination as will be described below. According to an embodiment of the present invention, the timer is set as 750 ms, which corresponds to the time associated with a single sub-segment of the three-second window, although any desired time period for controlling the rate at which the oversensing determination is performed may be utilized.

If the timer has not expired, i.e., at least one of the oversensing criteria has been satisfied within the last 750 ms, No in Block 861, the determination of the heart rate estimate for each channel is repeated, Blocks 322-334. If the timer has expired, i.e., at least one of the oversensing criteria has not been satisfied within the last 750 ms, Yes in Block 861, the determination is then made as to whether the final heart rate estimates is greater than the predetermined VT/VF threshold, Block 336, described above. If the final heart rate estimates are not greater than the VT/VF threshold, a new heart rate estimate is determined, Blocks 322-334. If the final heart rate estimates are greater than the VT/VF threshold, the oversensing determination is made for the current generated heart rate estimate. According to the embodiment of the present invention illustrated in FIG. 26, the oversensing determination includes all three of the previously described oversensing characteristics, spectral width, the metric of signal energy content, and the heart rate metric difference, with the heart rate metric difference being the initial oversensing characteristic. However, as mentioned above, embodiments of the present invention may include any number or combination of the oversensing characteristics may be utilized, performed in any desired sequence.

In particular, for example, if the first channel ECG1 was determined to be unreliable and the second channel ECG2 was determined to be the reliable channel, a heart rate metric difference is determined for the reliable channel ECG2, Block 858, and a determination as to whether the heart rate metric difference is less than or equal to the heart rate metric difference threshold, Block 860. If the heart rate metric difference is greater than the heart rate metric difference threshold, No in Block 860, oversensing is determined to not be occurring, and the device transitions from the not concerned state 302 to the concerned state 304. If the heart rate metric difference is less than or equal to the heart rate metric difference threshold, Yes in Block 860, the timer is set, Block 867. A spectral width is then determined for the reliable channel ECG2, Block 850, and a determination is made as to whether the spectral width is less than or equal to the spectral width threshold, Block 852.

If the spectral width is not less than or equal to the spectral width threshold, No in Block 852, oversensing is determined not to be occurring, and the device transitions to the concerned state, Block 304. If the spectral width is less than or equal to the spectral width threshold, Yes in Block 852, a metric of signal energy content is determined for the reliable channel ECG2, Block 854, and a determination is made as to whether the metric of signal energy content is greater than the metric of signal energy content threshold, Block 856.

If the metric of signal energy content is not greater than the metric of signal energy content threshold, No in Block 856, oversensing is determined to not be occurring, and the device transitions from the not concerned state 302 to the concerned state 304. If the metric of signal energy content is greater than the metric of signal energy content threshold, Yes in Block 856, oversensing is determined to likely be occurring and the corrected rate is determined, Block 822 of FIG. 15, using the rate correction technique described above. If the corrected rate is greater than the predetermined VT/VF threshold, Yes in Block 824, oversensing is determined to not be occurring, and the device transitions from the not concerned state 302 to the concerned state 304.

If the corrected heart rate is not greater than the predetermined VT/VF threshold, No in Block 824, a new current heart rate estimate is then determined, Blocks 322-332 and the process is repeated. However, since no oversensing was determined to be occurring for the previous heart rate estimate, and therefore the timer was initiated in Block 867, once the next heart rate estimate has been determined, Block 334, the determination of oversensing will be delayed until a desired amount of new sensing data has been analyzed, since the timer will not be expired, No in Block 861. While the amount of time necessary for the oversensing determination and the rate correction to occur will vary depending on the number of oversensing characteristics utilized, the inventor has found that the oversensing determination process of FIG. 26 may take approximately 50 ms to be completed. By setting the timer in Block 867 as being 750 ms, for example, the amount of time between sequential oversensing determinations is increased so that a more appropriate amount of sensing data is reviewed before the oversensing determination is repeated. In this way, the amount of processing resulting during the oversensing determination is reduced, increasing the battery life of the device.

While the determination of oversensing and the generation of the corrected rate according to the present invention has been described using two sensing vectors, it is understood that the present invention could also be utilized to determine the presence of oversensing and to generate the corrected rate using only one sensing vector. Similarly, while the present invention is described when utilized in a subcutaneous device, it is understood that the oversensing detection and subsequent rate correction of the present invention may also be utilized in known transvenous systems, such as the transvenous system described in U.S. Pat. No. 7,133,718 to Bakken et al., for example, incorporated herein in it's entirety.

It will be apparent from the foregoing that while particular embodiments of the invention have been illustrated and described, various modifications can be made without departing from the spirit and scope of the invention. Accordingly, it is not intended that the invention be limited, except as by the appended claims. For example, as illustrated in FIG. 71, during the noise determination of Block 744, the determination is made for each channel ECG1 and ECG2 as to whether the channel is corrupted by noise as described above. However, according to an embodiment of the present invention, once noise is determined to be present in either channel, No in Blocks 380, 382 or 388, Yes in Block 384 of FIG. 7C, both channels are classified as being not shockable, Block 748.

If noise is not present in either channel ECG1 and ECG2, No in Block 744, a determination is made as for each channel ECG1 and ECG2 as to whether the channel is in a VF shock zone. For example, according to an embodiment of the present invention, a determination is made that channel ECG1 is in the VF shock zone, Yes in Block 748, if, for channel ECG1, both the low slope content is less than the first boundary 502 and the spectral width is less than the second boundary 504, as described above. The three second segment for that channel ECG1 is then determined to be shockable, Block 750 and the associated buffer for that channel is updated accordingly. If either the low slope content for the channel is not less than the first boundary 502 or the spectral width is not less than the second boundary, the channel ECG1 is determined not to be in the VF shock zone, No in Block 748, the three second segment for that channel ECG1 is then determined to be not shockable, Block 752, and the associated buffer is updated accordingly.

Similarly, a determination is made that channel ECG2 is in the VF shock zone, Yes in Block 754, if, for channel ECG2, both the low slope content is less than the first boundary 502 and the spectral width is less than the second boundary 504, as described above. The three second segment for that channel ECG2 is then determined to be shockable, Block 756 and the associated buffer for that channel is updated accordingly. If either the low slope content for the channel is not less than the first boundary 502 or the spectral width is not less than the second boundary, the channel ECG2 is determined not to be in the VF shock zone, No in Block 754, the three second segment for that channel ECG2 is then determined to be not shockable, Block 758, and the associated buffer is updated accordingly.

Once the classification of both of the channels ECG1 and ECG2 as being either shockable, Block 752 and 758, or not shockable, Blocks 748, 754 and 760, a determination is made as to whether the device should transition from the concerned state 304 to the armed state 306, Block 762. The determination of whether the device should transition from the concerned state 304 to the armed state 306 in Block 762, in addition to the subsequent determination of whether to transition from the concerned state 304 to the not concerned state 302 in Block 764 are similar to the determination of whether the device should transition from the concerned state 304 to the armed state 306 in Block 370, and to the determination of whether to transition from the concerned state 304 to the not concerned state 302 in Block 372 in FIG. 7B described above, and therefore will not be repeated for the sake of brevity.

Some of the techniques described above may be embodied as a computer-readable medium comprising instructions for a programmable processor such as microprocessor 142, pacer/device timing circuit 178 or control circuit 144 shown in FIG. 3. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

While a particular embodiment of the present invention has been shown and described, modifications may be made. It is therefore intended in the appended claims to cover all such changes and modifications, which fall within the true spirit and scope of the invention.

We claim:

1. An apparatus for adjusting a sensing parameter in a medical device, comprising:
    means for sensing cardiac signals;
    means for determining intervals in response to the sensed cardiac signals;
    means for determining interval patterns associated with the determined intervals, wherein the means for determining interval patterns comprises means for sorting the determined intervals from a smallest interval to a largest interval; and
    means for updating the sensing parameter in response to the determined interval patterns, wherein the means for updating the sensing parameter comprises:
        means for determining a first mean of a first predetermined number of the sorted determined intervals; and
        means for determining a second mean of a second predetermined number of the sorted determined intervals, each interval of the second predetermined number of intervals being greater than intervals of the first predetermined number of the sorted determined intervals.

2. The apparatus of claim 1, wherein the means for updating the sensing parameter further comprises
    means for determining a sum of the determined first mean and the determined second mean.

3. The apparatus of claim 1, wherein the means for updating the sensing parameter comprises:
    means for determining a spectral width associated with the determined intervals; and
    means for determining a sum of the spectral width and a predetermined interval of the determined intervals.

4. The apparatus of claim 1, further comprising means for updating the determined intervals in response to the determined interval patterns, wherein the sensing parameter is updated in response to the updated intervals.

5. The apparatus of claim 1, wherein the cardiac signals are sensed non-transveneously.

6. The apparatus of claim 1, wherein the adjusting of the sensing parameter is in response to oversensing being determined by the apparatus.

7. A method of updating a sensing parameter in a medical device, comprising:
    sensing cardiac signals;
    determining intervals in response to the sensed cardiac signals;
    determining interval patterns associated with the determined intervals, wherein determining interval patterns comprises sorting the determined intervals from a smallest interval to a largest interval; and
    updating the sensing parameter in response to the determined interval patterns, wherein updating the sensing parameter comprises:

determining a first mean of a first predetermined number of the sorted determined intervals; and determining a second mean of a second predetermined number of the sorted determined intervals, each interval of the second predetermined number of intervals being greater than intervals of the first predetermined number of the sorted determined intervals.

8. The method of claim 7, wherein updating the sensing parameter further comprises determining a sum of the determined first mean and the determined second mean.

9. The method of claim 7, wherein updating the sensing parameter comprises:

determining a spectral width associated with the determined intervals; and determining a sum of the spectral width and a predetermined interval of the determined intervals.

10. The method of claim 7, further comprising updating the determined intervals in response to the determined interval patterns, wherein the sensing parameter is updated in response to the updated intervals.

11. The method of claim 7, wherein the cardiac signals are sensed non-transveneously.

12. The method of claim 7, wherein the adjusting of the sensing parameter is in response to oversensing being determined.

13. An apparatus for adjusting a sensing parameter in a medical device, comprising:

means for sensing cardiac signals;

means for determining intervals in response to the sensed cardiac signals;

means for determining interval patterns associated with the determined intervals, wherein the means for determining interval patterns comprises means for sorting the determined intervals from a smallest interval to a largest interval; and means for updating the sensing parameter in response to the determined interval patterns, wherein the means for updating the sensing parameter comprises means for determining a spectral width associated with the determined intervals and means for determining a sum of the spectral width and a predetermined interval of the determined intervals.

14. A method of updating a sensing parameter in a medical device, comprising:

sensing cardiac signals;

determining intervals in response to the sensed cardiac signals;

determining interval patterns associated with the determined intervals, wherein determining interval patterns comprises sorting the determined intervals from a smallest interval to a largest interval; and updating the sensing parameter in response to the determined interval patterns, wherein updating the sensing parameter comprises determining a spectral width associated with the determined intervals and determining a sum of the spectral width and a predetermined interval of the determined intervals.

* * * * *